United States Patent
Tamura et al.

(10) Patent No.: US 11,076,823 B2
(45) Date of Patent: Aug. 3, 2021

(54) X-RAY CT APPARATUS INCLUDING A PHOTON-COUNTING DETECTOR AND CIRCUITRY CONFIGURED TO SET A CONTROL PARAMETER CORRESPONDING TO A POSITION OF EACH DETECTING ELEMENT IN THE PHOTON-COUNTING DETECTOR

(71) Applicant: CANON MEDICAL SYSTEMS CORPORATION, Otawara (JP)

(72) Inventors: Emi Tamura, Yokohama (JP); Hiroaki Miyazaki, Otawara (JP); Hiroaki Nakai, Nasushiobara (JP); Toshiyuki Ono, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 107 days.

(21) Appl. No.: 16/021,951

(22) Filed: Jun. 28, 2018

(65) Prior Publication Data
US 2019/0000409 A1    Jan. 3, 2019

(30) Foreign Application Priority Data

Jun. 28, 2017  (JP) .............................. JP2017-126634
Jun. 28, 2017  (JP) .............................. JP2017-126660

(51) Int. Cl.
*A61B 6/03* (2006.01)
*A61B 6/00* (2006.01)

(52) U.S. Cl.
CPC ............ *A61B 6/4241* (2013.01); *A61B 6/032* (2013.01); *A61B 6/035* (2013.01); *A61B 6/42* (2013.01);

(Continued)

(58) Field of Classification Search
CPC ........... A61B 6/032; A61B 6/035; A61B 6/42; A61B 6/4208; A61B 6/4241; A61B 6/54;
(Continued)

(56) References Cited

U.S. PATENT DOCUMENTS 5,568,530 A    10/1996  Saito et al.
6,953,935 B1 * 10/2005  Hoffman ................. G01T 1/242
                                                            250/370.13

(Continued)

FOREIGN PATENT DOCUMENTS

JP    2009-25308        2/2009
WO    WO 2016/042981 A1  3/2016
WO    WO 2017/001269 A1  1/2017

OTHER PUBLICATIONS

Notification of Reasons for Refusal dated Mar. 2, 2021 in Japanese Patent Application No. 2017-126634, 5 pgs.

(Continued)

*Primary Examiner* — Allen C. Ho
(74) *Attorney, Agent, or Firm* — Oblon, McClelland, Maier & Neustadt, L.L.P.

(57) ABSTRACT

An X-ray CT apparatus according to one embodiment includes a photon counting detector and a processing circuitry. The photon counting detector includes a plurality of detecting elements configured to detect X-rays. The processing circuitry is configured to set a control parameter corresponding to a position of each detecting element of the plurality of detecting elements in the photon counting detector.

27 Claims, 24 Drawing Sheets

(52) U.S. Cl.
CPC ............ *A61B 6/4208* (2013.01); *A61B 6/482* (2013.01); *A61B 6/5211* (2013.01); *A61B 6/54* (2013.01); *A61B 6/542* (2013.01); *A61B 6/544* (2013.01); *A61B 6/545* (2013.01); *A61B 6/585* (2013.01)

(58) Field of Classification Search
CPC ......... A61B 6/542; A61B 6/544; A61B 6/482; A61B 6/58; A61B 6/582; A61B 6/585; A61B 6/545
USPC .............. 378/19, 98.8, 98.9, 98.11, 207, 62; 250/370.09
See application file for complete search history.

(56) References Cited

U.S. PATENT DOCUMENTS

| | | | | |
|---|---|---|---|---|
| 7,092,481 | B2 * | 8/2006 | Hoffman | A61B 6/4241 250/370.09 |
| 7,105,828 | B2 * | 9/2006 | Unger | G01T 1/2018 250/370.06 |
| 7,149,278 | B2 * | 12/2006 | Arenson | A61B 6/4241 378/19 |
| 7,332,724 | B2 * | 2/2008 | Hefetz | A61B 6/032 250/370.06 |
| 7,403,589 | B1 * | 7/2008 | Short | A61B 6/032 250/370.11 |
| 7,433,443 | B1 * | 10/2008 | Tkaczyk | A61B 6/032 378/19 |
| 7,486,764 | B2 * | 2/2009 | Tkaczyk | G01T 1/249 250/370.09 |
| 7,512,210 | B2 * | 3/2009 | Possin | A61B 6/032 250/370.09 |
| 7,532,703 | B2 * | 5/2009 | Du | A61B 6/032 378/116 |
| 7,567,646 | B2 * | 7/2009 | Buchinsky | A61B 6/032 250/370.11 |
| 7,606,346 | B2 * | 10/2009 | Tkaczyk | A61B 6/032 250/370.09 |
| 7,795,590 | B2 * | 9/2010 | Takahashi | G01T 1/2018 250/363.02 |
| 8,237,128 | B2 * | 8/2012 | Steadman Booker | G01T 1/2928 250/370.09 |
| 8,513,614 | B2 * | 8/2013 | Kraft | G01T 1/24 250/370.09 |
| 8,610,081 | B2 | 12/2013 | Rao et al. | |
| 8,774,353 | B2 * | 7/2014 | Herrmann | G01T 1/247 378/19 |
| 8,913,711 | B2 * | 12/2014 | Moriyasu | A61B 6/032 378/7 |
| 9,075,153 | B2 * | 7/2015 | Kappler | A61B 6/032 |
| 9,101,273 | B2 * | 8/2015 | Gagnon | G01T 1/24 |
| 9,216,302 | B2 * | 12/2015 | Kuwahara | A61N 5/1039 |
| 9,274,066 | B2 * | 3/2016 | Ji | G01N 23/046 |
| 9,348,036 | B2 * | 5/2016 | Yamakawa | G01T 1/24 |
| 9,532,759 | B2 * | 1/2017 | Taguchi | G16H 50/30 |
| 9,693,743 | B2 * | 7/2017 | Arakita | G01T 1/1606 |
| 9,801,595 | B2 * | 10/2017 | Cao | G01T 1/36 |
| 9,854,656 | B2 * | 12/2017 | Göderer | G01N 23/046 |
| 9,867,580 | B2 * | 1/2018 | Danielsson | H01L 27/14658 |
| 9,913,622 | B2 * | 3/2018 | Ida | A61B 6/5205 |
| 9,971,047 | B2 * | 5/2018 | Tamura | G01T 1/2985 |
| 10,034,652 | B2 * | 7/2018 | Cho | A61B 6/585 |
| 10,048,391 | B2 * | 8/2018 | Steadman Booker | G01T 1/247 |
| 10,210,633 | B2 * | 2/2019 | Yamakawa | A61B 6/032 |
| 10,292,668 | B2 * | 5/2019 | Konno | A61B 6/032 |
| 10,307,117 | B2 * | 6/2019 | Park | A61B 6/54 |
| 10,357,215 | B2 * | 7/2019 | Lee | A61B 6/46 |
| 10,383,585 | B2 * | 8/2019 | Konno | G01N 23/046 |
| 10,433,811 | B2 * | 10/2019 | Jacob | G01N 23/046 |
| 10,470,723 | B2 * | 11/2019 | Herrmann | G01T 1/17 |
| 10,621,756 | B2 * | 4/2020 | Xia | A61B 6/032 |
| 10,631,827 | B2 * | 4/2020 | Choi | A61B 8/5207 |
| 10,725,188 | B2 * | 7/2020 | Steadman Booker | G01T 1/247 |
| 10,732,309 | B2 * | 8/2020 | McCollough | A61B 6/5258 |
| 2009/0114826 | A1 | 5/2009 | Takahashi et al. | |
| 2016/0033654 | A1 | 2/2016 | Tamura et al. | |

OTHER PUBLICATIONS

Notification of Reasons for Refusal dated Mar. 2, 2021 in Japanese Patent Application No. 2017-126660, 5 pgs.

* cited by examiner

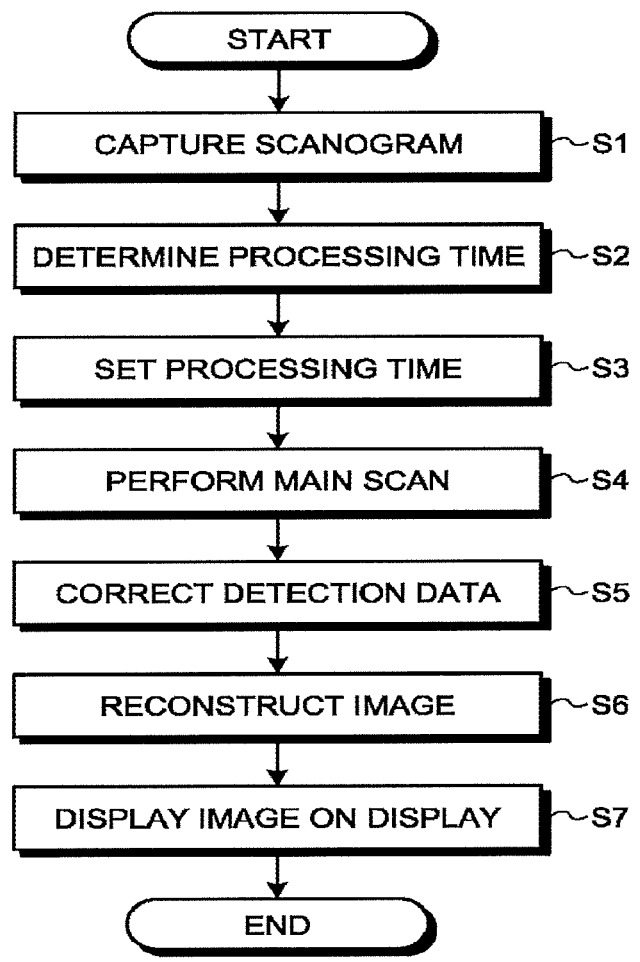

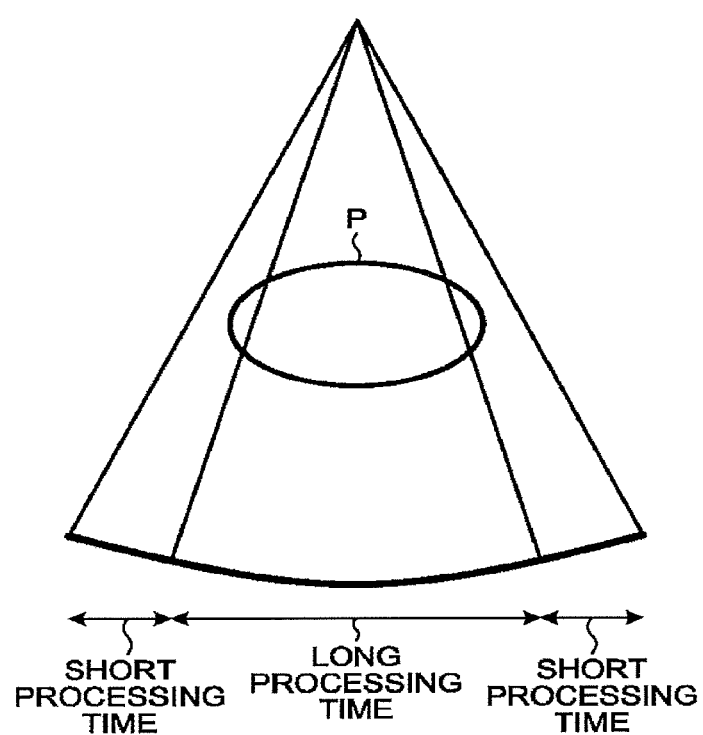

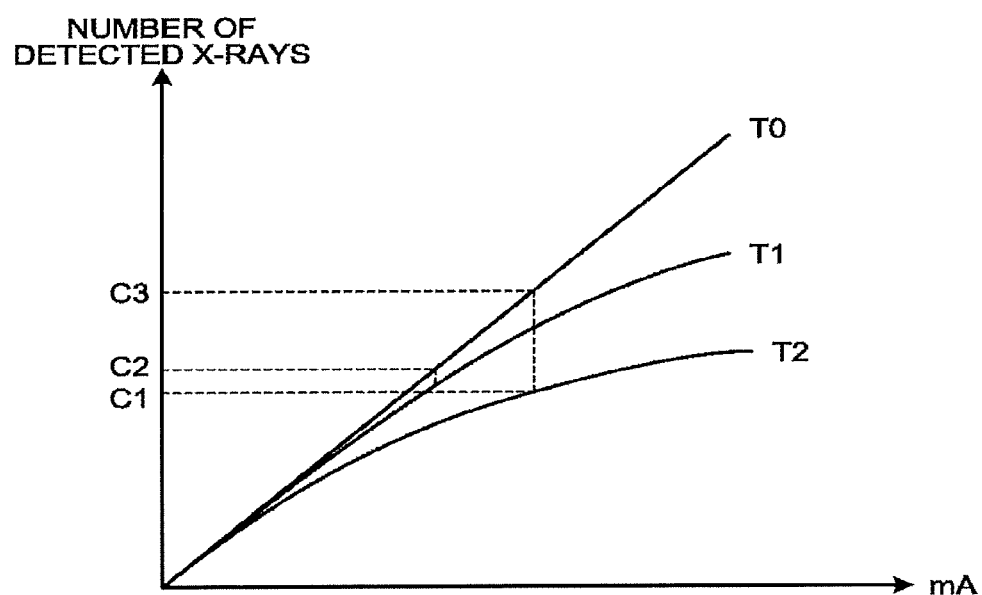

| CALCIUM [mm] \ WATER [cm] | 5 | 10 | 15 | 20 |
|---|---|---|---|---|
| 1 | $S(E)_{11}$ | $S(E)_{12}$ | $S(E)_{13}$ | $S(E)_{14}$ |
| 2 | $S(E)_{21}$ | $S(E)_{22}$ | $S(E)_{23}$ | $S(E)_{24}$ |
| 3 | $S(E)_{31}$ | $S(E)_{32}$ | $S(E)_{33}$ | $S(E)_{34}$ |
| 4 | $S(E)_{41}$ | $S(E)_{42}$ | $S(E)_{43}$ | $S(E)_{44}$ |

FIG.12

| ID | VIEW NUMBER | PROCESSING TIME |
|---|---|---|
| yyyy | N1≤N<N2 | T1 |
| | N2≤N<N3 | T1 |
| | N3≤N<N4 | T1 |
| | N4≤N<N1 | T1 |
| ... | ... | ... |
| yyyx | N1≤N<N2 | T2 |
| | N2≤N<N3 | T1 |
| | N3≤N<N4 | T2 |
| | N4≤N<N1 | T1 |
| ... | ... | ... |
| xxxx | N1≤N<N2 | T2 |
| | N2≤N<N3 | T2 |
| | N3≤N<N4 | T2 |
| | N4≤N<N1 | T2 |
| ... | ... | ... |

FIG.14

| ID | COUNT NUMBER | PROCESSING TIME |
|---|---|---|
| yyyy | $C<C11$ | T4 |
| | $C11 \leq C<C12$ | T3 |
| | $C12 \leq C<C13$ | T2 |
| | $C13 \leq C$ | T1 |
| ... | ... | ... |
| yyyx | $C<C21$ | T4 |
| | $C21 \leq C<C22$ | T3 |
| | $C22 \leq C<C23$ | T2 |
| | $C23 \leq C$ | T1 |
| ... | ... | ... |
| xxxx | $C<C31$ | T4 |
| | $C31 \leq C<C32$ | T3 |
| | $C32 \leq C<C33$ | T2 |
| | $C33 \leq C$ | T1 |
| ... | ... | ... |

FIG.16
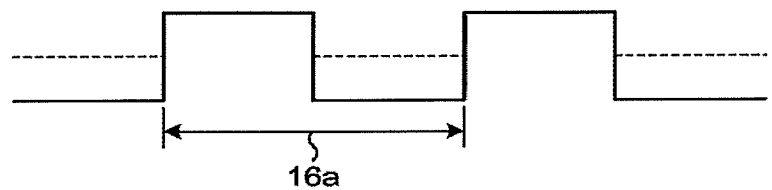
FIG.17
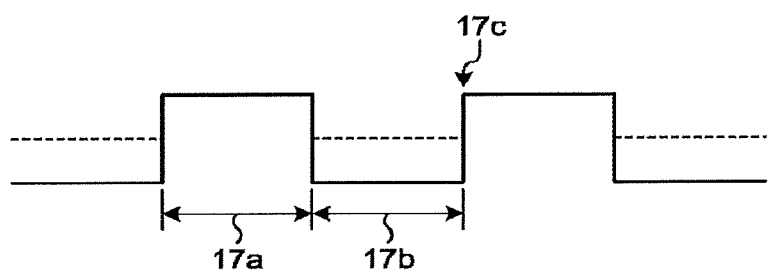
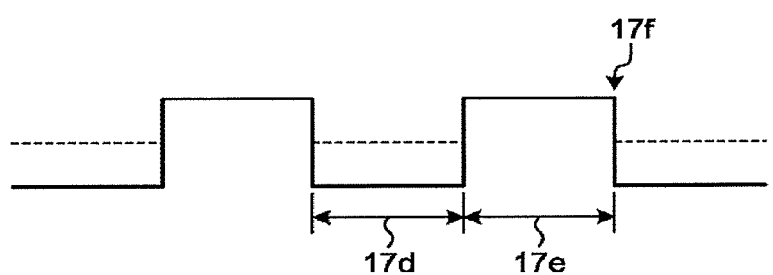

| ID | DRIVING VOLTAGE |
|---|---|
| yyyy | V1 |
| ... | ... |
| xxxx | V2 |
| ... | ... |
| zzzz | V1 |
| ... | ... |

FIG.26

| ID | VIEW NUMBER | DRIVING VOLTAGE |
|---|---|---|
| yyyy | N1≤N<N2 | V1 |
| | N2≤N<N3 | V1 |
| | N3≤N<N4 | V1 |
| | N4≤N<N1 | V1 |
| ... | ... | ... |
| yyyx | N1≤N<N2 | V2 |
| | N2≤N<N3 | V1 |
| | N3≤N<N4 | V2 |
| | N4≤N<N1 | V1 |
| ... | ... | ... |
| xxxx | N1≤N<N2 | V2 |
| | N2≤N<N3 | V2 |
| | N3≤N<N4 | V2 |
| | N4≤N<N1 | V2 |
| ... | ... | ... |

FIG.28

| ID | COUNT NUMBER | DRIVING VOLTAGE |
|---|---|---|
| yyyy | $C<C11$ | V4 |
| | $C11 \leq C < C12$ | V3 |
| | $C12 \leq C < C13$ | V2 |
| | $C13 \leq C$ | V1 |
| ... | ... | ... |
| yyyx | $C<C21$ | V4 |
| | $C21 \leq C < C22$ | V3 |
| | $C22 \leq C < C23$ | V2 |
| | $C23 \leq C$ | V1 |
| ... | ... | ... |
| xxxx | $C<C31$ | V4 |
| | $C31 \leq C < C32$ | V3 |
| | $C32 \leq C < C33$ | V2 |
| | $C33 \leq C$ | V1 |
| ... | ... | ... |

X-RAY CT APPARATUS INCLUDING A PHOTON-COUNTING DETECTOR AND CIRCUITRY CONFIGURED TO SET A CONTROL PARAMETER CORRESPONDING TO A POSITION OF EACH DETECTING ELEMENT IN THE PHOTON-COUNTING DETECTOR

CROSS-REFERENCE TO RELATED APPLICATIONS

This application is based upon and claims the benefit of priority from Japanese Patent Applications No. 2017-126660 and No. 2017-126634, both filed on Jun. 28, 2017, the entire contents of all of which are incorporated herein by reference.

FIELD

Embodiments described herein relate generally to an X-ray CT apparatus.

BACKGROUND

In medical image systems, such as a photon counting Computed Tomography (CT) system, photon counting of X-rays is performed under high dose irradiation. In the medical image systems as described above, an X-ray detector has a large number of channels, and it is common to use a highly-integrated circuit, such as an application specific integrated circuit (ASIC) or the like.

BRIEF DESCRIPTION OF THE DRAWINGS

FIG. 6 is a flowchart illustrating the flow of a process performed by an X-ray CT apparatus according to the first embodiment;
FIG. 7 is a diagram for explaining the first embodiment;
FIG. 8 is a diagram for explaining the first embodiment;
FIG. 9 is a diagram for explaining the first embodiment;
FIG. 12 is a diagram for explaining the second embodiment;
FIG. 14 is a diagram for explaining a third embodiment;
FIG. 16 is a diagram for explaining the third embodiment;
FIG. 17 is a diagram for explaining a modification of the third embodiment;
FIG. 26 is a diagram for explaining the fifth embodiment;
FIG. 28 is a diagram for explaining a sixth embodiment.

DETAILED DESCRIPTION

An X-ray Computer Tomography (CT) apparatus according to an embodiment includes a photon counting detector and processing circuitry. The photon counting detector includes a plurality of detecting elements each of which detects an X-ray. The processing circuitry sets a control parameter corresponding to a position of each of the detecting elements in the photon counting detector.

Exemplary embodiments of an X-ray CT apparatus will be described below with reference to the accompanying drawings.

The X-ray CT apparatus described in the embodiments below is an apparatus capable of performing a photon counting CT process. In other words, the X-ray CT apparatus described in the embodiments below is an apparatus capable of reconstructing X-ray CT image data having a high signal-to-noise (S/N) ratio, by counting X-rays that have passed through a subject, by using, not a conventional integral-type detector (using a current mode measuring scheme), but a detector that is based on a photon counting scheme. In principle, the description of each of the embodiments is similarly applicable to any other embodiments.

First Embodiment

Figure 1:
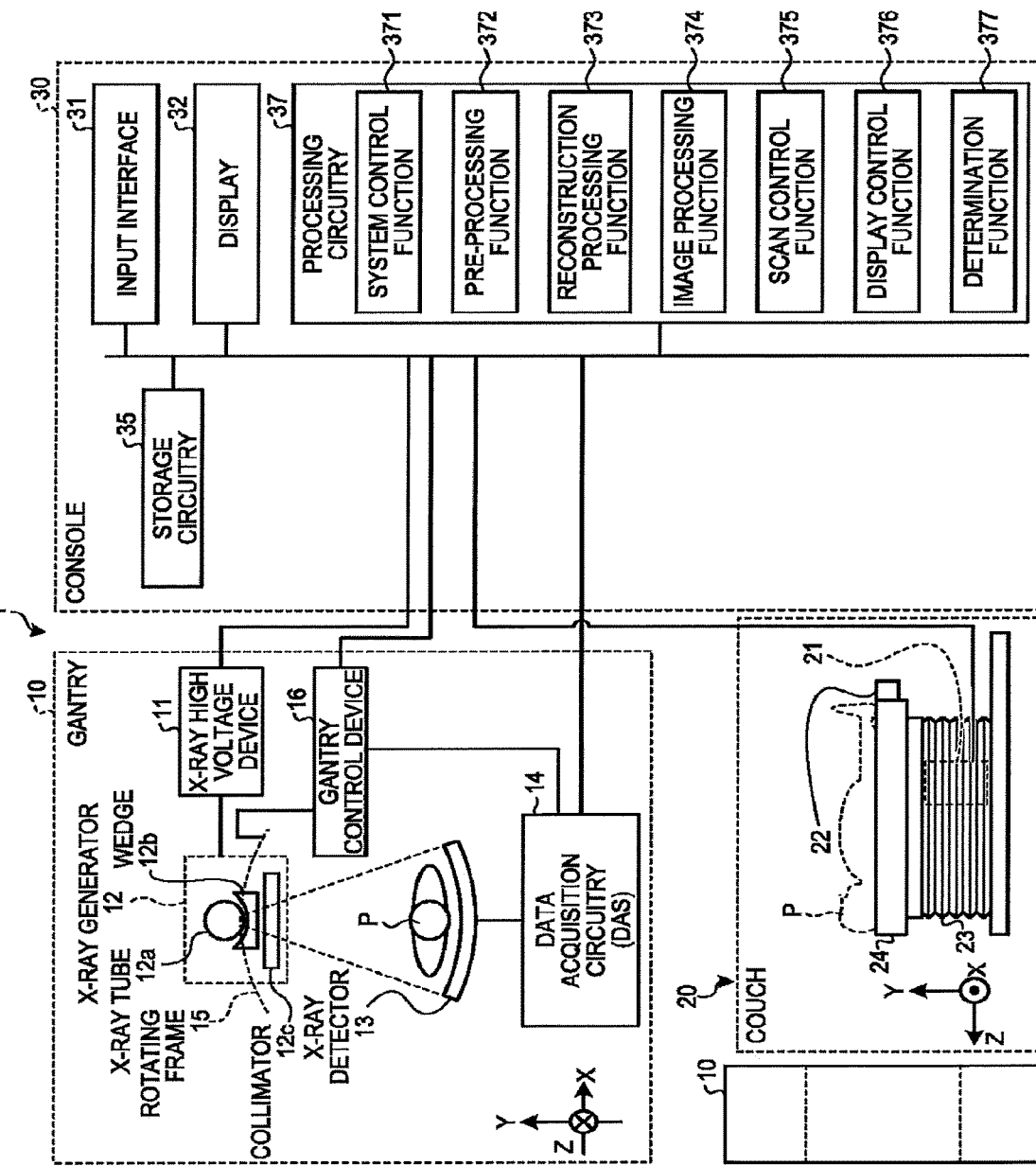
FIG. 1 is a diagram illustrating a configuration example of an X-ray CT apparatus according to a first embodiment.

FIG. 1 is a diagram illustrating a configuration example of an X-ray CT apparatus 1 according to a first embodiment. As illustrated in FIG. 1, the X-ray CT apparatus 1 according to the first embodiment includes a gantry 10, a couch 20, and a console 30.

The gantry 10 is a device that radiates X-rays onto a subject P and acquires data related to X-rays that have passed through the subject P. The gantry 10 includes an X-ray high voltage device 11, an X-ray generator 12, an X-ray detector 13, data acquisition circuitry 14, a rotating frame 15, and a gantry control device 16. Further, as illustrated in FIG. 1, in the gantry 10, an orthogonal coordinate system with the X-axis, the Y-axis, and the Z-axis are defined. That is, the X-axis represents the horizontal direction, the Y-axis represents the vertical direction, and the Z-axis represents an axial direction of the rotation center of the rotating frame 15 observed while the gantry 10 is not tilted.

The rotating frame 15 is an annular frame that supports the X-ray generator 12 and the X-ray detector 13 such that the X-ray generator 12 and the X-ray detector 13 face each other while the subject P is interposed between the X-ray generator 12 and the X-ray detector 13, and that is rotated by the gantry control device 16 (to be described later) at a high speed in a circular orbit centered at the subject P.

The X-ray generator 12 is a device that generates an X-ray and radiates the generated X-ray onto the subject P. The X-ray generator 12 includes an X-ray tube 12a, a wedge 12b, and a collimator 12c.

The X-ray tube 12a is a vacuum tube that receives supply of high voltage from the X-ray high voltage device 11 and emits thermal electrons from the cathode (which may be called a filament) to the anode (a target). The X-ray tube 12a radiates an X-ray beam to the subject P along with rotation of the rotating frame 15. In other words, the X-ray tube 12a generates X-rays by using high voltage supplied from the X-ray high voltage device 11.

Further, the X-ray tube 12a generates an X-ray beam that spreads with a fan angle and a cone angle. For example, under the control of the X-ray high voltage device 11, the X-ray tube 12a is capable of continuously emitting X-rays in the entire surrounding of the subject P to realize full reconstruction, and is capable of continuously emitting X-rays in an emission range (180 degrees+the fan angle) that enables half reconstruction in order to realize half reconstruction. Furthermore, under the control of the X-ray high voltage device 11, the X-ray tube 12a is capable of intermittently emitting X-rays (pulse X-rays) at positions (X-ray tube positions) set in advance. Moreover, the X-ray high voltage device 11 is also capable of modulating the intensities of X-rays emitted from the X-ray tube 12a. For example, the X-ray high voltage device 11 increases the intensities of X-rays emitted from the X-ray tube 12a at a specific X-ray tube position and decreases the intensities of X-rays emitted from the X-ray tube 12a in a range other than the specific X-ray tube position.

The wedge 12b is an X-ray filter configured to adjust the X-ray does of X-rays emitted from the X-ray tube 12a. Specifically, the wedge 12b is a filter that transmits and attenuates X-rays emitted from the X-ray tube 12a such that the X-rays radiated from the X-ray tube 12a to the subject P have a predetermined distribution. For example, the wedge 12b is a filter obtained by processing aluminum so as to have a predetermined target angle and a predetermined thickness. The wedge 12b may be referred to as a wedge filter or a bow-tie filter.

The collimator 12c is configured with a lead plate or the like and has a slit in a part thereof. For example, the collimator 12c narrows down, with use of the slit, the radiation range of the X-rays for which the X-ray dose has been adjusted by the wedge 12b, under the control of the X-ray high voltage device 11.

An X-ray source of the X-ray generator 12 is not limited to the X-ray tube 12a. For example, the X-ray generator 12 may be configured with a focus coil that converges an electron beam generated from an electron gun, a deflection coil that electromagnetically deflects the electron beam, and a target ring that covers a semi circumference of the subject P and generates X-rays by collision with the deflected electron beam.

The X-ray high voltage device 11 is configured with electric circuitry including a transformer, a rectifier, or the like, and includes a high voltage device having a function to generate a high voltage to be applied to the X-ray tube 12a and an X-ray control device that controls an output voltage in accordance with X-rays radiated by the X-ray tube 12a. The high voltage device may be of a transformer type or an inverter type. For example, the X-ray high voltage device 11 adjusts the X-ray dose radiated on the subject P by adjusting the X-ray tube voltage and/or the X-ray tube current supplied to the X-ray tube 12a. Further, the X-ray high voltage device 11 is controlled by processing circuitry 37 of the console 30.

The gantry control device 16 is configured with processing circuitry that is configured with a central processing unit (CPU) or the like, and a driving mechanism, such as a motor or an actuator. The gantry control device 16 has a function to receive an input signal from either an input interface 31 attached to the console 30 or an input interface attached to the gantry 10, and control operation of the gantry 10. For example, the gantry control device 16 causes the X-ray tube 12a and the X-ray detector 13 to revolve in a circular orbit centered at the subject P, causes the gantry 10 to tilt, and causes the couch 20 and a couchtop 22 to move, by rotating the rotating frame 15 upon receiving an input signal. The gantry control device 16 is controlled by the processing circuitry 37 of the console 30.

Further, the gantry control device 16 monitors the position of the X-ray tube 12a, and outputs a view trigger signal indicating a timing to start data acquisition to the data acquisition circuitry 14 when the X-ray tube 12a reaches a predetermined rotation angle (imaging angle). For example, when the total number of views in rotational imaging is 2460 views, the gantry control device 16 outputs the view trigger signal every time the X-ray tube 12a is moved by about 0.15 degree (=360/2460) in the circular orbit.

Figure 2:
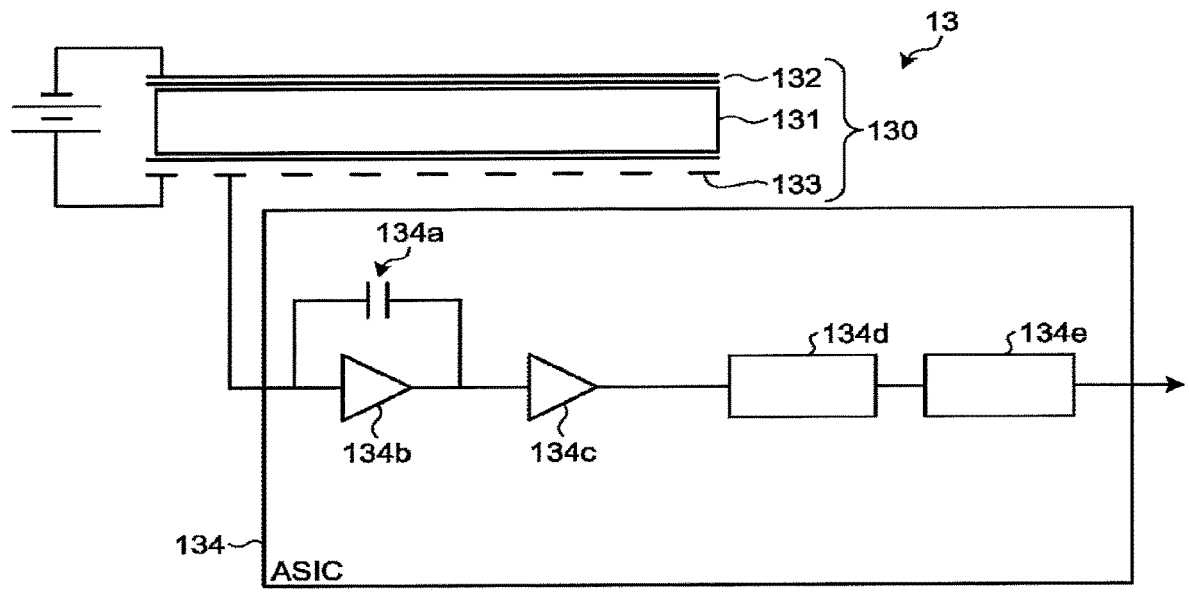
FIG. 2 is a diagram for explaining an X-ray detector according to the first embodiment.

The X-ray detector 13 is an example of a photon counting detector that includes a plurality of detecting elements and outputs signals corresponding to the number of photons that are counted. For example, the X-ray detector 13 is configured with a plurality of arrays of X-ray detecting elements (which may be referred to as "sensors" or simply "detecting elements"), where each of the arrays includes a plurality of X-ray detecting elements arranged in a channel direction along one arc centered at a focal point of the X-ray tube 12a. The X-ray detector 13 has a structure in which the plurality of arrays of X-ray detecting elements are arranged in a slice direction, where each of the arrays of X-ray detecting elements includes the plurality of X-ray detecting elements that are arranged in the channel direction. Each of the X-ray detecting elements included in the X-ray detector 13 is configured to detect X-rays that have been emitted from the X-ray generator 12 and have passed through the subject P and to output an electrical signal (a pulse) corresponding to the X-ray dose to the data acquisition circuitry 14. The electrical signal output by each of the X-ray detecting elements may also be referred to as a detection signal. FIG. 2 is a diagram for explaining the X-ray detector 13 according to the first embodiment.

As illustrated in FIG. 2, the X-ray detector 13 is a photon counting detector that includes a plurality of detecting units, each of which includes a detecting element 130 that detects X-ray photons and an application specific integrated circuit (ASIC) 134 that is connected to the detecting element 130 and counts the X-ray photons detected by the detecting element 130. In the example in FIG. 2, one of the detecting units is illustrated. The detecting unit is one example of detection circuitry. In the following, a case will be described in which the X-ray detector 13 is a detector of a direct conversion type.

Each of the detecting elements 130 includes a semiconductor 131, a cathode electrode 132, and a plurality of anode electrodes 133. Here, the semiconductor 131 is a semiconductor made of cadmium telluride (CdTe), cadmium zinc telluride (CZT), or the like. Further, each of the plurality of anode electrodes 133 corresponds to an individual detection pixel (also referred to as a "pixel"). When X-ray photons are incident on the detecting element 130, the X-rays incident on the detecting element 130 are directly converted to electric charges and the electric charges are output to the ASIC 134.

While a case will be described below in which the X-ray detector 13 is a semiconductor detector of a direct conversion type, possible embodiments are not limited to this example. For example, the X-ray detector 13 may be a detector of an indirect conversion type configured with a grid, a scintillator array, and a photo sensor array. The scintillator array is configured with a plurality of scintillators, each of which is configured with a scintillator crystal that outputs a certain amount of light corresponding to incident X-ray energy. The grid is disposed on the surface of the scintillator array on an X-ray incident side and is configured with an X-ray blocking plate having a function to absorb scattered X-rays. The photo sensor array has a function to convert light into electrical signals corresponding to the amount of light output from the scintillator, and is configured with photo sensors, such as photomultipliers, for example. Here, the photo sensors are photodiodes (PDs), avalanche photodiodes (APDs), silicon photomultipliers (SiPMs), or the like.

The ASIC 134 discriminates individual electric charges output from the detecting element 130, and counts the number of X-ray photons incident on the detecting element 130. Further, the ASIC 134 performs arithmetic processing that is based on magnitudes of individual electric charges, and measures energy of the counted X-ray photons. The ASIC 134 includes a capacitor 134a, amplification circuitry 134b, waveform shaping circuitry 134c, comparator circuitry 134d, and a counter 134e, for example. The ASIC 134 is one example of counting circuitry.

The capacitor 134a accumulates the electric charges output from the detecting element 130. The amplification circuitry 134b is circuitry that integrates and amplifies the electric charges accumulated in the capacitor 134a and outputs a pulse signal corresponding to the electric quantity, in response to the X-ray photons incident on the detecting element 130. The wave height or the area of the pulse signal is correlated with energy of photons.

Incidentally, the amplification circuitry 134b includes, for example, an amplifier. The amplifier is a single-ended amplifier, for example. When the amplifier is the single-ended amplifier, the amplifier is grounded and amplifies a potential difference between the grounding potential (ground) and a potential indicated by an electrical signal output by the detecting element 130. The amplification may be a differential amplifier. When the amplifier is the differential amplifier, positive input (+) of the amplifier is connected to the detecting element 130 and the negative input (−) is grounded. The differential amplifier amplifies a potential difference between a potential indicated by an electrical signal that is input to the positive input from the detecting element 130 and the grounding potential indicated by an electrical signal input to the negative input.

In the ASIC 134, a processing time ($\tau$(ns)) is set in the amplification circuitry 134b. Here, the processing time indicates an integral time in the amplification circuitry 134b. In other words, the processing time of each of the ASICs 134 is determined by the integral time in each of the ASICs 134. Further, the processing time is one example of a control parameter of the ASIC 134. Furthermore, white noise occurs in the ASIC 134.

The waveform shaping circuitry 134c is circuitry that adjusts the frequency characteristic of a pulse signal output from the amplification circuitry 134b and shapes the waveform of the pulse signal by giving gain and offset.

The comparator circuitry 134d is circuitry that compares the wave height or the area of a response pulse signal that is obtained in response to the incident photons, with thresholds that are set in advance in accordance with a plurality of energy bands that need to be discriminated, and outputs results of the comparison with the thresholds to the counter 134e.

The counter 134e counts a discrimination result of the waveform of the response pulse signal for each corresponding energy band, and outputs a count result of photons as digital data to the data acquisition circuitry 14.

The data acquisition circuitry 14 (data acquisition system (DAS)) is circuitry that acquires a result of a counting process from each of the detecting elements 130 of the X-ray detector 13, and generates detection data. In other words, the data acquisition circuitry 14 acquires a count result obtained by the X-ray detector 13. Here, the detection data is, for example, a sinogram. The sinogram is data in which results of the counting processes are arranged side by side, where the results indicate the counts of incidences on the detecting elements 130 at different positions of the X-ray tube 12a. The data acquisition circuitry 14 acquires results of the counting processes at different view angles from the X-ray detector 13 in synchronization with view trigger signals, and generates a sinogram. The data acquisition circuitry 14 repeats one of a process of outputting the results of the counting processes at predetermined intervals (for each view) and a process of storing the results of the counting processes in storage circuitry 35, and repeats a process of resetting the results of the counting processes, to thereby acquire data of needed cycles.

Figure 3:
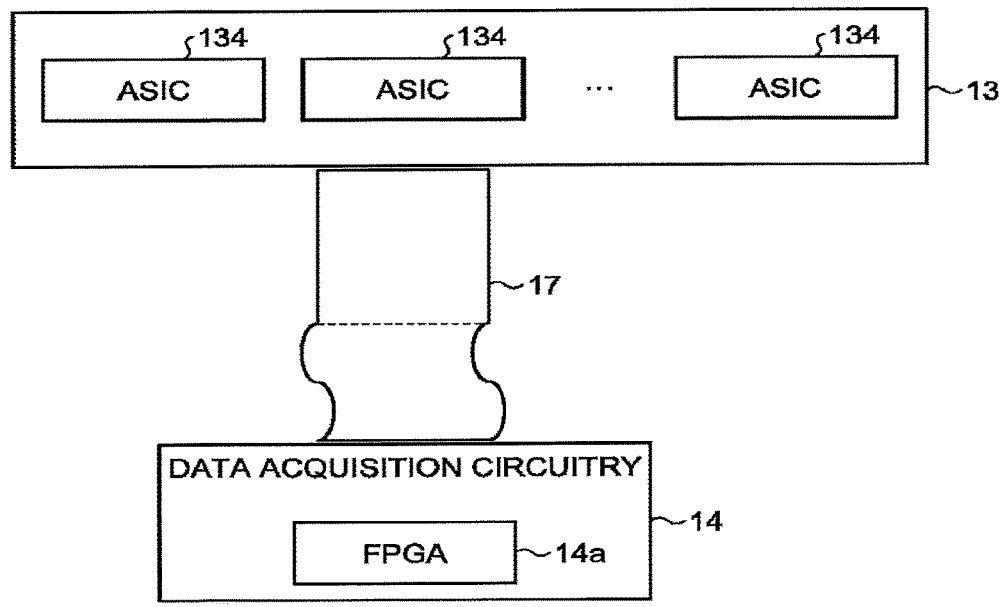
FIG. 3 is a diagram for explaining data acquisition circuitry according to the first embodiment.

Further, the data acquisition circuitry 14 transmits various control signals to the X-ray detector 13. FIG. 3 is a diagram for explaining the data acquisition circuitry 14 according to the first embodiment. As illustrated in FIG. 3, the data acquisition circuitry 14 includes a field programmable gate array (FPGA) 14a. Further, as illustrated in FIG. 3, the data acquisition circuitry 14 is connected to the X-ray detector 13 by a rigid flexible board 17, for example. The rigid flexible board 17 is a substrate, in which a rigid wiring board portion having rigidity and strength for mounting components and a flexible wiring board that is foldable are integrated. The FPGA 14a receives a view trigger signal from the gantry control device 16, and controls the X-ray detector 13 based on the received view trigger signal, for example. The data acquisition circuitry 14 is one example of acquisition circuitry, and the FPGA 14a is one example of first processing circuitry.

Data output from the data acquisition circuitry 14 will be referred to as detection data, and data obtained by performing a pre-processing process, such as a logarithmic transformation process, an offset correction process, a sensitivity correction process between channels, a gain correction process between channels, a pile-up correction process, a response function correction process, or a beam hardening correction process, on the detection data will be referred to as raw data. Further, the detection data and the raw data will be collectively referred to as projection data.

The couch 20 is a device for placing and moving the subject P to be scanned. The couch 20 includes a couch driving device 21, the couchtop 22, a pedestal 23, and a base (support frame) 24.

The couchtop 22 is a board on which the subject P is placed. The base 24 supports the couchtop 22. The pedestal 23 is a casing that supports the base 24 such that the base 24 can move in the vertical direction. The couch driving device 21 is a motor or an actuator that moves the couchtop 22 on which the subject P is placed, in the longitudinal direction of the couchtop 22 so as to move the subject P into the rotating frame 15. The couch driving device 21 is also capable of moving the couchtop 22 in the X-axis direction.

As for the method of moving the couchtop 22, only the couchtop 22 may be moved, or the couch 20 may be moved together with the base 24. Further, in a case of upright CT, it may be possible to move a subject moving mechanism that corresponds to the couchtop 22.

The gantry 10 performs helical scan for helically scanning the subject P by rotating the rotating frame 15 while moving the couchtop 22, for example. Alternatively, the gantry 10 performs conventional scan for scanning the subject P in a circular orbit by rotating the rotating frame 15 after moving the couchtop 22 and fixing the position of the subject P. In the embodiments described below, an example will be described in which the relative position between the gantry 10 and the couchtop 22 can be changed by controlling the couchtop 22; however, possible embodiments are not limited to this example. For example, when the gantry 10 is self-propelled, the relative position between the gantry 10 and the couchtop 22 may be changed by controlling the self-propelled movement of the gantry 10. Alternatively, the relative position between the gantry 10 and the couchtop 22 may be changed by controlling the movement of the gantry 10 and the couchtop 22.

The console 30 is a device that receives operation performed by an operator on the X-ray CT apparatus 1 and reconstructs X-ray CT image data by using the count results acquired by the gantry 10. As illustrated in FIG. 1, the console 30 includes the input interface 31, a display 32, the storage circuitry 35, and the processing circuitry 37.

The input interface 31 receives various kinds of input operation from the operator, converts the received input operation into an electrical signal, and outputs the electrical signal to the processing circuitry 37. For example, the input interface 31 receives, from the operator, an acquisition condition used when projection data is acquired, a reconstruction condition used when a CT image is reconstructed, an image processing condition used when a post-processing image is generated from the CT image, or the like. For example, the input interface 31 is realized by a mouse, a keyboard, a trackball, a switch, a button, a joystick, or the like.

The display 32 displays various kinds of information. For example, the display 32 outputs a medical image (CT image) generated by the processing circuitry 37, a graphical user interface (GUI) for receiving various kinds of operation from the operator, or the like. For example, the display 32 is configured with a liquid crystal display, a cathode ray tube (CRT) display, or the like.

The storage circuitry 35 is realized by a semiconductor memory device, such as a random access memory (RAM) or a flash memory, a hard disk, an optical disk, or the like. The storage circuitry 35 stores therein projection data or reconstructed image data, for example.

The processing circuitry 37 executes, for example, a system control function 371, a pre-processing function 372, a reconstruction processing function 373, an image processing function 374, a scan control function 375, a display control function 376, and a determination function 377. Here, processing functions executed by the components of the processing circuitry 37 illustrated in FIG. 1, that is, processing functions executed by the system control function 371, the pre-processing function 372, the reconstruction processing function 373, the image processing function 374, the scan control function 375, the display control function 376, and the determination function 377, are stored in the storage circuitry 35 in the form of computer-executable programs, for example. The processing circuitry 37 is, for example, a processor, and configured to read the plurality of programs from the storage circuitry 35 and execute the read programs to thereby implement functions corresponding to the programs. In other words, the processing circuitry 37 that has read the programs has the functions that are included in the processing circuitry 37 in FIG. 1. The processing circuitry 37 is one example of second processing circuitry.

The system control function 371 controls various functions of the processing circuitry 37 on the basis of input operation received from the operator via the input interface 31.

The pre-processing function 372 generates raw data by performing a pre-processing process, such as a logarithmic transformation process, an offset correction process, a sensitivity correction process between channels, a gain correction process between channels, a pile-up correction process, a response function correction process, or a beam hardening correction process, on the detection data output from the data acquisition circuitry 14.

The reconstruction processing function 373 generates X-ray CT image data by performing a reconstruction process using a filter correction back projection method or a successive approximation reconstruction method on the projection data generated by the pre-processing function 372. The reconstruction processing function 373 stores the reconstructed X-ray CT image data in the storage circuitry 35. In this situation, X-ray CT image data that is reconstructed from data including total energy information by adding pieces of information on all of bins for each of pixels may be referred to as a "base image".

Here, projection data that is generated from the count results obtained by the photon counting CT includes information on energy of X-rays that were attenuated as a result of passing through the subject P. Therefore, the reconstruction processing function 373 is able to reconstruct X-ray CT image data of a specific energy component, for example. Further, the reconstruction processing function 373 is able to reconstruct X-ray CT image data for each of energy components, for example.

Furthermore, the reconstruction processing function 373 assigns color tone corresponding to an energy component to each of pixels of the X-ray CT image data of each of energy components, and generates image data in which the plurality of pieces of X-ray CT image data that are color-coded in accordance with the energy components are superimposed on one another. Moreover, the reconstruction processing function 373 is able to generate image data, with which materials can be identified, by using the k-absorption edge unique to each material. Other examples of image data generated by the reconstruction processing function 373 include monochrome X-ray image data, density image data, and effective atomic number image data.

Furthermore, as an application of X-ray CT, there is a known technique for discriminating types, abundances, density levels, or the like of materials contained in the subject P by using the fact that the X-ray absorption characteristics are different among different materials. This technique is called material decomposition. For example, the reconstruction processing function 373 performs material decomposition on the projection data and obtains material decomposition information. Then, the reconstruction processing function 373 reconstructs a material decomposition image by using the material decomposition information that is a result of the material decomposition.

In a case of reconstructing the CT image, the reconstruction processing function 373 is able to apply a full-scan reconstruction scheme and a half-scan reconstruction scheme. For example, when using the full-scan reconstruction scheme, the reconstruction processing function 373 needs projection data from the entire surrounding of the subject corresponding to 360 degrees. In contrast, when using the half-scan reconstruction scheme, the reconstruction processing function 373 needs projection data corresponding to 180 degrees+a fan angle. Hereinafter, for simplicity of explanation, it is assumed that the reconstruction processing function 373 uses the full-scan reconstruction scheme in which the reconstruction is performed by using projection data from the entire surrounding of the subject corresponding to 360 degrees.

The image processing function 374 converts the X-ray CT image data generated by the reconstruction processing function 373 to image data of a tomographic image on an arbitrary cross-sectional plane or a three-dimensional image resulting from a rendering process, by using any of well-known methods on the basis of input operation received from the operator via the input interface 31. The image processing function 374 stores the converted image data in the storage circuitry 35.

The scan control function 375 controls CT scan performed by the gantry 10. For example, the scan control function 375 controls start of scan, execution of scan, and termination of scan performed by the gantry 10, by controlling operation of the X-ray high voltage device 11, the X-ray detector 13, the gantry control device 16, the data acquisition circuitry 14, and the couch driving device 21. Specifically, the scan control function 375 controls a projection data acquisition process in an imaging process of acquiring a position determination image (a scanogram image or a scanogram) and a main imaging process (scan) of acquiring an image used for diagnosis.

Here, the scan control function 375 can capture a two-dimensional scanogram image and a three-dimensional scanogram image. For example, the scan control function 375 captures a two-dimensional scanogram image by continuously performing imaging by moving the couchtop 22 at a constant speed while fixing the X-ray tube 12a at a position of 0 degree (a position in the front direction of the subject P). Alternatively, the scan control function 375 captures a two-dimensional scanogram image by intermittently repeating imaging in synchronization with movement of the couchtop 22 by intermittently moving the couchtop 22 while fixing the X-ray tube 12a at the position of 0 degree. Further, the scan control function 375 is able to capture the position determination image not only from the front direction but also from any direction (for example, a side direction). For example, when imaging is performed while the X-ray tube 12a is located at a position of 90 degrees (a position in the side direction of the subject P), the imaging is performed from the side of the subject P and a two-dimensional scanogram image is obtained. As for the position of the X-ray tube 12a, it is possible to perform imaging from a plurality of arbitrary positions if needed.

Further, in capturing a scanogram image, the scan control function 375 captures a three-dimensional scanogram image by acquiring projection data from the entire surrounding of a subject. For example, the scan control function 375 acquires the projection data from the entire surrounding of the subject through helical scan or non-helical scan. In this case, the scan control function 375 performs the helical scan or the non-helical scan with lower radiation does than the main imaging process, with respect to the wide area, such as the entire chest, the entire abdomen, the entire upper body, the whole body, or the like. As the non-helical scan, for example, step-and-shoot scan is performed.

The display control function 376 causes the display 32 to display various kinds of image data stored in the storage circuitry 35.

The determination function 377 determines a processing time corresponding to the position of each of the detecting elements 130 in the X-ray detector 13. Details of the determination function 377 will be described later.

An exemplary configuration of the X-ray CT apparatus 1 according to the first embodiment has been explained. The X-ray CT apparatus 1 according to the first embodiment configured as described above integrates output signals (electric charges) output from the X-ray detector 13 and performs waveform shaping, and, thereafter, sets a plurality of divided windows in accordance with signal levels and counts the number of incident X-rays for each of the windows by using a counter. The X-ray CT apparatus 1 acquires data of needed cycles, and acquires CT images with a plurality of energy windows. A processing time of an output signal (electric charge) is determined by a processing time that is set in the ASIC 134.

Figure 4:
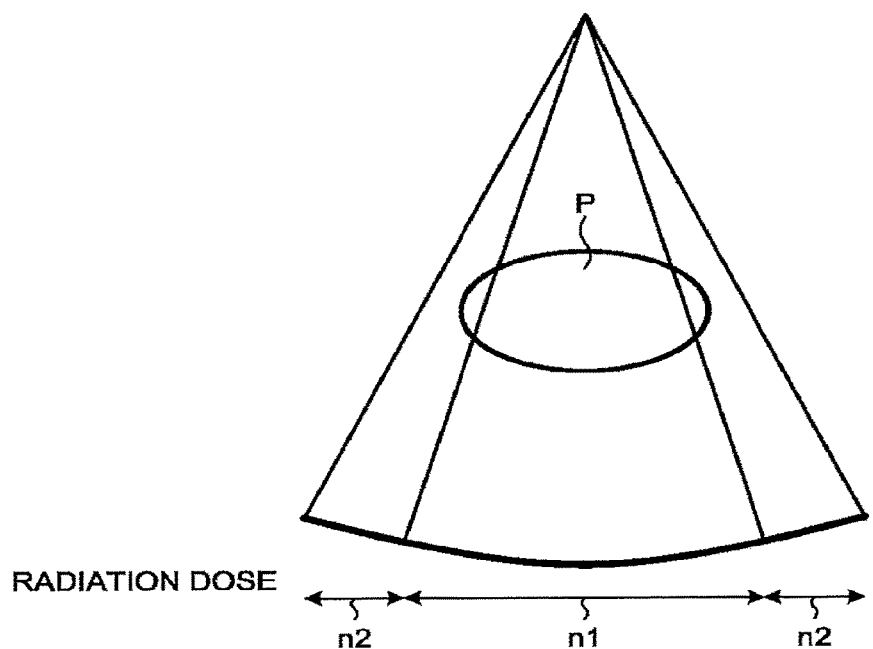
FIG. 4 is a diagram for explaining a comparative example.
Figure 5:
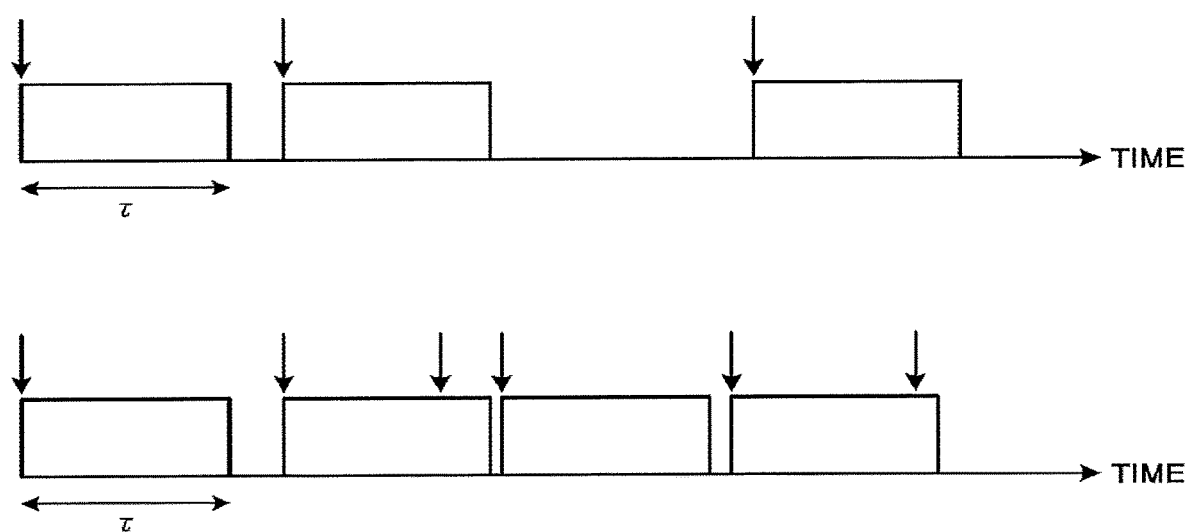
FIG. 5 is a diagram for explaining a comparative example.

Here, as a comparative example, a case will be described in which the processing time of each of the ASICs 134 in the X-ray detector 13 is set to a constant value. That is, in the comparative example, it is assumed that the processing times of all of the ASICs 134 are set to the same value. With reference to FIG. 4 and FIG. 5, a problem with the comparative example will be described. FIG. 4 and FIG. 5 are diagrams for explaining the comparative example.

In the X-ray detector 13, the X-ray dose incident on each of the detecting elements 130 is different depending on the position in the X-ray detector 13. For example, as illustrated in FIG. 4, in a central portion of the X-ray detector 13, the amount of absorption by the subject P is large, so that the X-ray dose incident on the detecting element 130 is reduced. Here, it is assumed that the X-ray dose in this case is denoted by n1 (count/sec), for simplicity of explanation. In contrast, in edge portions of the X-ray detector 13, the amount of absorption by the subject P is small or zero, so that the X-ray dose incident on the detecting element 130 is increased. Here, it is assumed that the X-ray dose in this case is denoted by n2 (count/sec), for simplicity of explanation. The central portion of the X-ray detector 13 indicates a region around the center in the channel direction of the X-ray detector 13, and the edge portions of the X-ray detector 13 indicate edge regions distant from the center in the channel direction of the X-ray detector 13.

The upper diagram in FIG. 5 indicates a timing of X-ray incidence in a case where the X-ray dose is set to n1, and the lower diagram in FIG. 5 indicates a timing of X-ray incidence in a case where the X-ray dose is set to n2. Further, in FIG. 5, the processing time is set to t (ns). As illustrated in the upper diagram in FIG. 5, when the incident X-ray dose is low, the number of incident X-rays in each of the processing times is equal to or smaller than 1. In this manner, when the incident X-ray dose is low, pile-up can hardly occur.

In contrast, as illustrated in the lower diagram in FIG. 5, when the incident X-ray dose is high, the number of incident X-rays in each of the processing times becomes equal to or larger than 2 in some cases. In other words, when the number of X-ray photons incident on the X-ray detector 13 is large, a phenomenon called pile-up, in which another X-ray is incident on the X-ray detector 13 during the same processing time, may continuously occur. If pile-up occurs, the count number of the X-ray photons and the energy value of the detected X-rays are deviated from correct values, so that image quality to be eventually obtained will be deteriorated. For example, when a single X-ray photon at 60 KeV and a single X-ray photon at 80 Key are incident on the X-ray detector 13 during a certain processing time, the X-ray detector 13 performs counting such that a single X-ray photon at 140 KeV is incident on the X-ray detector 13.

To cope with this situation, it may be possible to reduce the influence of pile-up by reducing the processing time as much as possible in order to obtain high image quality. However, if the processing time is reduced, for example, since sufficient charge integration cannot be performed in the amplification circuitry 134b, the measurement result of the above-described X-ray energy value becomes inaccurate, and eventually the material decomposition capability is reduced.

In contrast, if the processing time is increased, the material decomposition capability of the detecting element 130 disposed in the central portion in the channel direction in the X-ray detector 13 is improved, but pile-up occurs and image quality is deteriorated in the detecting element 130 disposed in the edge portions in the channel direction in the X-ray detector 13. In this manner, in the comparative example, it is difficult to realize both of high image quality and high material decomposition capability.

To cope with this situation, the X-ray CT apparatus 1 according to the first embodiment sets a processing time corresponding to the position of each of the detecting elements 130 in the photon counting detector, in the ASIC 134 connected to each of the detecting elements 130 at the time of imaging. In the following, the first embodiment will be described with reference to FIG. 6 to FIG. 9. FIG. 6 is a flowchart illustrating the flow of a process performed by the X-ray CT apparatus 1 according to the first embodiment, and FIG. 7 to FIG. 9 are diagrams for explaining the first embodiment.

FIG. 6 illustrates the flowchart for explaining operation performed by the X-ray CT apparatus 1, and correspondence between the steps and the components will be described below. Step S1 is a step corresponding to the scan control function 375. Step S1 is a step at which the processing circuitry 37 calls and executes a predetermined program corresponding to the scan control function 375 from the storage circuitry 35, and the scan control function 375 is implemented. At Step S1, the scan control function 375 captures a scanogram. For example, the scan control function 375 fixes the X-ray tube 12a at the position of 0 degree (a position in the front direction of the subject P), and captures a two-dimensional scanogram image.

Step S2 is a step corresponding to the determination function 377. Step S2 is a step at which the processing circuitry 37 calls and executes a predetermined program corresponding to the determination function 377 from the storage circuitry 35, and the determination function 377 is implemented. At Step S2, the determination function 377 determines a processing time.

Here, the determination function 377 determines the processing time based on an X-ray dose incident on each of the detecting elements 130, and generates correspondence information. For example, the determination function 377 estimates the X-ray dose incident on each of the detecting elements 130 from a count result obtained by each of the detecting elements 130, and determines the processing time based on the estimated X-ray dose. As one example, the determination function 377 estimates the X-ray dose incident on each of the detecting elements 130 from a count result of scanograms captured at Step S1, and determines the processing time.

The determination function 377 determines the processing time by performing a threshold determination process on the count result of the scanograms as described below. For example, the determination function 377 estimates that the X-ray dose incident on the detecting element 130 is high in a certain region, in which the count result of the scanograms is equal to or larger than a threshold, in the channel direction, and selects this region as a high-dose region. Then, the determination function 377 reduces the processing time of the ASIC 134 connected to the detecting element corresponding to the high-dose region. In contrast, the determination function 377 estimates that the X-ray dose incident on the detecting element 130 is low in a certain region, in which the count result of the scanograms is smaller than the threshold, in the channel direction, and selects this region as a low-dose region. Then, the determination function 377 increases the processing time of the ASIC 134 connected to the detecting element corresponding to the low-dose region.

More specifically, the incident X-ray dose is reduced in the central portion in the channel direction because the amount of absorption by the subject P is large. Therefore, as illustrated in FIG. 7, the determination function 377 selects the central portion in the channel direction as the low-dose region, and increases the processing time of the central portion in the channel direction. Further, the incident X-ray dose is increased in the edge portions in the channel direction because the amount of absorption by the subject P is small or zero. Therefore, as illustrated in FIG. 7, the determination function 377 selects the edge portions in the channel direction as the high-dose regions, and reduces the processing times of the edge portions in the channel direction.

The determination function 377 may determine the processing time by performing the threshold determination process on a representative slice, and apply the determined processing time to the other slices in the same manner. Alternatively, the determination function 377 may determine the processing time by performing the threshold determination process in each of the slice directions. The representative slice is, for example, a central slice in the slice direction.

Then, the determination function 377 generates correspondence information, in which each of the detecting elements and the processing time of the ASIC 134 connected to each of the detecting elements are associated with each other. More specifically, as illustrated in FIG. 8, the determination function 377 generates correspondence information, in which an ID and a processing time are associated with each other.

The "ID" in the correspondence information indicates an identifier for uniquely identifying the detecting element, and the "processing time" indicates a processing time of the ASIC 134 connected to the detecting element identified by the ID. Further, in the example illustrated in FIG. 8, it is assumed that a processing time T1<a processing time T2, the detecting elements 130 with the "IDs" of "yyyy" and "zzzz" are disposed in the high-dose regions that are the edge portions in the channel direction in the X-ray detector 13, and the detecting element 130 with the "ID" of "xxxx" is arranged in the low-dose region that is the central portion in the channel direction in the X-ray detector 13. As one example, the determination function 377 determines that the processing times of the ASICs 134 connected to the detecting elements 130 with the "IDs" of "yyyy" and "zzzz" are "T1", and determines that the processing time of the ASIC 134 connected to the detecting element 130 with the "ID" of "xxxx" is "T2".

Step S3 is a step implemented by the FPGA 14a. At Step S3, the FPGA 14a sets a processing time. Here, the FPGA 14a sets the processing time corresponding to the position of each of the detecting elements 130 in the photon counting detector, in the ASIC 134 connected to each of the detecting elements 130 at the time of imaging. For example, the FPGA 14a sets, in each of the ASICs 134, the processing time that is based on the X-ray dose incident on each of the detecting elements 130.

As one example, the FPGA 14a sets the processing time in each of the ASICs 134 by referring to the correspondence information illustrated in FIG. 8. In other words, the FPGA 14a sets, in each of the ASICs 134, the processing time that is based on the X-ray dose incident on each of the detecting elements 130, where the X-ray dose is estimated from the count result obtained by each of the detecting elements 130. More specifically, the FPGA 14a sets the processing time "T1" in each of the ASICs 134 connected to the detecting elements 130 with the IDs of "yyyy" and "zzzz". Further, the FPGA 14a sets the processing time "T2" in the ASIC 134 connected to the detecting element 130 with the ID of "xxxx". In this manner, the FPGA 14a sets a larger processing time in the ASIC 134 that is connected to the detecting element for which the incident X-ray dose is smaller than the threshold, as compared to the ASIC 134 that is connected to the detecting element for which the incident X-ray dose is equal to or larger than the threshold. In the first embodiment, the processing time that is set in each of the ASICs 134 at the start of imaging is fixed during the imaging.

Step S4 is a step corresponding to the scan control function 375. Step S4 is a step at which the processing circuitry 37 calls and executes a predetermined program corresponding to the scan control function 375 from the storage circuitry 35, and the scan control function 375 is implemented. At Step S4, the scan control function 375 performs main scan.

Step S5 is a step corresponding to the pre-processing function 372. Step S5 is a step at which the processing circuitry 37 calls and executes a predetermined program corresponding to the pre-processing function 372 from the storage circuitry 35, and the pre-processing function 372 is implemented. Meanwhile, detection data obtained through the main scan at Step S4 is a signal obtained through a process that is performed with a different processing time by each of the ASICs 134. Here, if the processing time is changed, a pile-up occurrence rate is also changed. If the pile-up occurrence rate is changed, the count number is reduced and a ratio at which a spectrum is shifted to the high side is changed, for example. In other words, by setting a different processing time, the count number and the spectrum of the detection data are changed. In view of the foregoing situation, at Step S5, the pre-processing function 372 corrects the detection data. In other words, the pre-processing function 372 corrects the count result obtained by the data acquisition circuitry 14.

FIG. 9 illustrates a case in which the count number of the detection data is corrected. In FIG. 9, the horizontal axis represents a tube current value (mA), and the vertical axis represents the number of detected X-rays. Here, in theory, the X-ray irradiation dose and the number of detected X-rays have a linear relationship. For example, as indicated by T0 in FIG. 9, the number of detected X-rays increases with an increase in the X-ray irradiation dose. However, in actual measurement, a non-linear relationship is obtained, in which the number of detected X-rays reaches a peak with an increase in the irradiation dose. The irradiation dose with which the number of detected X-rays reaches the peak is determined depending on the processing time. For example, the number of detected X-rays is reduced with an increase in the processing time. In view of the foregoing situations, the pre-processing function 372 identifies the processing time set in each of the ASICs 134, and corrects the number of X-rays that is the count result obtained in each of the ASICs 134. In the following, it is assumed that the processing time T1<the processing time T2, and the numbers of detected X-rays with respect to the X-ray irradiation dose are measured in advance during the processing time T1 and the processing time T2.

For example, in the example illustrated in FIG. 9, in a case where the number of detected X-rays is C1 and the processing time is T1, the pre-processing function 372 corrects the number of detected X-rays from C1 to C2. Further, in the example illustrated in FIG. 9, in a case where the number of detected X-rays is C1 and the processing time is T2, the pre-processing function 372 corrects the number of detected X-rays from C1 to C3.

Step S6 is a step corresponding to the reconstruction processing function 373. Step S6 is a step at which the processing circuitry 37 calls and executes a predetermined program corresponding to the reconstruction processing function 373 from the storage circuitry 35, and the reconstruction processing function 373 is implemented. At Step S6, the reconstruction processing function 373 reconstructs an image. For example, the reconstruction processing function 373 generates a base image based on the projection data that is obtained by performing a pre-processing process on the detection data that is corrected by the pre-processing function 372 at Step S5. In other words, the reconstruction processing function 373 reconstructs the image based on the corrected count result.

Step S7 is a step corresponding to the display control function 376. Step S7 is a step at which the processing circuitry 37 calls and executes a predetermined program corresponding to the display control function 376 from the storage circuitry 35, and the display control function 376 is implemented. At Step S7, the display control function 376 displays an image on the display 32.

As described above, the X-ray CT apparatus 1 according to the first embodiment sets the processing time corresponding to the position of each of the detecting elements 130 in the X-ray detector 13, in the ASIC 134 connected to each of the detecting elements at the time of imaging. For example, the X-ray CT apparatus 1 sets a larger processing time in the ASIC 134 that is connected to the detecting element 130 disposed in the low-dose region that is the central portion in the channel direction in the X-ray detector 13, as compared to the ASICs 134 that are connected to the detecting elements 130 disposed in the high-dose regions that are the edge portions in the channel direction.

With this configuration, in the central portion of the X-ray detector 13 in the channel direction, the processing time is increased, so that the S/N ratio is improved and the material decomposition capability is improved, for example. In contrast, in the edge portions of the X-ray detector 13 in the channel direction, the processing time is reduced and the influence of pile-up is reduced even under the high-dose condition, so that the histogram is less deformed and an approximately correct counting rate can be obtained. Further, it is less necessary to perform material decomposition in the high-dose regions that are the edge portions of the X-ray detector 13 in the channel direction, and a region where the material decomposition capability is needed is the low-dose region that is the central portion of the X-ray detector 13 in the channel direction. Therefore, according to the X-ray CT apparatus 1 of the first embodiment, it is possible to obtain high image quality and high material decomposition capability.

In the low-dose region, the processing time is increased; however, because the radiation dose is low, it is possible to neglect deformation of the histogram and an influence on a count rate due to pile-up. Further, in the high-dose region, the processing time is reduced, and the S/N ratio is reduced accordingly; however, the count rate is not influenced and an influence on the image quality may be excluded. Therefore, in the X-ray CT apparatus 1 according to the first embodiment, it is possible to omit the above-described correction process performed by the pre-processing function 372.

Furthermore, the reconstruction processing function 373 may perform material decomposition on the projection data, and reconstruct a material decomposition image using material decomposition information that is a result of the material decomposition. In this case, to reconstruct the material decomposition image, it is necessary to perform a process of correcting the spectrum of the detection data, in addition to the process of correcting the count number of the detection data. Hereinafter, the process of correcting the spectrum of the detection data performed by the reconstruction processing function 373 will be described.

A relationship between a spectrum S(E) of an X-ray detected by the X-ray detector 13 and a spectrum $S_0(E)$ of an X-ray incident on the X-ray detector 13 is represented by Equation (1) below using a response function R (E, nτ).

$$S(E) = \{S_0(E)\exp(-\mu L)\} \times R(E, n\tau) \quad (1)$$

Here, $S_0(E)$ is the spectrum of the X-ray applied to the subject P, μ is an average attenuation coefficient of a subject path, and L is a projected length of the subject path. Further, the response function R (E, nτ) includes the X-ray dose n and the processing time τ. A plurality of response functions R are set by the X-ray dose n and the processing time τ. Here, the spectrum S(E) of the X-ray, the spectrum $S_0(E)$ of the X-ray applied to the subject P, and the response function R (E, nτ) are already known. Therefore, the reconstruction processing function 373 is able to calculate the amount of absorption (-μL) from Equation (1). In other words, the reconstruction processing function 373 is able to perform material decomposition by additionally taking into account a change in the spectrum of the detection data caused by a difference in the processing time. In a case where the base image is generated, it is sufficient to correct the count number of the detection data, and it is not necessary to correct a difference in the spectrum that occurs in the detection data.

Modification of First Embodiment

Figures 10, 11:
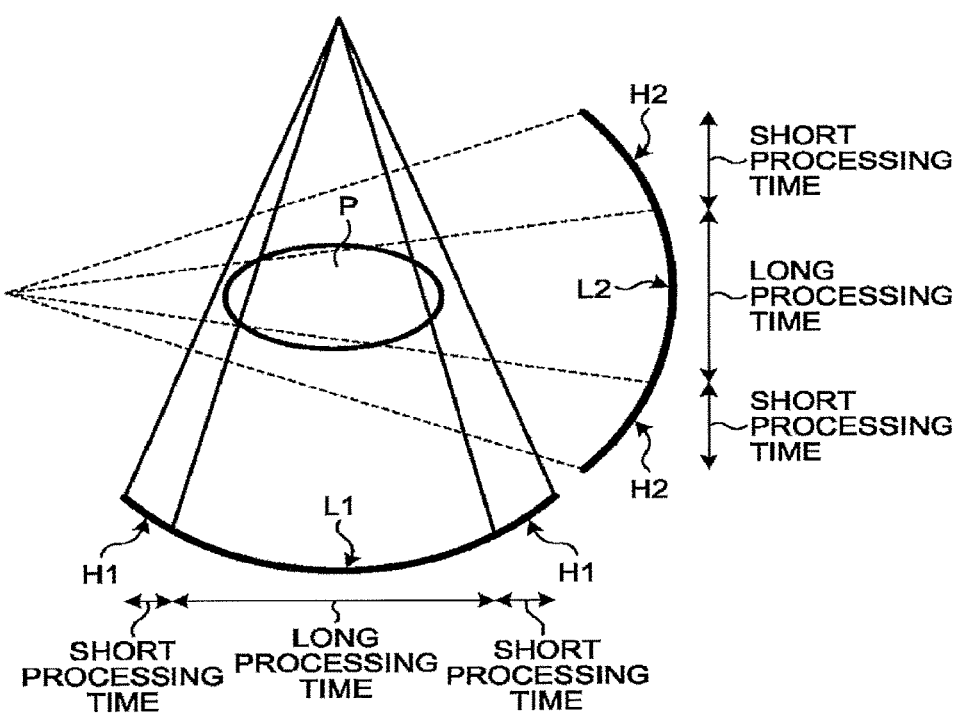
FIG. 10 is a diagram for explaining a modification of the first embodiment.
FIG. 11 is a diagram for explaining a second embodiment.

In the first embodiment described above, the example has been described in which the material decomposition is performed using a response function in which the processing time is taken into account; however, possible embodiments are not limited to this example. For example, it may be possible to perform material decomposition using a lookup table. In this case, the lookup table stores a detection spectrum that is determined in advance in accordance with the projected length of each of materials to be identified by the material decomposition. Further, a plurality of lookup tables are generated in advance under imaging conditions in which a tube current and a tube voltage are changed in various ways. The reconstruction processing function 373 performs material decomposition by searching for a detection spectrum corresponding to the detection data from the lookup table. FIG. 10 is a diagram for explaining a modification of the first embodiment.

In FIG. 10, an example is illustrated in which water and calcium are identified through material decomposition. As illustrated in FIG. 10, the lookup table stores therein a histogram that is obtained when a thickness of a calcium part is changed to 1, 2, 3, and 4 millimeters (mm) with respect to thicknesses of a water part of 5, 10, 15, and 20 centimeters (cm). As one example, $S(E)_{11}$ represents a histogram that is obtained when the water part is 5 cm and the calcium part is 1 mm, and $S(E)_{21}$ represents a histogram that is obtained when the water part is 5 cm and the calcium part is 2 mm. In this case, the reconstruction processing function 373 performs material decomposition by identifying a histogram that is similar to the detection data by using the lookup table that is generated under an imaging condition in which pile-up is likely to occur, for example.

Second Embodiment

In the first embodiment described above, the example has been described in which the processing time corresponding to the position of each of the detecting elements is set in the ASIC 134 connected to each of the detecting elements at the time of imaging. In the first embodiment, the processing time set in each of the ASICs 134 at the start of imaging is fixed during the imaging.

Incidentally, a cross section of the subject P usually has an elliptical shape rather than a circular shape. Therefore, if the region with a short processing time and the region with a long processing time are fixed as illustrated in FIG. 7, high-dose X-rays may be incident on the region in which a long processing time is set while the X-ray tube 12a revolves once around the subject P, depending on an imaging angle. In this case, the count number may be reduced or the spectrum is shifted to the high side due to pile-up, so that image quality is deteriorated.

To cope with this situation, it may be possible to dynamically change the processing time, which has been set in accordance with the position of each of the detecting elements 130, depending on an imaging angle of the X-ray tube 12a, instead of fixing the processing time during the imaging. Therefore, in a second embodiment, an example will be described in which the processing time is set in each of the ASICs 134 in accordance with the imaging angle.

A configuration of the X-ray CT apparatus 1 according to the second embodiment is the same as the configuration of the X-ray CT apparatus 1 illustrated in FIG. 1 except that some parts of the determination function 377 and the FPGA 14a are different. Therefore, in the second embodiment, only functions executed by the determination function 377 and the FPGA 14a will be described.

The determination function 377 determines a processing time corresponding to an imaging angle, on the basis of an X-ray dose incident on each of the detecting elements 130, and generates correspondence information. For example, the determination function 377 estimates the X-ray dose incident on each of the detecting elements 130 from the count result obtained by each of the detecting elements 130, and determines a processing time that is based on the estimated X-ray dose. As one example, the determination function 377 estimates the X-ray dose incident on each of the detecting elements 130 from the count result of scanograms, and determines the processing time. In the second embodiment, the scan control function 375 captures two-dimensional scanogram images in two directions. For example, the scan control function 375 captures a two-dimensional scanogram image (a scanogram at 0 degree) while fixing the X-ray tube 12a at the position of 0 degree (a position in the front direction of the subject P), and thereafter captures a two-dimensional scanogram image (a scanogram at 90 degrees) while fixing the X-ray tube 12a at the position of 90 degrees (a position in the side direction of the subject P).

The determination function 377 determines the processing time by performing a threshold determination process on the count results of the two-dimensional scanogram images obtained from the two directions. In other words, the determination function 377 estimates the X-ray dose incident on each of the detecting elements using the two-dimensional scanogram images obtained from the two directions, and determines the processing time. FIG. 11 is a diagram for explaining the second embodiment.

For example, as illustrated in FIG. 11, the determination function 377 estimates that the X-ray dose incident on the detecting element 130 is high in a certain region, in which the count result of the scanograms at 0 degree is equal to or larger than a threshold, in the channel direction, and selects this region as a high-dose region H1. Then, as illustrated in FIG. 11, the determination function 377 reduces the processing time of the ASIC 134 connected to the detecting element corresponding to the high-dose region H1. In contrast, as illustrated in FIG. 11, the determination function 377 estimates that the X-ray dose incident on the detecting element 130 is low in a certain region, in which the count result of the scanograms at 0 degree is smaller than the threshold, in the channel direction, and selects this region as a low-dose region L1. Then, as illustrated in FIG. 11, the determination function 377 increases the processing time of the ASIC 134 connected to the detecting element corresponding to the low-dose region L1.

Further, as illustrated in FIG. 11, the determination function 377 estimates that the X-ray dose incident on the detecting element 130 is high in a certain region, in which the count result of the scanograms at 90 degrees is equal to or larger than a threshold, in the channel direction, and selects this region as a high-dose region H2, for example. Then, as illustrated in FIG. 11, the determination function 377 reduces the processing time of the ASIC 134 connected to the detecting element corresponding to the high-dose region H2. In contrast, as illustrated in FIG. 11, the determination function 377 estimates that the X-ray dose incident on the detecting element 130 is low in a certain region, in which the count result of the scanograms at 90 degrees is smaller than the threshold, in the channel direction, and selects this region as a low-dose region L2. Then, as illustrated in FIG. 11, the determination function 377 increases the processing time of the ASIC 134 connected to the detecting element corresponding to the low-dose region L2.

In this manner, when the imaging angle is set to 90 degrees, the determination function 377 selects, as the low-dose region L2, a narrower range than the low-dose region L1 that is adopted while the imaging angle is set to 0 degree. Further, when the imaging angle is set to 90 degrees, the determination function 377 selects, as the high-dose region H2, a wider range than the high-dose region H1 that is adopted while the imaging angle is set to 0 degree.

The determination function 377 may determine the processing time by performing the threshold determination process on a representative slice, and apply the determined processing time to the other slices in the same manner. Alternatively, the determination function 377 may determine the processing time by performing the threshold determination process in each of the slice directions. The representative slice is, for example, a central slice in the slice direction.

Then, the determination function 377 determines the processing time corresponding to each of the detecting elements 130 for each of imaging angles other than 0 degree and 90 degrees. For example, the determination function 377 estimates a shape of the cross section of the subject P in a case where it is assumed that the cross section of the subject P has an elliptical shape, from the positional relationship among the X-ray tube 12a, the subject P, the high-dose region H1, and the low-dose region L1 at the imaging angle of 0 degree, and from the positional relationship among the X-ray tube 12a, the subject P, the high-dose region H2, and the low-dose region L2 at the imaging angle of 90 degrees. Then, the determination function 377 estimates the processing time corresponding to each of the detecting elements 130 for each of the imaging angles by using the estimated shape of the cross section of the subject P. In this manner, the processing time corresponding to each of the detecting elements 130 is determined for each of the imaging angles.

The determination function 377 may determine the processing time corresponding to each of the detecting elements 130 for each of the imaging angles other than 0 degree and 90 degrees, by using the same method as adopted when the imaging angle is set to 0 degree or 90 degrees.

Then, the determination function 377 generates correspondence information, in which each of the detecting elements 130, the imaging angle, and the processing time of the ASIC 134 connected to each of the detecting elements 130 are associated with one another. FIG. 12 is a diagram for explaining the second embodiment. For example, as illustrated in FIG. 12, the determination function 377 generates correspondence information, in which an ID, a view number, and a processing time are associated with one another.

The "ID" in the correspondence information indicates an identifier for uniquely identifying the detecting element. The "view number" indicates an integrated value of view trigger signals received from the gantry control device 16. For example, in the view number, "N1≤N<N2", which indicates a range of the view number such that the view number is equal to or larger than N1 and smaller than N2, or "N2≤N<N3", which indicates a range of the view number such that the view number is equal to or larger than N2 and smaller than N3, is stored. The view number is information corresponding to the imaging angle of the X-ray tube 12a, and is reset every time the X-ray tube 12a revolves once. Further, in this example, it is assumed that the view number of zero is assigned when the X-ray tube 12a is located at the position of 0 degree (a position in the front direction of the subject P), the X-ray tube 12a starts imaging from the position of 0 degree at the start of imaging, and the view number is integrated every time the X-ray tube 12a moves in a circular orbit. The "processing time" indicates a processing time of the ASIC 134 connected to the detecting element identified by the ID, for each corresponding view number. Furthermore, in the example illustrated in FIG. 12, it is assumed that the processing time T1<the processing time T2, the detecting element 130 with the "ID" of "yyyy" is disposed in the high-dose region that is the edge portion in the channel direction in the X-ray detector 13, and the detecting element 130 with the "ID" of "xxxx" is arranged in the low-dose region that is the central portion in the channel direction in the X-ray detector 13. Moreover, it is assumed that the detecting element 130 with the "ID" of "yyyy" is disposed in a region between the central portion and the edge portion in the channel direction in the X-ray detector 13, and may be included in the high-dose region or the low-dose region depending on the imaging angle.

As one example, the determination function 377 determines that the processing time of the ASIC 134 connected to the detecting element 130 with the "ID" of "yyyy" is "T1" regardless of the view number. Further, the determination function 377 determines that the processing time of the ASIC 134 connected to the detecting element 130 with the "ID" of "xxxx" is "T2" regardless of the view number. Furthermore, the determination function 377 determines that the processing time of the ASIC 134 connected to the detecting element 130 with the "ID" of "yyyy" is "T2" when the view number corresponds to "N1≤N<N2", "T1" when the view number corresponds to "N2≤N<N3", "T2" when the view number corresponds to "N3≤N<N4", and "T1" when the view number corresponds to "N4≤N<N1".

The FPGA 14a sets the processing time corresponding to the position of each of the detecting elements 130 in the photon counting detector, in the ASIC 134 connected to each of the detecting elements 130 at the time of imaging. For example, the FPGA 14a sets, in each of the ASICs 134, the processing time that is based on the X-ray dose incident on each of the detecting elements 130.

As one example, the FPGA 14a sets the processing time in each of the ASICs 134 by referring to the correspondence information illustrated in FIG. 12. Here, the FPGA 14a sets, in each of the ASICs 134, the processing time that corresponds to the view number at the start of imaging, for example. In this example, it is assumed that the view number at the start of imaging is N1. The FPGA 14a sets the processing time T1 in the ASIC 134 connected to the detecting element 130 with the ID of "yyyy". Further, the FPGA 14a sets the processing time T2 in the ASIC 134 connected to the detecting element 130 with the ID of "xxxx". In other words, the FPGA 14a sets, in each of the ASICs 134, the processing time that is based on the X-ray dose incident on each of the detecting elements 130, where the X-ray dose is estimated from the count result obtained by each of the detecting elements 130.

Figure 13:
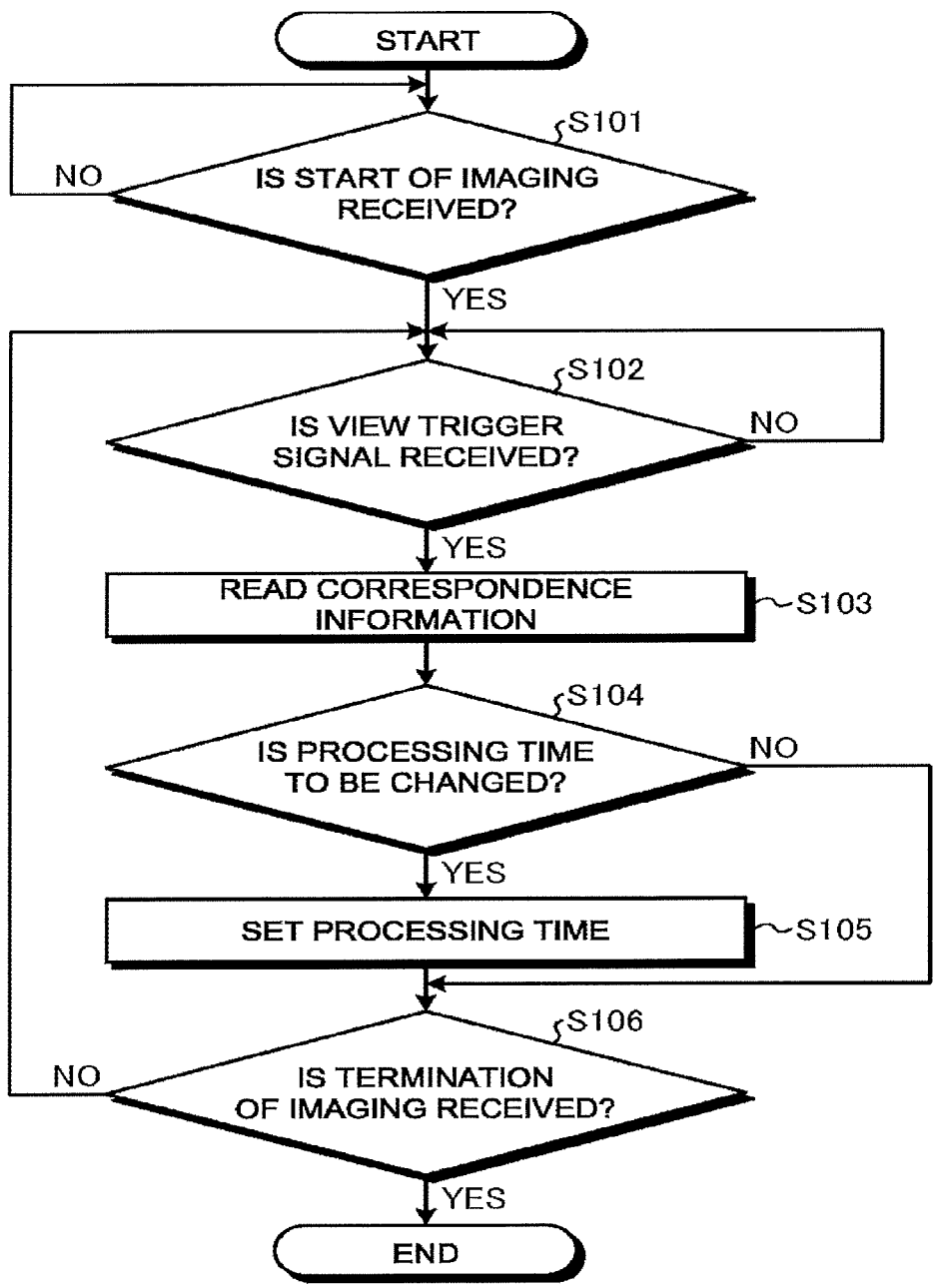
FIG. 13 is a flowchart illustrating the flow of a process performed by an FPGA according to the second embodiment.

Moreover, the FPGA 14a sets, in each of the ASICs 134, the processing time that corresponds to the view number during the imaging. In other words, the FPGA 14a dynamically changes the processing time, which has been set before the start of imaging, in accordance with the imaging angle, instead of fixing the processing time during the imaging. FIG. 13 is a flowchart illustrating the flow of a process performed by the FPGA 14a according to the second embodiment.

Step S101 to Step S106 are steps implemented by the FPGA 14a. At Step S101, the FPGA 14a determines whether the start of imaging is received from the gantry control device 16. If the FPGA 14a determines that the start of imaging is received from the gantry control device 16 (Step S101: Yes), the process proceeds to Step S102. In contrast, if the FPGA 14a does not determine that the start of imaging is received from the gantry control device 16 (Step S101: No), the FPGA 14a repeats the determination process at Step S101.

At Step S102, the FPGA 14a determines whether a view trigger signal is received from the gantry control device 16. If the FPGA 14a determines that the view trigger signal is received from the gantry control device 16 (Step S102: Yes), the process proceeds to Step S103. In contrast, if the FPGA 14a does not determine that the view trigger signal is received from the gantry control device 16 (Step S102: No), the FPGA 14a repeats the determination process at Step S102.

At Step S103, the FPGA 14a reads correspondence information. For example, the FPGA 14a reads the correspondence information illustrated in FIG. 12 from the storage circuitry 35. At Step S104, the FPGA 14a determines whether the processing time is to be changed. For example, the FPGA 14a updates the current view number every time receiving a view trigger signal. Then, the FPGA 14a compares a processing time corresponding to the updated view number and a processing time corresponding to the view number used before the update, for each of the detecting elements by referring to the correspondence information. If the compared processing times are different, the FPGA 14a determines that the processing time is to be changed. In contrast, if the compared processing times are the same, the FPGA 14a determines that the processing time is not to be changed.

If the FPGA 14a determines that the processing time is to be changed (Step S104: Yes), the process proceeds to Step S105. In contrast, if the FPGA 14a does not determine that the processing time is to be changed (Step S104: No), the process proceeds to Step S106.

At Step S105, the FPGA 14a sets the processing time that corresponds to the updated view number. At Step S106, the FPGA 14a determines whether the termination of imaging is received from the gantry control device 16. If the FPGA 14a determines that termination of imaging is received from the gantry control device 16 (Step S106: Yes), the FPGA 14a terminates the imaging. In contrast, if the FPGA 14a does not determine that the termination of imaging is received from the gantry control device 16 (Step S106: No), the FPGA 14a returns to Step S102 and performs the determination process.

As described above, in the second embodiment, the FPGA 14a sets, in each of the ASICs 134, the processing time that corresponds to the imaging angle during imaging. With this configuration, according to the second embodiment, it is possible to set optimal processing times for all of regions and angles that are adopted for imaging while the X-ray tube 12a and the X-ray detector 13 revolve once. Therefore, it is possible to obtain higher image quality and higher material decomposition capability.

In the second embodiment described above, the example has been described in which the X-ray dose incident on each of the detecting elements is estimated using two-dimensional scanogram images obtained from two directions, and the processing time is determined based on the estimation; however, possible embodiments are not limited to this example. For example, to determine a processing time corresponding to an imaging angle, it may be possible to estimate the X-ray does incident on each of the detecting elements on the basis of a three-dimensional scanogram image, and determine the processing time based on the estimation. When the X-ray does incident on each of the detecting elements is estimated based on the three-dimensional scanogram image and the processing time is determined based on the estimation, it becomes possible to split an imaging angle into smaller ranges and set processing times for theses imaging angles.

Third Embodiment

In a third embodiment, an example will be described in which the X-ray dose incident on each of the detecting elements 130 is calculated in real time, and a processing time is set based on the calculated X-ray dose. A configuration of the X-ray CT apparatus 1 according to the third embodiment is the same as the configuration of the X-ray CT apparatus 1 illustrated in FIG. 1 except that some parts of the determination function 377 and the FPGA 14a are different. Therefore, in the third embodiment, only functions executed by the determination function 377 and the FPGA 14a will be described.

The determination function 377 determines a processing time based on an X-ray dose incident on each of the detecting elements 130, and generates correspondence information. For example, the determination function 377 generates correspondence information, in which each of the detecting elements 130, the X-ray dose incident on each of the detecting elements 130, and the processing time of the ASIC 134 connected to each of the detecting elements 130 are associated with one another. FIG. 14 is a diagram for explaining the third embodiment. For example, as illustrated in FIG. 14, the determination function 377 generates correspondence information, in which an ID, a count number, and a processing time are associated with one another.

The "ID" in the correspondence information indicates an identifier for uniquely identifying the detecting element 130. The "count number" indicates an X-ray dose incident on each of the detecting elements 130 in a view unit. For example, in the "count number" corresponding to the "ID" of "yyyy", "C<C11", which indicates that a count value is smaller than C11, is stored as the X-ray dose in a view unit corresponding to a low-dose region. Further, for example, in the "count number" corresponding to the "ID" of "yyyy", "C11≤C<C12", which indicates that a count value is equal to or larger than C11 and smaller than C12, is stored as the X-ray dose in a view unit corresponding to a relatively low-dose region. Furthermore, for example, in the "count number" corresponding to the "ID" of "yyyy", "C12≤C<C13", which indicates that the count value is equal to or larger than C12 and smaller than C13, is stored as the X-ray dose in a view unit corresponding to a relatively high-dose region. Moreover, for example, in the "count number" corresponding to the "ID" of "yyyy", "C13≤C", which indicates that the count value is equal to or larger than C13, is stored as the X-ray dose in a view unit corresponding to a high-dose region.

Incidentally, there is individual variability among the detecting elements 130. To cope with this situation, it is desirable to set different count numbers among the IDs. For example, in the "count number" corresponding to the "ID" of "yyyx", "C<C21", which indicates that the count value is smaller than C21, is stored as the X-ray dose in a view unit corresponding to the low-dose region. Further, for example, in the "count number" corresponding to the "ID" of "yyyx", "C21≤C<C22", which indicates that the count value is equal to or larger than C21 and smaller than C22, is stored as the X-ray dose in a view unit corresponding to the relatively low-dose region. Furthermore, for example, in the "count number" corresponding to the "ID" of "yyyx", "C22≤C<C23", which indicates that the count value is equal to or larger than C22 and smaller than C23, is stored as the X-ray dose in a view unit corresponding to the relatively high-dose region. Moreover, for example, in the "count number" corresponding to the "ID" of "yyyx", "C23≤C", which indicates that the count value is equal to or larger than C23, is stored as the X-ray dose in a view unit corresponding to the high-dose region.

Similarly, for example, in the "count number" corresponding to the "ID" of "xxxx", "C<C31", which indicates that the count value is smaller than C31, is stored as the X-ray dose in a view unit corresponding to the low-dose region. Further, for example, in the "count number" corresponding to the "ID" of "xxxx", "C31≤C<C32", which indicates that a count value is equal to or larger than C31 and smaller than C32, is stored as the X-ray dose in a view unit corresponding to the relatively low-dose region. Furthermore, for example, in the "count number" corresponding to the "ID" of "xxxx", "C32≤C<C33", which indicates that the count value is equal to or larger than C32 and smaller than C33, is stored as the X-ray dose in a view unit corresponding to the relatively high-dose region. Moreover, for example, in the "count number" corresponding to the "ID" of "xxxx", "C33≤C", which indicates that the count value is equal to or larger than C33, is stored as the X-ray dose in a view unit corresponding to the high-dose region.

The "processing time" indicates a processing time of the ASIC 134 connected to the detecting element 130 identified by the ID, with respect to the count number in a corresponding view unit. Further, in the example illustrated in FIG. 14, it is assumed that the processing time V1<the processing time V2<the processing time V3<the processing time V4.

As one example, the determination function 377 determines that the processing time of the ASIC 134 connected to the detecting element 130 with the "ID" of "yyyy" is set to "T4" when the count number corresponds to "C<C11" indicating the X-ray dose corresponding to the low-dose region, "T3" when the count number corresponds to "C11≤C<C12" indicating the X-ray dose corresponding to the relatively low-dose region, "T2" when the count number corresponds to "C12≤C<C13" indicating the X-ray dose corresponding to the relatively high-dose region, and "T1" when the count number corresponds to "C13≤C" indicating the X-ray dose corresponding to the high-dose region.

The FPGA 14a sets the processing time corresponding to the position of each of the detecting elements 130 in the photon counting detector, in the ASIC 134 connected to each of the detecting elements 130 at the time of imaging. For example, the FPGA 14a sets the processing time for a current view in the ASIC 134 connected to each of the detecting elements 130, on the basis of the X-ray dose that has been incident on each of the detecting elements 130 for a view preceding the current view. In the third embodiment, it is assumed that the FPGA 14a sets the same processing time in all of the ASICs 134 as an initial value at the first scan position (the view number of 1) at the start of imaging. Then, the FPGA 14a performs a process of setting the processing time in each of the ASICs 134 on the basis of the X-ray dose incident on each of the detecting elements 130 for each view during the imaging. Further, while an example will be described in the third embodiment in which the processing time is set using a count result obtained for a view immediately preceding the current view, but it may be possible to set the processing time using a count result obtained for any view preceding the current view.

Figure 15:
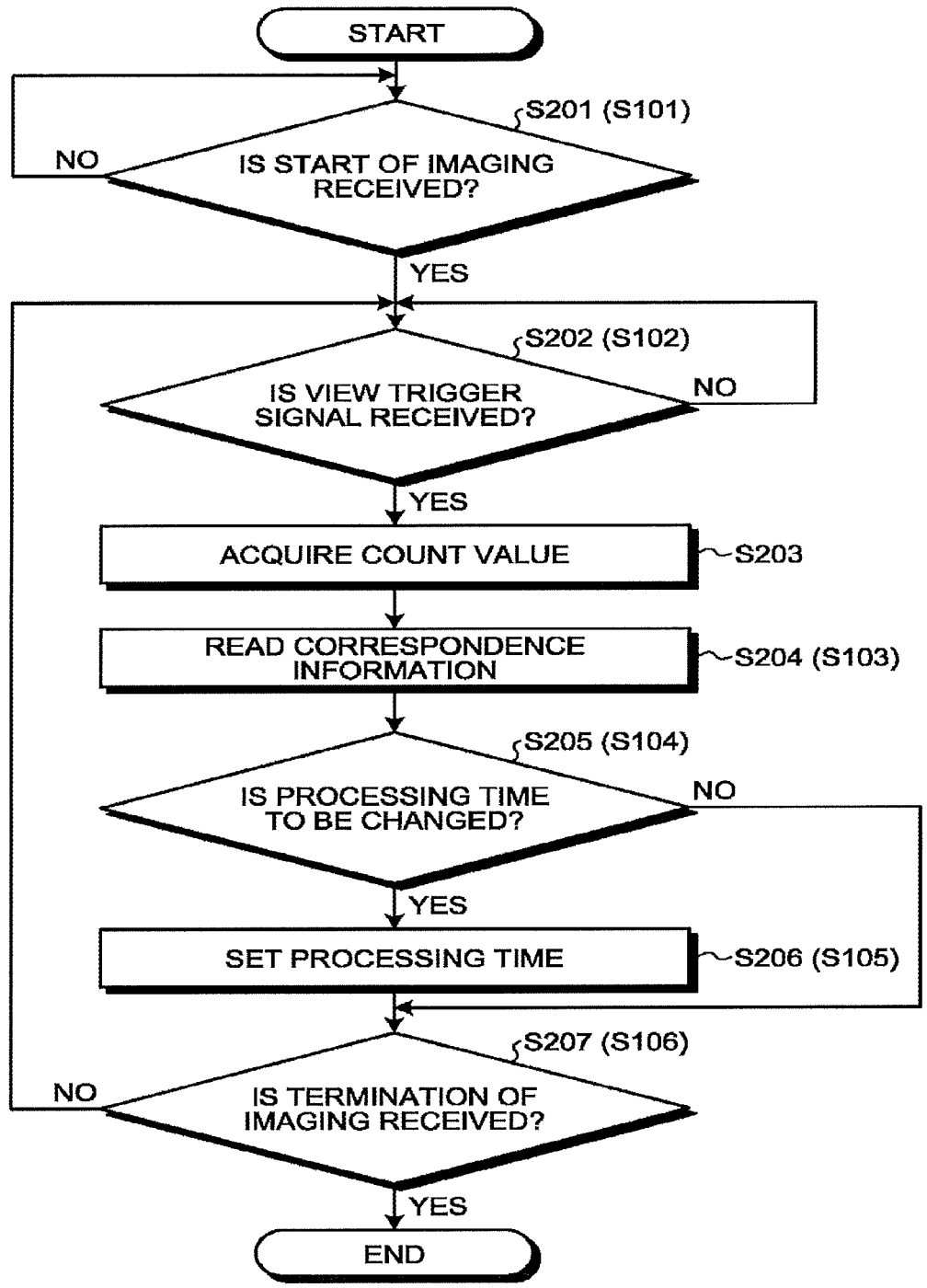
FIG. 15 is a flowchart illustrating the flow of a process performed by an FPGA 14a according to a third embodiment.

FIG. 15 is a flowchart illustrating the flow of a process performed by the FPGA 14a according to the third embodiment. Processes at Step S201 and Step S202 illustrated in FIG. 15 are the same as the processes at Step S101 and Step S102 illustrated in FIG. 13.

At Step S203, the FPGA 14a acquires a count value from the counter 134e. For example, the FPGA 14a sets a processing time for a current view in the ASIC 134 connected to each of the detecting elements 130, on the basis of an X-ray dose that has been incident on each of the detecting elements 130 for a view immediately preceding the current view.

A process of acquiring a count result for the immediately preceding view is first described. The FPGA 14a acquires the count result for the immediately preceding view from the counter 134e. FIG. 16 is a diagram for explaining the third embodiment. In FIG. 16, a timing at which the gantry control device 16 outputs a view trigger signal is illustrated. As illustrated in FIG. 16, one cycle of the view trigger signal corresponds to a period indicated by a double-headed arrow 16a. The view trigger signal of one cycle includes a positive pulse part as a first half and a negative pulse part as a second half. The FPGA 14a acquires a count result, which is obtained by performing counting in a period corresponding to one cycle of the view trigger signal, from the counter 134e.

At Step S204, the FPGA 14a reads correspondence information. For example, the FPGA 14a reads the correspondence information illustrated in FIG. 14 from the storage circuitry 35. At Step S205, the FPGA 14a determines whether the processing time is to be changed. For example, the FPGA 14a identifies a processing time corresponding to the count result for the immediately preceding view for each of the detecting elements 130 by referring to the correspondence information every time the count result for the immediately preceding view is acquired. Then, the FPGA 14a compares the identified processing time and the processing time that is currently set. If the compared processing times are different, the FPGA 14a determines that the processing time is to be changed. In contrast, if the compared processing times are identical, the FPGA 14a determines that the processing time is not to be changed.

If the FPGA 14a determines that the processing time is to be changed (Step S205: Yes), the process proceeds to Step S206. In contrast, if the FPGA 14a does not determine that the processing time is to be changed (Step S205: No), the process proceeds Step S207.

At Step S206, the FPGA 14a sets the processing time that corresponds to the count result for the immediately preceding view. For example, when a value of the count result acquired from the counter 134e that counts output results of the detecting element 130 identified by the ID of "yyyy" is equal to or larger than C11 and smaller than C12, the FPGA 14a sets the processing time T3 in the ASIC 134 corresponding to the ID of "yyyy". For another example, when a value of the count result acquired from the counter 134e that counts output results of the detecting element 130 identified by the ID of "yyyx" is equal to or larger than C22 and smaller than C23, the FPGA 14a sets the processing time T2 in the ASIC 134 corresponding to the ID of "yyyx".

At Step S207, the FPGA 14a determines whether the termination of imaging is received from the gantry control device 16. If the FPGA 14a determines that the termination of imaging is received from the gantry control device 16 (Step S207: Yes), the FPGA 14a terminates the imaging. In contrast, if the FPGA 14a does not determine that the termination of imaging is received from the gantry control device 16 (Step S207: No), the FPGA 14a returns to Step S202 and performs the determination process.

As described above, in the third embodiment, the FPGA 14a sets the processing time based on the count result for the immediately preceding view in each of the ASICs 134 during imaging. Therefore, according to the third embodiment, it is possible to set optimal processing times for all of regions and angles that are adopted for imaging while the X-ray tube 12a and the X-ray detector 13 revolve once. Consequently, it is possible to obtain higher image quality and higher material decomposition capability.

The reconstruction processing function 373 may perform material decomposition on the projection data, and reconstruct a material decomposition image using the material decomposition information that is a result of the material decomposition. In this case, to reconstruct the material decomposition, the reconstruction processing function 373 performs the process of correcting the spectrum of the detection data, which is explained in the modification of the first embodiment, in addition to the process of correcting the count number of the detection data. For example, the correspondence information illustrated in FIG. 13 is also stored in the storage circuitry 35 of the console 30. Then, the reconstruction processing function 373 selects an appropriate response function by referring to a setting value of the processing time when reconstructing the material decomposition image.

Modification of Third Embodiment

In the third embodiment described above, the example has been described in which the count value is calculated in a time corresponding to one cycle of the view trigger signal; however, possible embodiments are not limited to this example. For example, it may be possible to calculate the count value in a first half part or a second half part of the view trigger signal of one cycle. In other words, the FPGA 14a sets a processing time for a current view in the ASIC 134 connected to each of the detecting elements 130, on the basis of an X-ray dose that has been incident on each of the detecting elements 130 in a predetermined period within the period of a past view. FIG. 17 is a diagram for explaining a modification of the third embodiment. The upper diagram in FIG. 17 illustrates an example in which the count value is calculated in the first half part of the view trigger signal of one cycle, and the lower diagram in FIG. 17 illustrates an example in which the count value is calculated in the second half part of the view trigger signal of one cycle.

More specifically, as illustrated in the upper diagram in FIG. 17, the FPGA 14a calculates a count number only from a positive pulse part 17a that is the first half of the view trigger signal, selects a processing time in a negative pulse part 17b that is the second half, and sets the processing time at a changing point 17c of a next view trigger pulse. Alternatively, as illustrated in the lower diagram in FIG. 17, the FPGA 14a calculates a count number only from a negative pulse part 17d that is the second half of the view trigger signal, selects a processing time in a positive pulse part 17e that is the first half, and sets a processing time at a changing point 17f of a next view trigger pulse. In this manner, the FPGA 14a sets the processing time for the current view in the ASIC 134 connected to each of the detecting elements 130, on the basis of the X-ray dose that has been incident on each of the detecting elements 130 in the first half part or the second half part of the period of the past view.

With this configuration, the FPGA 14a is able to eliminate a time lag between selection of the processing time and setting of the processing time. In this case, the counter 134e outputs, to the FPGA 14a, a count result used for setting the processing time, in addition to a count result that is obtained in one cycle of the view trigger signal for reconstructing the X-ray CT image data. Further, the period for calculating the count value is not limited to the first half part or the second half part of the view trigger signal of one cycle, but may be a half period of the first half part or a half period of the second half part of the view trigger signal of one cycle.

Furthermore, in the third embodiment described above, the example has been described in which the FPGA 14a sets the same processing time as the initial value in all of the ASICs 134 at the first scan position (the view number of 1) at the start of imaging; however, possible embodiments are not limited to this example. For example, the FPGA 14a may set the processing time for the first scan position (the view number of 1) using the method described in the first embodiment. That is, at the first scan position (the view number of 1), the FPGA 14a sets a processing time that is based on the X-ray dose incident on each of the detecting elements 130, in the ASIC 134 connected to each of the detecting elements 130, by referring to the correspondence information illustrated in FIG. 8.

Moreover, while the example has been described in the third embodiment in which the processing time is set for each view, possible embodiments are not limited to this example. For example, the FPGA 14a may set a processing time for a predetermined view, such as for every five views.

Fourth Embodiment

Figure 18:
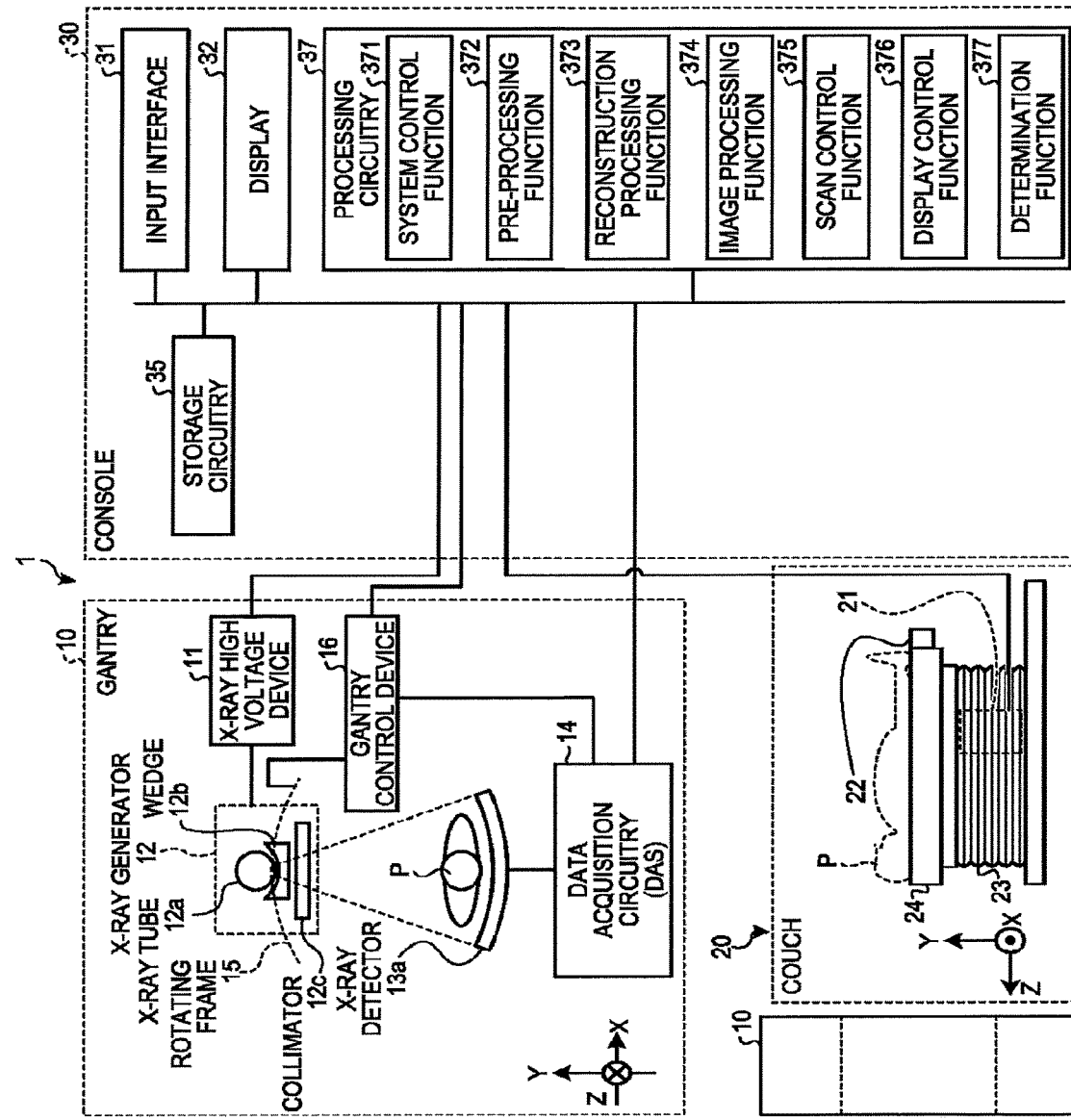
FIG. 18 is a diagram illustrating a configuration example of an X-ray CT apparatus according to a fourth embodiment.

Next, an X-ray CT apparatus 1 according to a fourth embodiment will be described. The same components as those of the first embodiment are denoted by the same reference signs, and explanation thereof will be omitted appropriately. FIG. 18 is a diagram illustrating a configuration example of the X-ray CT apparatus 1 according to the fourth embodiment. As illustrated in FIG. 18, the X-ray CT apparatus 1 according to the fourth embodiment is different from the X-ray CT apparatus 1 according to the first embodiment in that it includes an X-ray detector 13a instead of the X-ray detector 13.

Figure 19A:
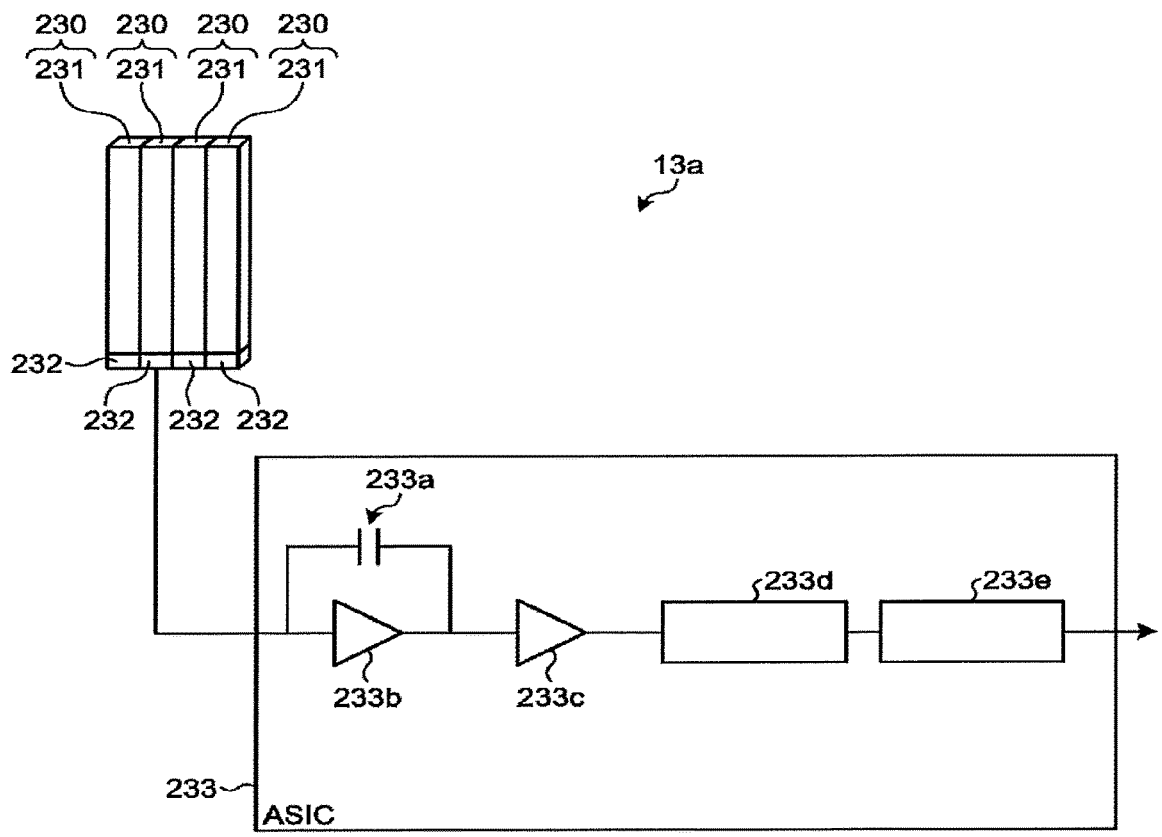
FIG. 19A is a diagram for explaining an X-ray detector according to the fourth embodiment.

The X-ray detector 13a is an example of a photon counting detector that includes a plurality of detecting elements and outputs signals corresponding to the number of photons that are counted. For example, the X-ray detector 13a is configured with a plurality of arrays of X-ray detecting elements (which may be referred to as "sensors" or simply "detecting elements"), where each of the arrays includes a plurality of X-ray detecting elements arranged in a channel direction along one arc centered at a focal point of the X-ray tube 12a. The X-ray detector 13a has a structure in which the plurality of arrays of X-ray detecting elements are arranged in a slice direction, where each of the arrays of X-ray detecting elements includes the plurality of X-ray detecting elements that are arranged in the channel direction. Each of the X-ray detecting elements included in the X-ray detector 13a is configured to detect X-rays that have been emitted from the X-ray generator 12 and have passed through the subject P and to output an electrical signal (a pulse) corresponding to the X-ray dose to the data acquisition circuitry 14. The electrical signal output by each of the X-ray detecting elements may also be referred to as a detection signal. FIG. 19A is a diagram for explaining the X-ray detector 13a according to the fourth embodiment.

As illustrated in FIG. 19A, the X-ray detector 13a is a photon counting detector that includes a plurality of detecting units, each of which includes a detecting element 230 that detects X-ray photons and an ASIC 233 that is connected to the detecting element 230 and counts the X-ray photons detected by the detecting element 230. The detecting element is one example of a detection circuitry. In the example in FIG. 19A, the four detecting elements 230 and only one of the ASICs 233 for the respective detecting elements 230 are illustrated.

As illustrated in FIG. 19A, each of the detecting elements 230 is a detector of an indirect conversion type, and includes a scintillator 231 and a photo sensor 232. That is, the X-ray detector 13a includes the plurality of detecting elements 230, each of which includes the scintillator 231 and the photo sensor 232. The scintillator 231 is configured with a scintillator crystal that outputs a certain amount of light corresponding to incident X-ray energy. The photo sensor 232 has a function to convert light into electrical signals corresponding to the amount of light output from the scintillator 231, and is configured with, for example, an avalanche photodiode (APD) or a silicon photomultiplier (SiPM). The photo sensor 232 provided in each of the scintillators 231 constitute a single pixel. Therefore, the photo sensor 232 may also be referred to as one pixel. Further, while not illustrated in FIG. 19A, a grid is disposed on the surface of the scintillator 231 on an X-ray incident side. The grid is configured with an X-ray blocking plate having a function to absorb scattered X-rays.

Figure 19B:
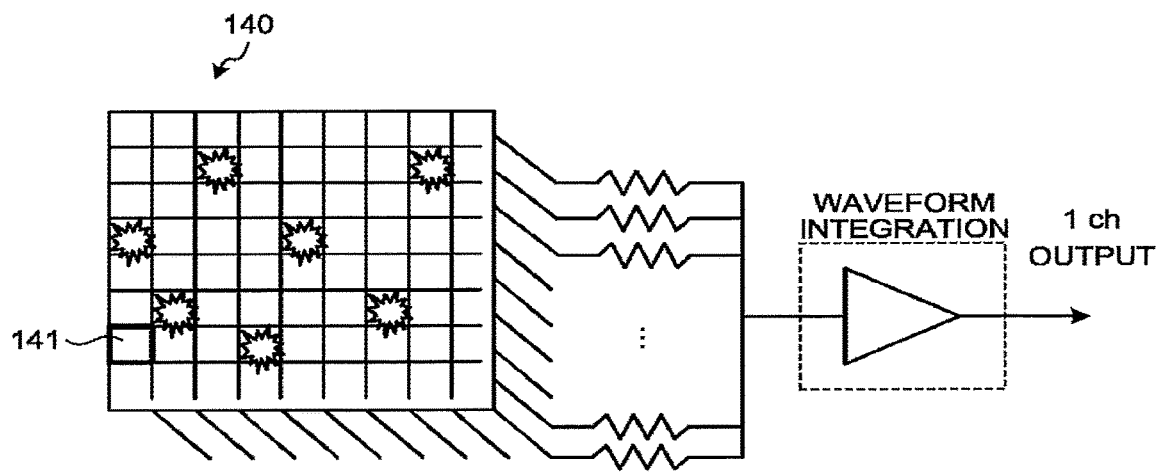
FIG. 19B is a diagram for explaining a photo sensor according to the fourth embodiment.

In the following, an example will be described in which the photo sensor 232 is a SiPM. The photo sensor 232 includes an APD cell that includes a plurality of APDs each of which operates individually. In general, a few hundreds to thousands of APDs are arranged in one pixel. FIG. 19B is a diagram for explaining the photo sensor according to the fourth embodiment. In the example in FIG. 19B, 72 APDs 141 that are arranged in a matrix of 9 columns and 8 rows among APDs included in an APD cell 140 are illustrated.

The APD 141 is a photodiode having an avalanche region, and is a photodiode using an avalanche multiplication effect that causes a photocurrent to be multiplied by application of a reverse voltage (also referred to as a "reverse bias voltage" or a "driving voltage"). The avalanche multiplication effect is an effect, in which while a reverse voltage is being applied to a p-n junction, electrons flow to the N layer and holes flow to the P layer in electron-hole pairs generated in the depletion layer, but some of the electrons and the holes collide with other atoms and new electron-hole pairs are generated. Then, a chain reaction occurs such that the electrons and the holes further collide with atoms and new electron-hole pairs are further generated. That is, in the APD 141, a larger number of electron-hole pairs than electron-hole pairs that are generated by incident light will be generated. As described above, the APD 141 is a highly sensitive photodiode that is able to obtain high output even with weak light.

The scintillator 231, upon absorbing X-rays, outputs a certain number of beams of visible light that is approximately proportional to energy of the absorbed X-rays. A part of the beams of visible light enters the APD cell 140. The APD cell 140 that has absorbed one or more beams of visible light outputs a signal. Then, the APD cell 140 outputs a sum of the signals output from all of the APDs 141 in the APD cell 140 as an output signal of one pixel.

More specifically, each of the APDs 141 of the APD cell 140 outputs the same pulse upon detecting one or more beams of light. Therefore, the APD cell 140 outputs an output signal corresponding to the total number of the APDs 141 that have detected light. For example, it is assumed that an output signal in a case where a single beam of light is detected is denoted by A. The APD cell 140 outputs the output signal A when a single beam of light is detected, and outputs an output signal n×A when n beams of light are detected. In this manner, the APD cell 140 outputs an output signal corresponding to the total number of the APDs 141 that have detected light, for each pixel. In other words, the APD cell 140 outputs an output signal corresponding to the energy of X-rays.

Referring back to FIG. 19A, the ASIC 233 discriminates individual electric charges output from the detecting element 230, and counts the number of X-ray photons incident on the detecting element 230. Further, the ASIC 233 performs arithmetic processing that is based on magnitudes of individual electric charges, and measures energy of the counted X-ray photons. The ASIC 233 includes a capacitor 233a, an amplification circuitry 233b, a waveform shaping circuitry 233c, a comparator circuitry 233d, and a counter 233e, for example.

The capacitor 233a accumulates the electric charges output from the detecting element 230. The amplification circuitry 233b is a circuitry that integrates the electric charges accumulated in the capacitor 233a and outputs a pulse signal corresponding to the electric quantity, in response to the X-ray photons incident on the detecting element 230. The pulse signal has a wave height and an area corresponding to the amount of energy of photons. In other words, a wave height value of the electrical signal (pulse) and an energy value of the X-ray photons are correlated with each other.

Incidentally, the amplification circuitry 233b includes, for example, a single-ended amplifier or a differential amplifier similar to the amplifier included in the above-described amplification circuitry 134b. When the amplifier is the single-ended amplifier, the amplifier is grounded and amplifies a potential difference between the grounding potential (ground) and a potential indicated by an electrical signal output by the detecting element 230. When the amplifier is the differential amplifier, positive input (+) of the amplifier is connected to the detecting element 230 and the negative input (−) is grounded. The differential amplifier amplifies a potential difference between a potential indicated by an electrical signal that is input to the positive input from the detecting element 230 and the grounding potential indicated by an electrical signal input to the negative input.

The waveform shaping circuitry 233c is a circuitry that adjusts the frequency characteristic of a pulse signal output from the amplification circuitry 233b and shapes the waveform of the pulse signal by giving gain and offset.

The comparator circuitry 233d is a circuitry that compares the wave height or the area of a response pulse signal that is obtained in response to the incident photons, with thresholds that are set in advance in accordance with a plurality of energy bands that need to be discriminated, and outputs results of comparison with the thresholds to the counter 134e.

The counter 233e counts a discrimination result of the waveform of the response pulse signal for each corresponding energy band, and outputs a count result of photons as digital data to the data acquisition circuitry 14.

Figure 20:
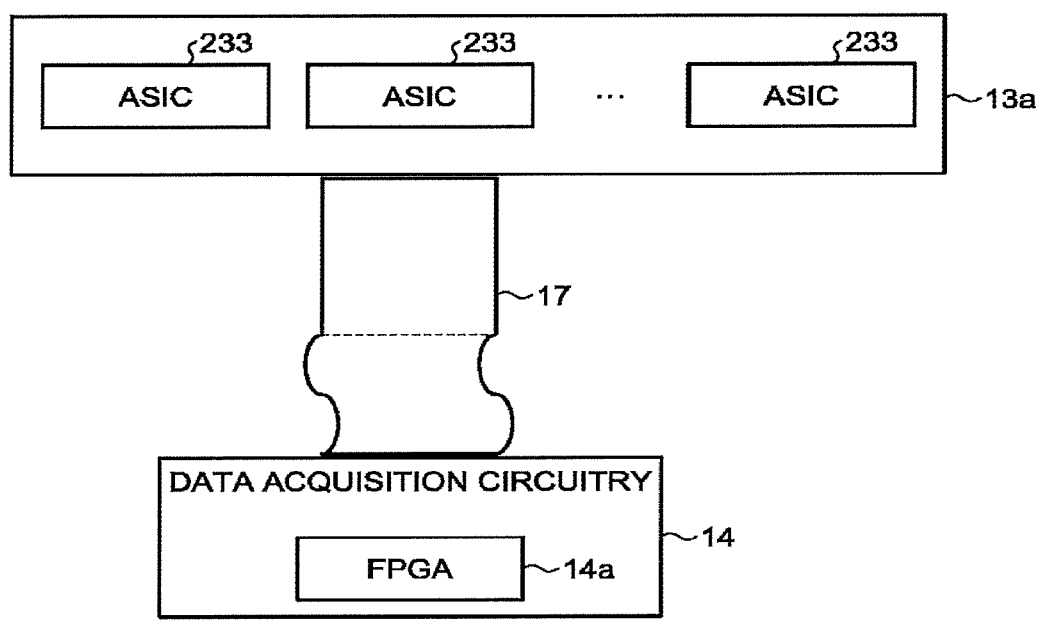
FIG. 20 is a diagram for explaining data acquisition circuitry according to the fourth embodiment.

Referring back to FIG. 18, the data acquisition circuitry 14 transmits various controls signals to the X-ray detector 13a. FIG. 20 is a diagram for explaining the data acquisition circuitry 14 according to the fourth embodiment. As illustrated in FIG. 20, the data acquisition circuitry 14 is connected to the X-ray detector 13a, which includes the ASIC 233, via the rigid flexible board 17, for example. For example, the FPGA 14a receives a view trigger signal from the gantry control device 16, and controls the X-ray detector 13a based on the received view trigger signal.

Further, the determination function 377 according to the fourth embodiment determines a driving voltage corresponding to the position of each of the scintillators 231 in the X-ray detector 13a, in the photo sensor 232 corresponding to each of the scintillators 231 at the time of imaging. Details of the determination function 377 according to the fourth embodiment will be described later.

An exemplary configuration of the X-ray CT apparatus 1 according to the fourth embodiment has been explained. The X-ray CT apparatus 1 according to the fourth embodiment configured as described above integrates output signals (electric charges) output from the X-ray detector 13a and performs waveform shaping, and, thereafter, sets a plurality of divided windows in accordance with signal levels and counts the number of incident X-rays for each of the windows by using a counter. The X-ray CT apparatus 1 acquires data of needed cycles, and acquires CT images with a plurality of energy windows. Here, in the photo sensor 232, such as a SiPM, a photon detection efficiency (PDE) or a gain characteristic is changed depending on the driving voltage set in the APD 141.

For example, if the driving voltage of the APD 141 is increased, the PDE is increased and the gain is also increased, but an effective pulse width is increased and a frequency characteristic is reduced. In contrast, if the driving voltage of the APD 141 is reduced, the PDE is reduced and the gain is also reduced, but the effective pulse width is reduced and the frequency characteristic is increased. Therefore, it is necessary to appropriately select the driving voltage of the APD 141 depending on the incident X-ray dose, required image quality, or the material decomposition capability. In the following, the "driving voltage of the APD 141" will be appropriately described as the "driving voltage of the photo sensor 232".

Here, as a comparative example, a case will be described in which the driving voltage of each of the photo sensors 232 in the X-ray detector 13a is set to a constant value. That is, in the comparative example, it is assumed that the driving voltages of all of the photo sensors 232 are set to the same value. With reference to FIG. 4 described above, a problem with the comparative example will be described.

In the X-ray detector 13a, the X-ray dose incident on each of the scintillators 231 of the detecting elements 230 is different depending on the position in the X-ray detector 13a. For example, as illustrated in FIG. 4, in a central portion of the X-ray detector 13a, the amount of absorption by the subject P is large, so that the X-ray dose incident on the scintillator 231 is reduced. Here, it is assumed that the X-ray dose in this case is denoted by n1 (count/sec), for simplicity of explanation. In contrast, in edge portions of the X-ray detector 13a, the amount of absorption by the subject P is small or zero, so that the X-ray dose incident on the scintillator 231 is increased. Here, it is assumed that the X-ray dose in this case is denoted by n2 (count/sec), for simplicity of explanation. The central portion of the X-ray detector 13a indicates a region around the center in the channel direction of the X-ray detector 13a, and the edge portions of the X-ray detector 13a indicate edge regions distant from the center in the channel direction of the X-ray detector 13a.

In the X-ray CT apparatus 1, when the number of X-ray photons incident on the X-ray detector 13a is large, a phenomenon called pile-up, in which another X-ray is incident on the X-ray detector 13a during a processing time of a signal that has been generated by a single X-ray photon, may continuously occur. If the pile-up occurs, the number of detected X-ray photons and the energy value of the detected X-rays are deviated from correct values, so that image quality to be eventually obtained will be deteriorated.

To prevent degradation of image quality due to the pile-up as described above, a high frequency characteristic is needed and the driving voltage of the photo sensor 232 needs to be reduced. If the driving voltage of the photo sensor 232 is reduced, the edge portions, where the X-ray dose incident on the scintillator 231 is high, is less likely to be influenced by pile-up, so that the image quality can be improved; however, the PDE and the gain are reduced and the S/N ratio is reduced accordingly, so that the material decomposition capability is reduced in the central portion where the X-ray dose incident on the scintillator 231 is low. In contrast, if the driving voltage of the photo sensor 232 is increased, the PDE and the gain are increased and the S/N ratio is improved accordingly, so that the material decomposition capability is improved in the central portion where the X-ray dose incident on the scintillator 231 is low; however, the edge portions, where the X-ray dose incident on the scintillator 231 is high, is likely to be influenced by pile-up, so that the image quality is deteriorated.

Figure 21:
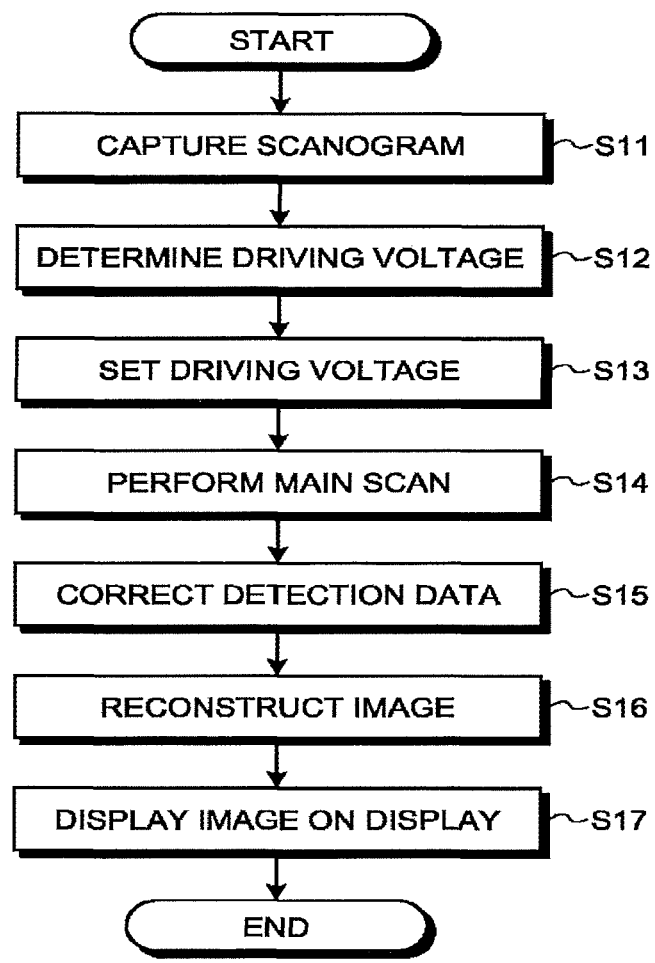
FIG. 21 is a flowchart illustrating the flow of a process performed by the X-ray CT apparatus according to the fourth embodiment.
Figure 22:
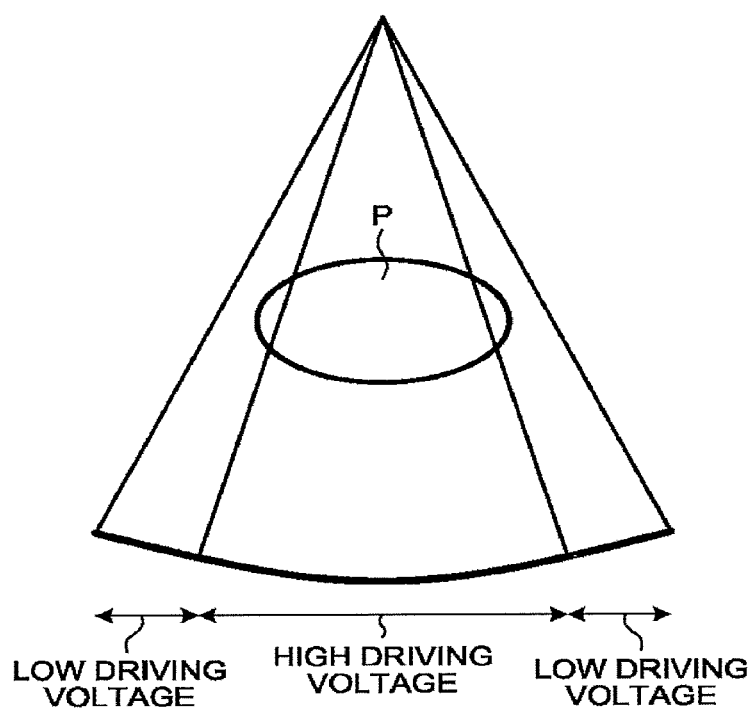
FIG. 22 is a diagram for explaining the fourth embodiment.
Figures 23, 24:
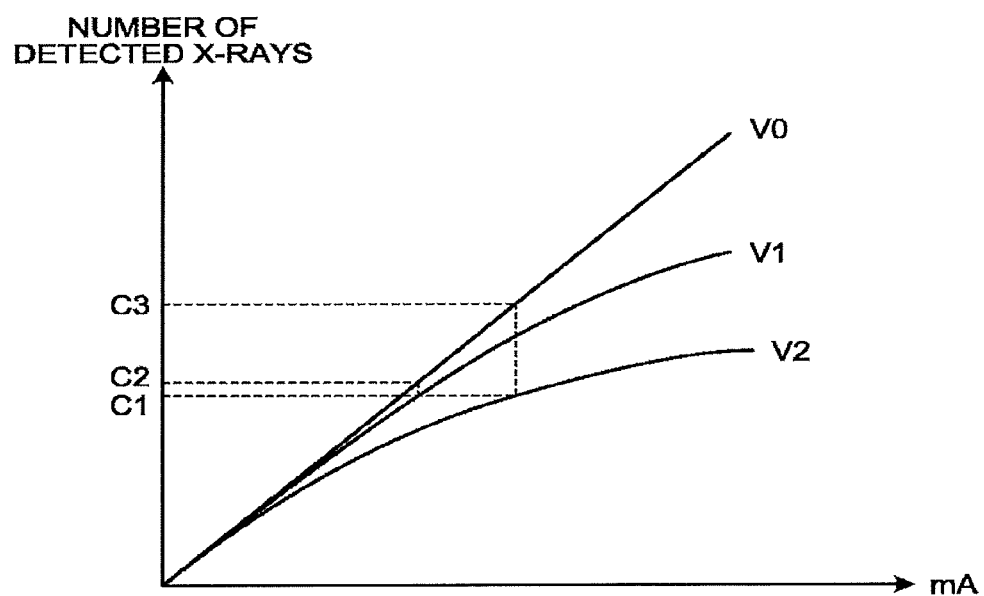
FIG. 23 is a diagram for explaining the fourth embodiment.
FIG. 24 is a diagram for explaining the fourth embodiment.

In view of the foregoing situation, the X-ray CT apparatus 1 according to the fourth embodiment sets the driving voltage corresponding to the position of each of the scintillators 231 in the photon counting detector, in the photo sensor 232 corresponding to each of the scintillators 231 at the time of imaging. In the following, the fourth embodiment will be described with reference to FIG. 21 to FIG. 24. FIG. 21 is a flowchart illustrating the flow of a process performed by the X-ray CT apparatus 1 according to the fourth embodiment, and FIG. 22 to FIG. 24 are diagrams for explaining the fourth embodiment.

FIG. 21 illustrates the flowchart for explaining operation performed by the X-ray CT apparatus 1, and correspondence between the steps and the components will be described below. Step S11 is a step corresponding to the scan control function 375. Step S11 is a step at which the processing circuitry 37 calls and executes a predetermined program corresponding to the scan control function 375 from the storage circuitry 35, and the scan control function 375 is implemented. At Step S11, the scan control function 375 captures a scanogram. For example, the scan control function 375 fixes the X-ray tube 12a at the position of 0 degree (a position in the front direction of the subject P), and captures a two-dimensional scanogram image.

Step S12 is a step corresponding to the determination function 377. Step S12 is a step at which the processing circuitry 37 calls and executes a predetermined program corresponding to the determination function 377 from the storage circuitry 35, and the determination function 377 is implemented. At Step S12, the determination function 377 determines a driving voltage.

Here, the determination function 377 determines the driving voltage based on the X-ray dose incident on each of the scintillators 231, and generates correspondence information. For example, the determination function 377 estimates the X-ray dose incident on each of the scintillators 231 from a count result obtained by each of the detecting elements 230, and determines the driving voltage based on the estimated X-ray dose. As one example, the determination function 377 estimates the X-ray dose incident on the scintillator 231 from a count result of scanograms captured at Step S1, and determines the driving voltage.

The determination function 377 determines the driving voltage by performing a threshold determination process on the count result of the scanograms as described below. For example, the determination function 377 estimates that the X-ray dose incident on the scintillator 231 is high in a certain region, in which the count result of the scanograms is equal to or larger than a threshold, in the channel direction, and selects this region as a high-dose region. Then, the determination function 377 reduces the driving voltage of the photo sensor 232 corresponding to the scintillator 231 that corresponds to the high-dose region. In contrast, the determination function 377 estimates that the X-ray dose incident on the scintillator 231 is low in a certain region, in which the count result of the scanograms is smaller than the threshold, in the channel direction, and selects this region as a low-dose region. Then, the determination function 377 increases the driving voltage of the photo sensor 232 corresponding to the scintillator 231 that corresponds to the low-dose region.

More specifically, the incident X-ray dose is reduced in the central portion in the channel direction because the amount of absorption by the subject P is large. Therefore, as illustrated in FIG. 22, the determination function 377 selects the central portion in the channel direction as the low-dose region, and increases the driving voltage of the central portion in the channel direction. Further, the incident X-ray dose is increased in the edge portions in the channel direction because the amount of absorption by the subject P is small or zero. Therefore, as illustrated in FIG. 22, the determination function 377 selects the edge portions in the channel direction as the high-dose regions, and reduces the driving voltages of the edge portions in the channel direction.

The determination function 377 may determine the driving voltage by performing the threshold determination process on a representative slice, and apply the determined driving voltage to the other slices in the same manner. Alternatively, the determination function 377 may determine the driving voltage by performing the threshold determination process in each of the slice directions. The representative slice is, for example, a central slice in the slice direction.

Then, the determination function 377 generates correspondence information, in which each of the scintillators 231 and the driving voltage of the photo sensor 232 corresponding to each of the scintillators 231 are associated with each other. More specifically, as illustrated in FIG. 23, the determination function 377 generates correspondence information, in which an ID and a driving voltage are associated with each other.

The "ID" in the correspondence information indicates an identifier for uniquely identifying the scintillator 231, and the "driving voltage" indicates a driving voltage of the photo sensor 232 corresponding to the scintillator 231 identified by the ID. Further, in the example illustrated in FIG. 23, it is assumed that a driving voltage V1<a driving voltage V2, the scintillators 231 with the "IDs" of "yyyy" and "zzzz" are disposed in the high-dose regions that are the edge portions of the X-ray detector 13a in the channel direction, and the scintillator 231 with the "ID" of "xxxx" is arranged in the low-dose region that is the central portion of the X-ray detector 13a in the channel direction.

As one example, the determination function 377 determines that the driving voltage of each of the APDs 141 included in the APD cells 140 of the photo sensors 232 corresponding to the scintillators 231 with the "IDs" of "yyyy" and "zzzz" are "V1", and determines that the driving voltage of each of the APDs 141 included in the APD cell 140 of the photo sensor 232 corresponding to the scintillator 231 with the "ID" of "xxxx" is "V2".

Step S13 is a step implemented by the FPGA 14a. At Step S13, the FPGA 14a sets a driving voltage. Here, the FPGA 14a sets the driving voltage corresponding to the position of the scintillator 231 in the photon counting detector, in the photo sensor 232 corresponding to each of the scintillators 231 at the time of imaging. For example, the FPGA 14a sets, in the photo sensor 232 corresponding to each of the scintillators 231, the driving voltage that is based on the X-ray dose incident on each of the scintillators 231.

As one example, the FPGA 14a sets the driving voltage in each of the photo sensors 232 by referring to the correspondence information illustrated in FIG. 23. In other words, the FPGA 14a sets, in each of the photo sensors 232, the driving voltage that is based on the X-ray dose incident on each of the scintillators 231, where the X-ray dose is estimated from the count result obtained by each of the detecting elements 230. More specifically, the FPGA 14a sets the driving voltage "V1" in each of the APDs 141 included in the APD cells 140 of the photo sensors 232 corresponding to the scintillators 231 with the IDs of "yyyy" and "zzzz". Further, the FPGA 14a sets the driving voltage "V2" in each of the APDs 141 included in the APD cell 140 of the photo sensor 232 corresponding to the scintillator 231 with the ID of "xxxx". In this manner, the FPGA 14a sets a larger driving voltage in the photo sensor 232 that corresponds to the scintillator 231 for which the incident X-ray dose is smaller than the threshold, as compared to the photo sensor 232 that corresponds to the scintillator 231 for which the incident X-ray dose is equal to or larger than the threshold. In the fourth embodiment, the driving voltage that is set in each of the photo sensors 232 at the start of imaging is fixed during the imaging.

Step S14 is a step corresponding to the scan control function 375. Step S14 is a step at which the processing circuitry 37 calls and executes a predetermined program corresponding to the scan control function 375 from the storage circuitry 35, and the scan control function 375 is implemented. At Step S14, the scan control function 375 performs main scan.

Step S15 is a step corresponding to the pre-processing function 372. Step S15 is a step at which the processing circuitry 37 calls and executes a predetermined program corresponding to the pre-processing function 372 from the storage circuitry 35, and the pre-processing function 372 is implemented. Meanwhile, detection data obtained through the main scan at Step S14 is a signal obtained through a process that is performed with a different driving voltage by each of the photo sensors 232. Here, if the driving voltage is changed, a pile-up occurrence rate is also changed. If the pile-up occurrence rate is changed, the count number is reduced and a ratio at which a spectrum is shifted to the high side is changed, for example. In other words, by setting a different driving voltage, the count number and the spectrum of the detection data are changed. In view of the foregoing situation, at Step S15, the pre-processing function 372 corrects the detection data. In other words, the pre-processing function 372 corrects the count result obtained by the data acquisition circuitry 14.

With reference to FIG. 24, an example will be described in which the count number of the detection data is corrected. In FIG. 24, the horizontal axis represents a tube current value (mA), and the vertical axis represents the number of detected X-rays. Here, in theory, the X-ray irradiation dose and the number of detected X-rays have a linear relationship. For example, as indicated by V0 in FIG. 24, the number of detected X-rays increases with an increase in the X-ray irradiation dose. However, in actual measurement, a non-linear relationship is obtained, in which the number of detected X-rays reaches a peak with an increase in the irradiation dose. The irradiation dose with which the number of detected X-rays reaches the peak is determined depending on the driving voltage. For example, the number of detected X-rays is reduced with an increase in the driving voltage. In view of the foregoing situations, the pre-processing function 372 identifies the driving voltage set in each of the photo sensors 232, and corrects the number of X-rays that is the count result in each of the ASICs 233. In the following, it is assumed that the driving voltage V1<the driving voltage V2, and the numbers of detected X-rays with respect to the X-ray irradiation dose are measured in advance at the driving voltage V1 and the driving voltage V2.

For example, in the example illustrated in FIG. 24, in a case where the number of detected X-rays is C1 and the driving voltage is V1, the pre-processing function 372 corrects the number of detected X-rays from C1 to C2. Further, in the example illustrated in FIG. 24, in a case where the number of detected X-rays is C1 and the driving voltage is V2, the pre-processing function 372 corrects the number of detected X-rays from C1 to C3.

Step S16 is a step corresponding to the reconstruction processing function 373. Step S16 is a step at which the processing circuitry 37 calls and executes a predetermined program corresponding to the reconstruction processing function 373 from the storage circuitry 35, and the reconstruction processing function 373 is implemented. At Step S16, the reconstruction processing function 373 reconstructs an image. For example, the reconstruction processing function 373 generates a base image based on the projection data that is obtained by performing a pre-processing process on the detection data that is corrected by the pre-processing function 372 at Step S15. In other words, the reconstruction processing function 373 reconstructs the image based on the corrected count result.

Step S17 is a step corresponding to the display control function 376. Step S7 is a step at which the processing circuitry 37 calls and executes a predetermined program corresponding to the display control function 376 from the storage circuitry 35, and the display control function 376 is implemented. At Step S17, the display control function 376 displays an image on the display 32.

As described above, the X-ray CT apparatus 1 according to the fourth embodiment sets the driving voltage corresponding to the position of each of the scintillators 231 in the X-ray detector 13a, in the photo sensor 232 corresponding to each of the scintillators 231 at the time of imaging. For example, the X-ray CT apparatus 1 sets a larger driving voltage in the photo sensor 232 of the detecting element 230 disposed in the low-dose region that is the central portion in the channel direction in the X-ray detector 13a, as compared to the photo sensor 232 of the detecting element 230 disposed in the high-dose regions that are the edge portions in the channel direction.

With this configuration, in the central portion of the X-ray detector 13a in the channel direction, the driving voltage is increased, so that the S/N ratio is improved and the material decomposition capability is improved, for example. In contrast, in the edge portions of the X-ray detector 13a in the channel direction, the driving voltage is reduced and the influence of pile-up is reduced even under the high-dose condition, so that the histogram is less deformed and an approximately correct counting rate can be obtained. Further, it is less necessary to perform material decomposition in the high-dose regions that are the edge portions of the X-ray detector 13a in the channel direction, and a region where the material decomposition capability is needed is the low-dose region that is the central portion of the X-ray detector 13a in the channel direction. Therefore, according to the X-ray CT apparatus 1 of the fourth embodiment, it is possible to obtain high image quality and high material decomposition capability.

In the low-dose region, the driving voltage is increased; however, because the radiation dose is low, it is possible to neglect deformation of the histogram and an influence on a count rate due to pile-up. Further, in the high-dose region, the driving voltage is reduced, and the S/N ratio is reduced accordingly; however, the count rate is not influenced and an influence on the image quality may be excluded. Therefore, in the X-ray CT apparatus 1 according to the fourth embodiment, it is possible to omit the above-described correction process performed by the pre-processing function 372.

Furthermore, the reconstruction processing function 373 may perform material decomposition on the projection data, and reconstruct a material decomposition image using material decomposition information that is a result of the material decomposition. In this case, to reconstruct the material decomposition image, it is necessary to perform a process of correcting the spectrum of the detection data, in addition to the process of correcting the count number of the detection data. Hereinafter, the process of correcting the spectrum of the detection data performed by the reconstruction processing function 373 will be described.

A relationship between a spectrum S(E) of an X-ray detected by the X-ray detector 13a and a spectrum $S_0(E)$ of an X-ray incident on the X-ray detector 13a is represented by Equation (1) described above, using a response function R (E, nτ).

Here, the processing time τ includes a processing time of the scintillator 231, a processing time of the X-ray detector 13a, and a processing time of a circuitry system, such as the ASIC 233. A plurality of response functions R are set by the X-ray dose n and the driving voltage. Here, the spectrum S(E) of the X-rays detected by the X-ray detector 13a, the spectrum S0(E) of the X-rays emitted from the X-ray tube 12a, and the response function R (E, nτ) are already known. Therefore, the reconstruction processing function 373 is able to calculate the amount of absorption (−μL) from Equation (1). In other words, the reconstruction processing function 373 is able to perform material decomposition by additionally taking into account a change in the spectrum of the detection data caused by a difference in the driving voltage. In a case where the base image is generated, it is sufficient to correct the count number of the detection data, and it is not necessary to correct a difference in the spectrum that occurs in the detection data.

Modification of Fourth Embodiment

In the fourth embodiment described above, the example has been described in which the material decomposition is performed using a response function in which the driving voltage is taken into account; however, possible embodiments are not limited to this example. For example, the reconstruction processing function 373 may perform the material decomposition using the lookup table as illustrated in FIG. 9 described above. For example, the reconstruction processing function 373 may perform material decomposition by identifying a histogram that is similar to the detection data by using the lookup table that is generated under an imaging condition in which pile-up is likely to occur.

Fifth Embodiment

In the fourth embodiment described above, the example has been described in which the driving voltage corresponding to the position of each of the scintillators 231 is set in the photo sensor 232 corresponding to each of the scintillators 231 at the time of imaging. In the fourth embodiment, the driving voltage set in each of the photo sensors 232 at the start of imaging is fixed during the imaging.

Incidentally, a cross-section of the subject P usually has an elliptical shape rather than a circular shape. Therefore, if a region with a low driving voltage and a region with a high driving voltage are fixed as illustrated in FIG. 22, high-dose X-rays may be incident on the region in which a high driving voltage is set while the X-ray tube 12a revolves once around the subject P, depending on an imaging angle. In this case, the count number may be reduced or the spectrum is shifted to the high side due to pile-up, so that image quality is deteriorated.

To cope with this situation, it may be possible to dynamically change the driving voltage, which has been set in accordance with the position of each of the scintillators 231, depending on an imaging angle of the X-ray tube 12a, instead of fixing the driving voltage during the imaging. Therefore, in a fifth embodiment, an example will be described in which the driving voltage is set in each of the photo sensors 232 in accordance with an imaging angle.

A configuration of the X-ray CT apparatus 1 according to the fifth embodiment is the same as the configuration of the X-ray CT apparatus 1 illustrated in FIG. 18 except that some parts of the determination function 377 and the FPGA 14a are different. Therefore, in the fifth embodiment, only functions executed by the determination function 377 and the FPGA 14a will be described.

The determination function 377 determines a driving voltage corresponding to an imaging angle, on the basis of an X-ray dose incident on each of the detecting elements 230, and generates correspondence information. For example, the determination function 377 estimates the X-ray dose incident on each of the scintillators 231 from the count result obtained by each of the detecting elements 230, and determines a driving voltage that is based on the estimated X-ray dose. As one example, the determination function 377 estimates the X-ray dose incident on the scintillator 231 from the count result of scanograms, and determines the driving voltage. In the fifth embodiment, the scan control function 375 captures two-dimensional scanogram images in two directions. For example, the scan control function 375 captures a two-dimensional scanogram image (a scanogram at 0 degree) while fixing the X-ray tube 12a at the position of 0 degree (a position in the front direction of the subject P), and thereafter captures a two-dimensional scanogram image (a scanogram at 90 degrees) while fixing the X-ray tube 12a at the position of 90 degrees (a position in the side direction of the subject P).

Figure 25:
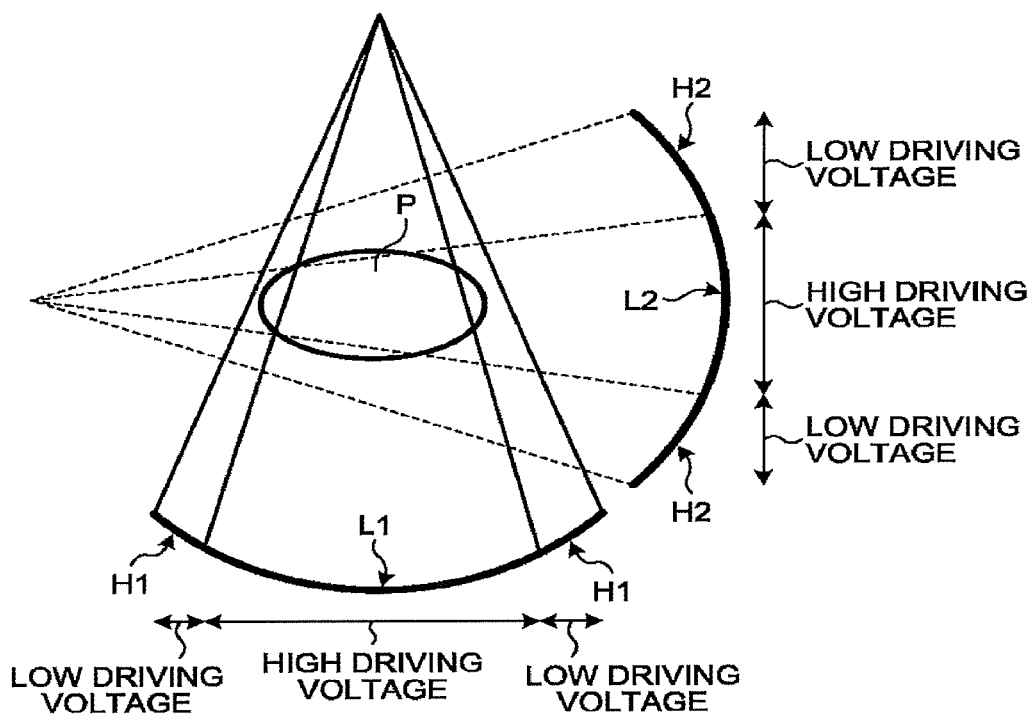
FIG. 25 is a diagram for explaining the fifth embodiment.

The determination function 377 determines the driving voltage by performing a threshold determination process on the count results of the two-dimensional scanogram images obtained from the two directions. In other words, the determination function 377 estimates the X-ray dose incident on each of the scintillators 231 using the two-dimensional scanogram images obtained from the two directions, and determines the driving voltage. FIG. 25 is a diagram for explaining the fifth embodiment.

For example, as illustrated in FIG. 25, the determination function 377 estimates that the X-ray dose incident on the scintillator 231 is high in a certain region, in which the count result of the scanograms at 0 degree is equal to or larger than a threshold, in the channel direction, and selects this region as a high-dose region H1. Then, as illustrated in FIG. 25, the determination function 377 reduces the driving voltage of the photo sensor 232 corresponding to the scintillator 231 that corresponds to the high-dose region H1. In contrast, as illustrated in FIG. 25, the determination function 377 estimates that the X-ray dose incident on the scintillator 231 is low in a certain region, in which the count result of the scanograms at 0 degree is smaller than the threshold, in the channel direction, and selects this region as a low-dose region L1. Then, as illustrated in FIG. 25, the determination function 377 increases the driving voltage of the photo sensor 232 corresponding to the scintillator 231 that corresponds to the low-dose region L1.

Further, as illustrated in FIG. 25, the determination function 377 estimates that the X-ray dose incident on the scintillator 231 is high in a certain region, in which the count result of the scanograms at 90 degrees is equal to or larger than a threshold, in the channel direction, and selects this region as a high-dose region H2, for example. Then, as illustrated in FIG. 25, the determination function 377 reduces the driving voltage of the photo sensor 232 corresponding to the scintillator 231 that corresponds to the high-dose region H2. In contrast, as illustrated in FIG. 25, the determination function 377 estimates that the X-ray dose incident on the scintillator 231 is low in a certain region, in which the count result of the scanograms at 90 degrees is smaller than the threshold, in the channel direction, and selects this region as a low-dose region L2. Then, as illustrated in FIG. 25, the determination function 377 increases the driving voltage of the photo sensor 232 corresponding to the scintillator 231 that corresponds to the low-dose region L2.

In this manner, when the imaging angle is set to 90 degrees, the determination function 377 selects, as the low-dose region L2, a narrower range than the low-dose region L1 that is adopted while the imaging angle is set to 0 degree. Further, when the imaging angle is set to 90 degrees, the determination function 377 selects, as the high-dose region H2, a wider area than the high-dose region H1 that is adopted while the imaging angle is set to 0 degree.

The determination function 377 may determine the driving voltage by performing the threshold determination process on a representative slice, and apply the determined driving voltage to the other slices in the same manner. Alternatively, the determination function 377 may determine the driving voltage by performing the threshold determination process in each of the slice directions. The representative slice is, for example, a central slice in the slice direction.

Then, the determination function 377 determines the driving voltage corresponding to each of the photo sensors 232 for each of imaging angles other than 0 degree and 90 degrees. For example, the determination function 377 estimates a shape of the cross section of the subject P in a case where it is assumed that the cross section of the subject P has an elliptical shape, from the positional relationship among the X-ray tube 12a, the subject P, the high-dose region H1, and the low-dose region L1 at the imaging angle of 0 degree, and from the positional relationship among the X-ray tube 12a, the subject P, the high-dose region H2, and the low-dose region L2 at the imaging angle of 90 degrees. Then, the determination function 377 estimates the driving voltage corresponding to each of the photo sensors 232 for each of the imaging angles by using the estimated shape of the cross section of the subject P. In this manner, the driving voltage corresponding to each of the photo sensors 232 is determined for each of the imaging angles.

The determination function 377 may determine the driving voltage corresponding to each of the photo sensors 232 for each of the imaging angles other than 0 degree and 90 degrees, by using the same method as adopted in the case of the imaging angle of 0 degree or 90 degree.

Then, the determination function 377 generates correspondence information, in which each of the scintillators 231, the imaging angle, and the driving voltage of the photo sensor 232 corresponding to each of the scintillators 231 are associated with one another. FIG. 26 is a diagram for explaining the fifth embodiment. For example, as illustrated in FIG. 26, the determination function 377 generates correspondence information, in which an ID, a view number, and a driving voltage are associated with one another.

The "ID" in the correspondence information indicates an identifier for uniquely identifying the scintillator 231. The "view number" indicates an integrated value of view trigger signals received from the gantry control device 16. For example, in the view number, "N1≤N<N2", which indicates a range of the view number such that the view number is equal to or larger than N1 and smaller than N2, or "N2≤N<N3", which indicates a range of the view number such that the view number is equal to or larger than N2 and smaller than N3, is stored. The view number is information corresponding to the imaging angle of the X-ray tube 12a, and is reset every time the X-ray tube 12a revolves once. Further, in this example, it is assumed that the view number of zero is assigned when the X-ray tube 12a is located at the position of 0 degree (a position in the front direction of the subject P), the X-ray tube 12a starts imaging from the position of 0 degree at the start of imaging, and the view number is integrated every time the X-ray tube 12a moves in a circular orbit. The "driving voltage" indicates a driving voltage of the photo sensor 232 corresponding to the scintillator 231 identified by the ID, for each corresponding view number. Furthermore, in the example illustrated in FIG. 26, it is assumed that the driving voltage V1<the driving voltage V2, the scintillator 231 with the "ID" of "yyyy" is disposed in the high-dose region that is the edge portion in the channel direction in the X-ray detector 13a, and the scintillator 231 with the "ID" of "xxxx" is disposed in the low-dose region that is the central portion in the channel direction in the X-ray detector 13a. Moreover, it is assumed that the scintillator 231 with the "ID" of "yyyx" is disposed in a region between the central portion and the edge portion of the X-ray detector 13a in the channel direction, and may be included in the high-dose region or the low-dose region depending on the imaging angle.

As one example, the determination function 377 determines that the driving voltage of each of the APDs 141 included in the APD cell 140 of the photo sensor 232 corresponding to the scintillator 231 with the "ID" of "yyyy" is "V1" regardless of the view number. Further, the determination function 377 determines that the driving voltage of each of the APDs 141 included in the APD cell 140 of the photo sensor 232 corresponding to the scintillator 231 with the "ID" of "xxxx" is "V2" regardless of the view number. Furthermore, the determination function 377 determines that the driving voltage of each of the APDs 141 included in the APD cell 140 of the photo sensor 232 corresponding to the scintillator 231 with the "ID" of is "V2" when the view number corresponds to "N1≤N<N2", "V1" when the view number corresponds to "N2≤N<N3", "V2" when the view number corresponds to "N3≤N<N4", and "V1" when the view number corresponds to "N4≤N<N1".

The FPGA 14a sets the driving voltage corresponding to the position of each of the scintillators 231 in the photon counting detector, in the photo sensor 232 corresponding to each of the scintillators 231 at the time of imaging. For example, the FPGA 14a sets the driving voltage that is based on the X-ray dose incident on each of the scintillators 231, in the photo sensor 232 corresponding to each of the scintillators 231.

As one example, the FPGA 14a sets the driving voltage in each of the photo sensors 232 by referring to the correspondence information illustrated in FIG. 26. Here, the FPGA 14a sets, in each of the photo sensors 232, the driving voltage corresponding to the view number at the start of imaging, for example. It is assumed that the view number at the start of imaging is N1. The FPGA 14a sets the driving voltage V1 in each of the APDs 141 included in the APD cell 140 of the photo sensor 232 corresponding to the scintillator 231 with the ID of "yyyy". Further, the FPGA 14a sets the driving voltage V2 in each of the APDs 141 of the photo sensors 232 corresponding to the scintillators 231 with the IDs of "yyyx" and "xxxx". In other words, the FPGA 14a sets, in the photo sensor 232 corresponding to each of the scintillators 231, the driving voltage that is based on the X-ray dose incident on each of the scintillators 231, where the X-ray dose is estimated from the count result obtained by each of the detecting elements 230.

Figure 27:
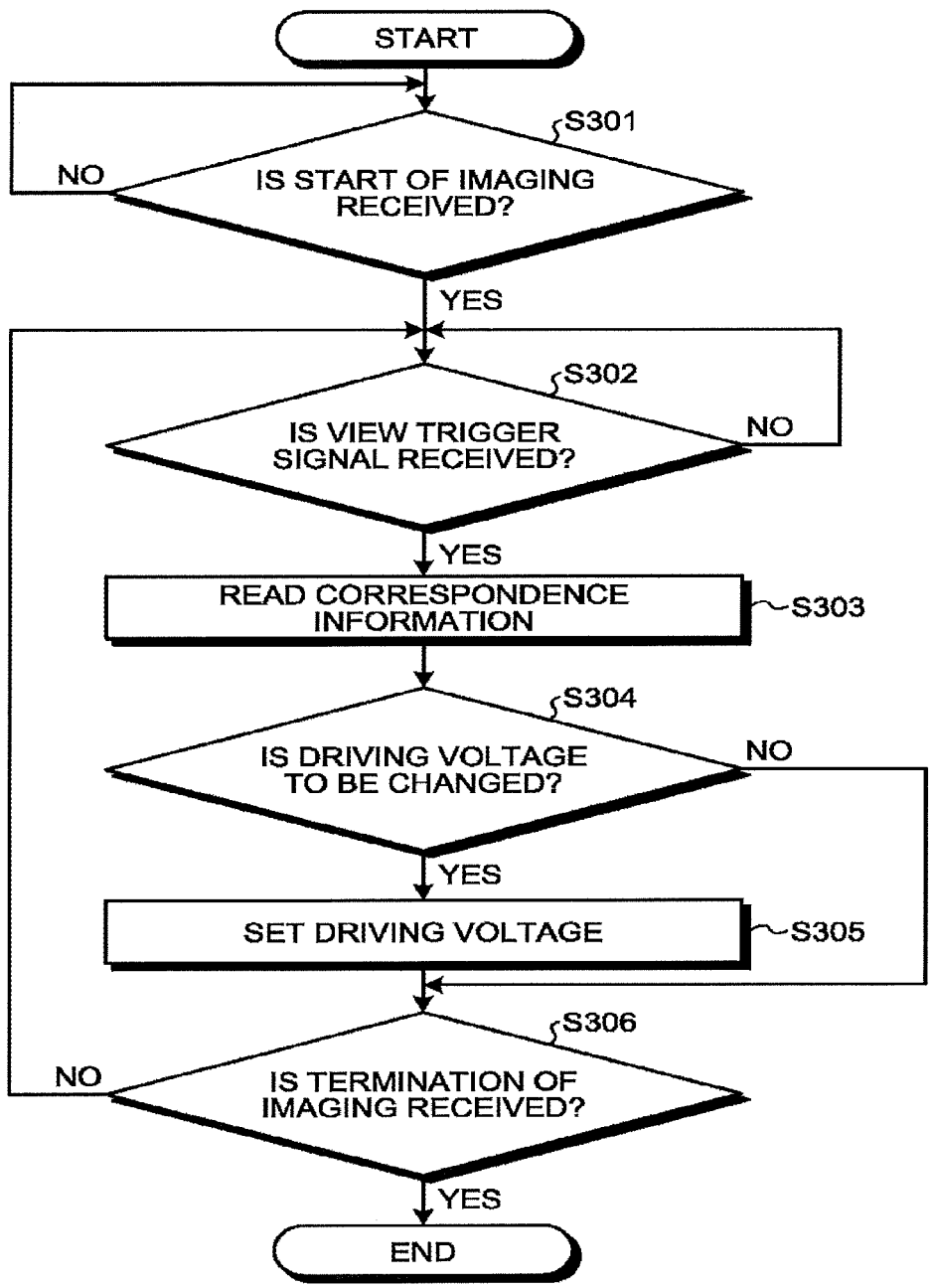
FIG. 27 is a flowchart illustrating the flow of a process performed by an FPGA according to a fifth embodiment.

Moreover, the FPGA 14a sets, in each of the photo sensors 232, the driving voltage corresponding to the view number during imaging. In other words, the FPGA 14a dynamically changes the driving voltage, which has been set before the start of imaging, depending on the imaging angle, instead of fixing the driving voltage during the imaging. FIG. 27 is a flowchart illustrating the flow of a process performed by the FPGA 14a according to the fifth embodiment.

Step S301 to Step S306 are steps implemented by the FPGA 14a. At Step S301, the FPGA 14a determines whether the start of imaging is received from the gantry control device 16. If the FPGA 14a determines that the start of imaging is received from the gantry control device 16 (Step S301: Yes), the process proceeds to Step S302. In contrast, if the FPGA 14a does not determine that the start of imaging is received from the gantry control device 16 (Step S301: No), the FPGA 14a repeats the determination process at Step S301.

At Step S302, the FPGA 14a determines whether a view trigger signal is received from the gantry control device 16. If the FPGA 14a determines that the view trigger signal is received from the gantry control device 16 (Step S302: Yes), the process proceeds to Step S303. In contrast, if the FPGA 14a does not determine that the view trigger signal is received from the gantry control device 16 (Step S302: No), the FPGA 14a repeats the determination process at Step S302.

At Step S303, the FPGA 14a reads correspondence information. For example, the FPGA 14a reads the correspondence information illustrated in FIG. 26 from the storage circuitry 35. At Step S304, the FPGA 14a determines whether the driving voltage is to be changed. For example, the FPGA 14a updates the current view number every time receiving a view trigger signal. Then, the FPGA 14a compares a driving voltage corresponding to the updated view number and a driving voltage corresponding to the view number used before the update, for each of the scintillators 231 by referring to the correspondence information. If the compared driving voltages are different, the FPGA 14a determines that the driving voltage is to be changed. In contrast, if the compared driving voltages are identical, the FPGA 14a determines that the driving voltage is not to be changed.

If the FPGA 14a determines that the driving voltage is to be changed (Step S304: Yes), the process proceeds to Step S305. In contrast, if the FPGA 14a does not determine that the driving voltage is to be changed (Step S304: No), the process proceeds to Step S306.

At Step S305, the FPGA 14a sets the driving voltage that corresponds to the updated view number. At Step S306, the FPGA 14a determines whether the termination of imaging is received from the gantry control device 16. If the FPGA 14a determines that the termination of imaging is received from the gantry control device 16 (Step S306: Yes), the FPGA 14a terminates the imaging. In contrast, if the FPGA 14a does not determine that the termination of imaging is received from the gantry control device 16 (Step S306: No), the FPGA 14a returns to Step S302 and performs the determination process.

As described above, in the fifth embodiment, the FPGA 14a sets, in each of the photo sensors 232, the driving voltage corresponding to the imaging angle during imaging. With this configuration, according to the fifth embodiment, it is possible to set optimal driving voltages for all of regions and angles adopted for imaging while the X-ray tube 12a and the X-ray detector 13 revolve once. Therefore, it is possible to obtain higher image quality and higher material decomposition capability.

In the fifth embodiment described above, the example has been described in which the X-ray dose incident on each of the scintillators 231 is estimated using two-dimensional scanogram images obtained from two directions, and the driving voltage is determined based on the estimation; however, possible embodiments are not limited to this example. For example, to determine a driving voltage corresponding to an imaging angle, it may be possible to estimate the X-ray does incident on each of the scintillators 231 on the basis of a three-dimensional scanogram image, and determine the driving voltage based on the estimation. When the X-ray does incident on each of the scintillators 231 is estimated based on the three-dimensional scanogram image and the driving voltage is determined based on the estimation, it becomes possible to split an imaging angle into smaller ranges and set processing times for theses imaging angles.

Further, in the fifth embodiment described above, the example has been described in which the FPGA 14a sets, in each of the photo sensors 232, the driving voltage corresponding to the view number at the start of imaging, for example; however, possible embodiments are not limited to this example. For example, the FPGA 14a may set the same driving voltage as an initial value in all of the photo sensors 232 at the first scan position (the view number of 1) at the start of imaging, and set driving voltages corresponding to imaging angles at subsequent view numbers starting from the view number of 2.

The reconstruction processing function 373 may perform material decomposition on the projection data, and reconstruct a material decomposition image using the material decomposition information that is a result of the material decomposition. In a case of reconstructing the material decomposition image, the reconstruction processing function 373 performs the process of correcting the spectrum of the detection data, which is explained in the fourth embodiment and the modification of the fourth embodiment, in addition to the process of correcting the count number of the detection data.

Sixth Embodiment

In a sixth embodiment, an example will be described in which an incident X-ray dose is calculated in real time, and a driving voltage is set based on the calculated X-ray dose. A configuration of the X-ray CT apparatus 1 according to a sixth embodiment is the same as the configuration of the X-ray CT apparatus 1 illustrated in FIG. 18 except that some parts of the determination function 377 and the FPGA 14*a* are different. Therefore, in the sixth embodiment, only functions executed by the determination function 377 and the FPGA 14*a* will be described.

The determination function 377 determines a driving voltage based on an X-ray dose incident on each of the scintillators 231, and generates correspondence information. For example, the determination function 377 generates correspondence information, in which each of the scintillators 231, the X-ray dose incident on each of the scintillators 231, and the driving voltage of the photo sensor 232 corresponding to each of the scintillators 231 are associated with one another. FIG. 28 is a diagram for explaining the sixth embodiment. For example, as illustrated in FIG. 28, the determination function 377 generates correspondence information, in which an ID, a count number, and a driving voltage are associated with one another.

The "ID" in the correspondence information indicates an identifier for uniquely identifying the scintillator 231. The "count number" indicates an X-ray dose incident on each of the scintillators 231 in a view unit. For example, in the "count number" corresponding to the "ID" of "yyyy", "C<C11", which indicates that a count value is smaller than C11, is stored as the X-ray dose in a view unit corresponding to a low-dose region. Further, for example, in the "count number" corresponding to the "ID" of "yyyy", "C11≤C<C12", which indicates that a count value is equal to or larger than C11 and smaller than C12, is stored as the X-ray dose in a view unit corresponding to a relatively low-dose region. Furthermore, for example, in the "count number" corresponding to the "ID" of "yyyy", "C12≤C<C13", which indicates that the count value is equal to or larger than C12 and smaller than C13, is stored as the X-ray dose in a view unit corresponding to a relatively high-dose region. Moreover, for example, in the "count number" corresponding to the "ID" of "yyyy", "C13≤C", which indicates that the count value is equal to or larger than C13, is stored as the X-ray dose in a view unit corresponding to a high-dose region.

Incidentally, there is individual variability among the photo sensors 232. To cope with this situation, it is desirable to set different count numbers for different IDs. For example, in the "count number" corresponding to the "ID" of "yyyx", "C<C21", which indicates that a count value is smaller than C21, is stored as the X-ray dose in a view unit corresponding to the low-dose region. Further, for example, in the "count number" corresponding to the "ID" of "yyyx", "C21≤C<C22", which indicates that the count value is equal to or larger than C21 and smaller than C22, is stored as the X-ray dose in a view unit corresponding to the relatively low-dose region. Furthermore, for example, in the "count number" corresponding to the "ID" of "yyyx", "C22≤C<C23", which indicates that the count value is equal to or larger than C22 and smaller than C23, is stored as the X-ray dose in a view unit corresponding to the relatively high-dose region. Moreover, for example, in the "count number" corresponding to the "ID" of "yyyx", "C23≤C", which indicates that the count value is equal to or larger than C23, is stored as the X-ray dose in a view unit corresponding to the high-dose region.

Similarly, for example, in the "count number" corresponding to the "ID" of "xxxx", "C<C31", which indicates that a count value is smaller than C31, is stored as the X-ray dose in a view unit corresponding to the low-dose region. Further, for example, in the "count number" corresponding to the "ID" of "xxxx", "C31≤C<C32", which indicates that a count value is equal to or larger than C31 and smaller than C32, is stored as the X-ray dose in a view unit corresponding to the relatively low-dose region. Furthermore, for example, in the "count number" corresponding to the "ID" of "xxxx", "C32≤C<C33", which indicates that the count value is equal to or larger than C32 and smaller than C33, is stored as the X-ray dose in a view unit corresponding to the relatively high-dose region. Moreover, for example, in the "count number" corresponding to the "ID" of "xxxx", "C33≤C", which indicates that the count value is equal to or larger than C33, is stored as the X-ray dose in a view unit corresponding to the high-dose region.

The "driving voltage" indicates a driving voltage of the photo sensor 232 corresponding to the scintillator 231 identified by the ID, with respect to the count number in a corresponding view unit. Further, in the example illustrated in FIG. 28, it is assumed that the driving voltage V1<the driving voltage V2<the driving voltage V3<the driving voltage V4.

As one example, the determination function 377 determines that the driving voltage of each of the APDs 141 included in the APD cell 140 of the photo sensor 232 corresponding to the scintillator 231 with the "ID" of "yyyy" is "V4", when the count number corresponds to "C<C11" indicating the X-ray dose corresponding to the low-dose region, "V3" when the count number corresponds to "C11≤C<C12" indicating the X-ray dose corresponding to the relatively low-dose region, "V2" when the count number corresponds to "C12≤C<C13" indicating the X-ray dose corresponding to the relatively high-dose region, and "V1" when the count number corresponds to "C13≤C" indicating the X-ray dose corresponding to the high-dose region.

The FPGA 14*a* sets the driving voltage corresponding to the position of each of the scintillators 231 in the photon counting detector, in the photo sensor 232 corresponding to each of the scintillators 231 at the time of imaging. For example, the FPGA 14*a* sets the driving voltage for a current view in the photo sensor 232 corresponding to each of the scintillators 231, on the basis of the X-ray dose that has been incident on each of the scintillators 231 for a view preceding the current view. In the sixth embodiment, it is assumed that the FPGA 14*a* sets the same driving voltage in all of the photo sensors 232 as an initial value at the first scan position (the view number of 1) at the start of imaging. Then, the FPGA 14*a* performs a process of setting the driving voltage in each of the photo sensors 232 on the basis of the X-ray dose incident on each of the scintillators 231 for each view during the imaging. Further, while an example will be described in the sixth embodiment in which the driving voltage is set using the count result obtained for a view immediately preceding the current view, but it may be possible to set the driving voltage using a count result obtained for any view preceding the current view.

Figure 29:
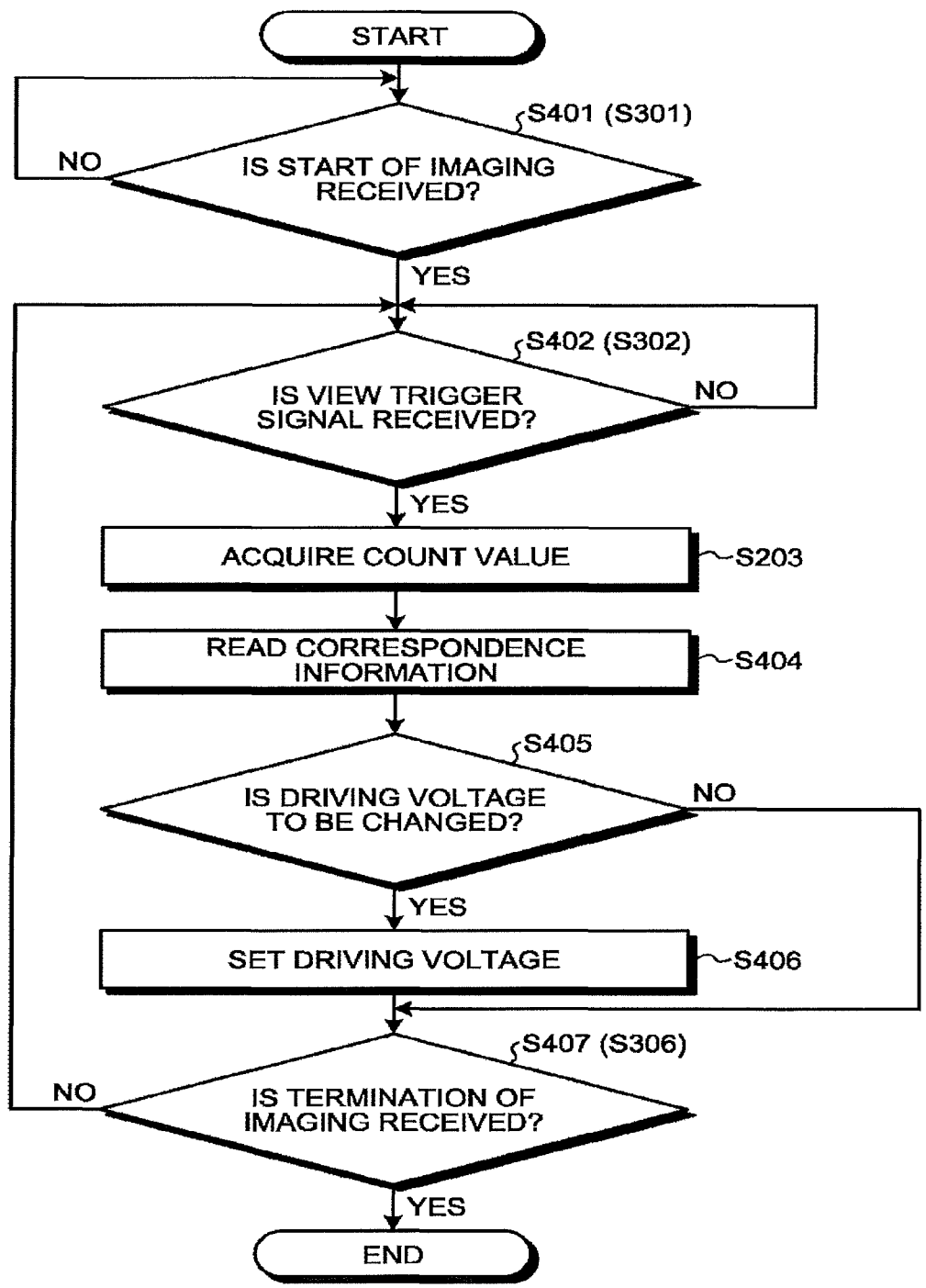
FIG. 29 is a flowchart illustrating the flow of a process performed by an FPGA according to the sixth embodiment.

FIG. 29 is a flowchart illustrating the flow of a process performed by the FPGA 14*a* according to the sixth embodiment. Processes at Step S401 and Step S402 illustrated in FIG. 29 are the same as the processes at Step S301 and Step S302 illustrated in FIG. 27.

At Step S403, the FPGA 14*a* acquires a count value from the counter 233*e*. For example, the FPGA 14*a* sets a driving voltage for a current view in the photo sensor 232 corresponding to each of the scintillators, on the basis of an X-ray dose that has been incident on each of the scintillators 231 for a view immediately preceding the current view.

A process of acquiring a count result for the immediately preceding view is first described. The FPGA 14a acquires the count result for the immediately preceding view from the counter 233e. For example, one cycle of the view trigger signal is indicated by the double-headed arrow 16a in FIG. 16. The view trigger signal of one cycle includes a positive pulse part as a first half and a negative pulse part as a second half. The FPGA 14a acquires a count result, which is obtained by performing counting in the period of one cycle of the view trigger signal, from the counter 233e.

At Step S404, the FPGA 14a reads correspondence information. For example, the FPGA 14a reads the correspondence information illustrated in FIG. 28 from the storage circuitry 35. At Step S405, the FPGA 14a determines whether the driving voltage is to be changed. For example, the FPGA 14a identifies a driving voltage corresponding to the count result for the immediately preceding view for each of the scintillators 231 by referring to the correspondence information every time the count result for the immediately preceding view is acquired. Then, the FPGA 14a compares the identified driving voltage and the driving voltage that is currently set. If the compared driving voltages are different, the FPGA 14a determines that the driving voltage is to be changed. In contrast, if the compared driving voltages are identical, the FPGA 14a determines that the driving voltage is not to be changed.

If the FPGA 14a determines that the driving voltage is to be changed (Step S405: Yes), the process proceeds to Step S406. In contrast, if the FPGA 14a does not determine that the driving voltage is to be changed (Step S405: No), the process proceeds Step S407.

At Step S406, the FPGA 14a sets the driving voltage that corresponds to the count result for the immediately preceding view. For example, when the count result acquired from the counter 233e that counts output results of the scintillator 231 identified by the ID of "yyyy" is a value equal to or larger than C11 and smaller than C12, the FPGA 14a sets the driving voltage V3 in the photo sensor 232 corresponding to the ID of "yyyy". For another example, when the count result acquired from the counter 233e that counts output results of the scintillator 231 identified by the ID of "yyyx" is a value equal to or larger than C22 and smaller than C23, the FPGA 14a sets the driving voltage V2 in the photo sensor 232 corresponding to the ID of "yyyx".

At Step S407, the FPGA 14a determines whether the termination of imaging is received from the gantry control device 16. If the FPGA 14a determines that the termination of imaging is received from the gantry control device 16 (Step S407: Yes), the FPGA 14a terminates the imaging. In contrast, if the FPGA 14a does not determine that the termination of imaging is received from the gantry control device 16 (Step S407: No), the FPGA 14a returns to Step S402 and performs the determination process. The process at Step S407 illustrated in FIG. 29 is the same as the process at Step S306 illustrated in FIG. 27.

As described above, in the sixth embodiment, the FPGA 14a sets the driving voltage based on the count result for the immediately preceding view in each of the photo sensors 232 during imaging. Therefore, according to the sixth embodiment, it is possible to set optimal driving voltages for all of regions and angles adopted for imaging while the X-ray tube 12a and the X-ray detector 13 revolve once. Consequently, it is possible to obtain higher image quality and higher material decomposition capability.

The reconstruction processing function 373 may perform material decomposition on the projection data, and reconstruct a material decomposition image using the material decomposition information that is a result of the material decomposition. In this case, to reconstruct the material decomposition image, the reconstruction processing function 373 performs the process of correcting the spectrum of the detection data, which is explained in the fourth embodiment and the modification of the fourth embodiment, in addition to the process of correcting the count number of the detection data. For example, the correspondence information illustrated in FIG. 28 is also stored in the storage circuitry 35 of the console 30. Then, the reconstruction processing function 373 selects an appropriate response function by referring to a setting value of the driving voltage when reconstructing the material decomposition image.

Modification of Sixth Embodiment

In the sixth embodiment described above, the example has been described in which the count value is calculated in a time corresponding to one cycle of the view trigger signal; however, possible embodiments are not limited to this example. For example, it may be possible to calculate the count value in a first half part or a second half part of the view trigger signal of one cycle. In other words, the FPGA 14a sets a driving voltage for a current view in the photo sensor 232 corresponding to each of the scintillators 231, on the basis of an X-ray dose that has been incident on each of the scintillators 231 in a predetermined period within the period of a past view.

More specifically, as illustrated in the upper diagram in FIG. 17, the FPGA 14a calculates a count number only from the positive pulse part 17a that is the first half of the view trigger signal, selects a driving voltage value in the negative pulse part 17b that is the second half, and sets the driving voltage at the changing point 17c of a next view trigger pulse. Alternatively, as illustrated in the lower part in FIG. 17, the FPGA 14a calculates a count number only from the negative pulse part 17d that is the second half of the view trigger signal, selects a driving voltage value in the positive pulse part 17e that is the first half, and sets the driving voltage at the changing point 17f of a next view trigger pulse. In this manner, the FPGA 14a sets the driving voltage for the current view in the photo sensor 232 corresponding to each of the scintillators 231, on the basis of the X-ray dose that has been incident on each of the scintillators in the first half part or the second half part of the period of the past view.

With this configuration, the FPGA 14a is able to eliminate a time lag between selection of the driving voltage and setting of the driving voltage. In this case, the counter 233e outputs, to the FPGA 14a, a count result used for setting the driving voltage, in addition to a count result for one cycle of the view trigger signal for reconstructing the X-ray CT image data. Further, the period for calculating the count value is not limited to the first half part or the second half part of the view trigger signal of one cycle, but may be a half period of the first half part or a half period of the second half part of the view trigger signal of one cycle.

Furthermore, in the sixth embodiment described above, the example has been described in which the FPGA 14a sets the same driving voltage as the initial value in all of the photo sensors 232 at the first scan position (the view number of 1) at the start of imaging; however, possible embodiments are not limited to this example. For example, the FPGA 14a may set the driving voltage for the first scan position (the view number of 1) using the method described in the fourth embodiment. That is, at the first scan position (the view number of 1), the FPGA 14a sets a driving voltage that is based on the X-ray dose incident on each of the scintillators, in the photo sensor 232 corresponding to each of the scintillators, by referring to the correspondence information illustrated in FIG. 23.

Moreover, while the example has been described in the sixth embodiment in which the driving voltage is set for each view, possible embodiments are not limited to this example. For example, the FPGA 14a may set a driving voltage for a predetermined view, such as for every five views.

Other Embodiments

Possible embodiments are not limited to the embodiments described above.

Figure 30:
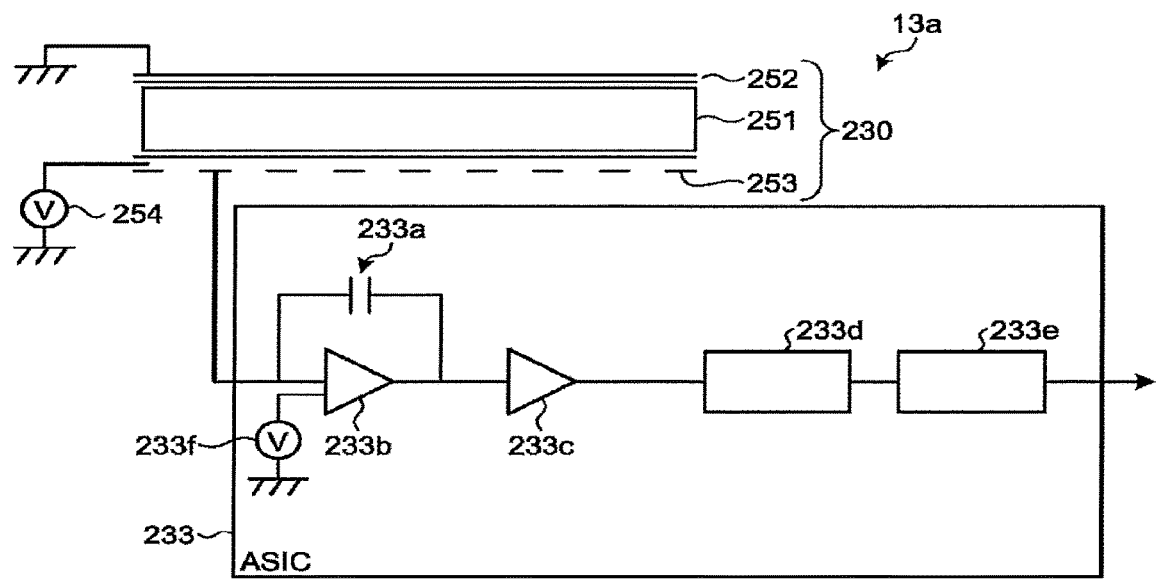
FIG. 30 is a diagram for explaining a case in which the X-ray detector is a detector of a direct conversion type.

For example, in the fourth to the sixth embodiments described above, the examples have been described in which the X-ray detector 13a is a detector of an indirect conversion type. However, in the fourth to the sixth embodiments, a detector of a direct conversion type may be adopted as the X-ray detector 13a. Therefore, with reference to FIG. 30 and FIG. 31, an example will be described in which the X-ray detector 13a is a detector of a direct conversion type. FIG. 30 is a diagram for explaining the example in which the X-ray detector 13a is a detector of a direct conversion type.

For example, as illustrated in FIG. 30, when the X-ray detector 13a is a detector of a direct conversion type, each of the detecting elements 230 includes a semiconductor 251, a single cathode electrode 252, and a plurality of anode electrodes 253.

The semiconductor 251 is a semiconductor made of cadmium telluride (CdTe), cadmium zinc telluride (CZT), or the like. The cathode electrode 252 is grounded. The plurality of the anode electrodes 253 are connected to a power supply 254. With this configuration, a driving voltage is applied to the detecting element 230 by the power supply 254. Each of the anode electrodes 253 corresponds to an individual detection pixel (also referred to as a "pixel"). When X-ray photons are incident on the detecting element 230, X-rays incident on the detecting element 230 are directly converted to electric charges and the electric charges are output to the ASIC 233.

Further, as illustrated in FIG. 30, when an amplifier included in the amplification circuitry 233b is a single-ended amplifier, the amplifier is not grounded but connected to a power supply 233f. When the amplifier is a differential amplifier, the power supply 233f is connected to the negative input of the amplifier.

In this situation, for example, a power supply circuitry (not illustrated) is disposed between the power supply 233f and the amplifier. The power supply circuitry controls the magnitude of a voltage applied to the amplifier such that the magnitude of a voltage (driving voltage) applied to the amplifier by the power supply 233f becomes equal to the magnitude of a driving voltage set by the FPGA 14a. For example, when the FPGA 14a sets the driving voltage "V4", the power supply circuitry controls the magnitude of the voltage applied to the amplifier such that the magnitude of the voltage applied to the amplifier by the power supply 233f reaches "V4".

Figure 31:
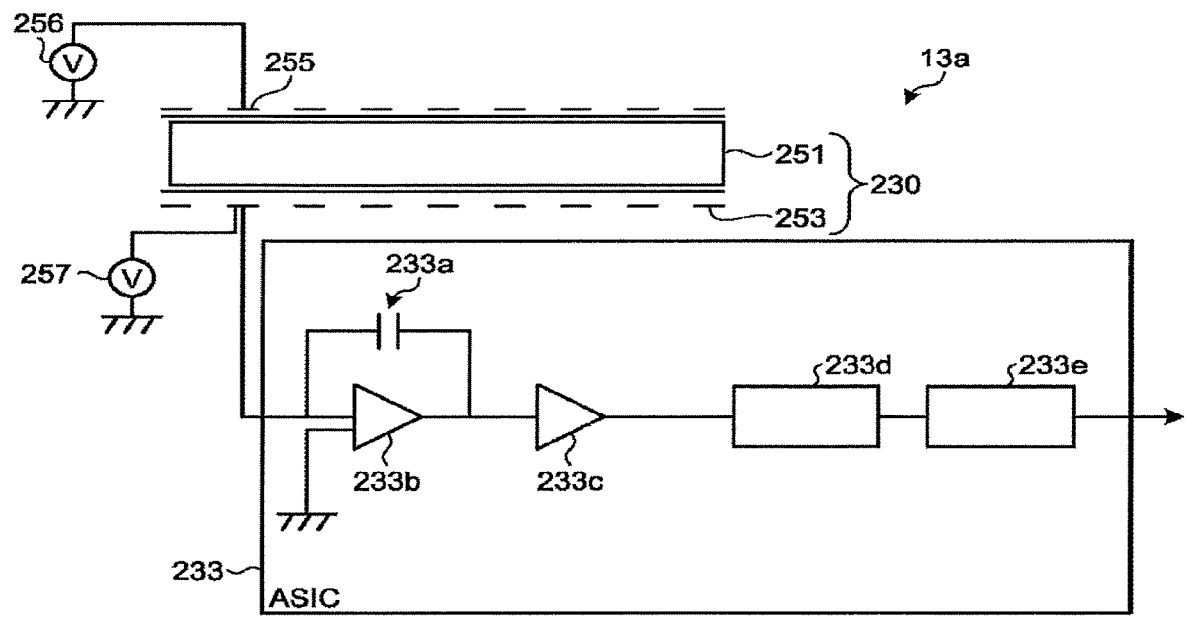
FIG. 31 is a diagram for explaining another example of a case in which the X-ray detector is a detector of a direct conversion type.

FIG. 31 is a diagram for explaining another example in which the X-ray detector 13a is a detector of a direct conversion type. The X-ray detector 13a illustrated in FIG. 31 includes a plurality of cathode electrodes 255 corresponding to a plurality of pixels, instead of a single cathode electrode, for each of the detecting elements 230. An amplifier included in the amplification circuitry 233b is grounded. A power supply 256 is connected to the cathode electrode 255, and a power supply 257 is connected to the anode electrode 253, for each of the pixels. With this configuration, a driving voltage that corresponds to a potential difference between a potential of the power supply 256 and a potential of the power supply 257 is applied to the detecting element 230.

In this situation, for example, a power supply circuitry (not illustrated) is disposed between the power supply 257 and the anode electrode 253. The power supply circuitry controls the magnitude of a voltage applied by the power supply 257 such that the magnitude of a driving voltage applied to the detecting element 230 becomes equal to the magnitude of a driving voltage set by the FPGA 14a, to thereby control the magnitude of the voltage applied to the detecting element 230. For example, when the FPGA 14a sets the driving voltage to "V1", the power supply circuitry controls the magnitude of the driving voltage applied to the power supply 257 such that the magnitude of the voltage applied to the detecting element 230 reaches "V1".

Further, in the embodiments described above, the example has been described in which the processing time or the driving voltage is determined using a two-dimensional scanogram image or a three-dimensional scanogram image that is obtained by capturing a scanogram before performing imaging through main scan; however, possible embodiments are not limited to this example. For example, it may be possible to determine the processing time or the driving voltage by using a past image of the same subject or an image captured by a different medical-image diagnostic apparatus.

Furthermore, in the embodiments described above, the example has been described in which the single X-ray CT apparatus 1 determines one of the processing time and the driving voltage. However, the X-ray CT apparatus 1 may determine both of the processing time and the driving voltage, and set the determined processing time and the determined driving voltage.

Moreover, the determination function 377 may determine the processing time or the driving voltage by estimating the X-ray dose that is incident on each of the detecting elements 130 and 230 on the basis of information related to a body type of a subject. For example, the determination function 377 acquires, as the information on the body type, a body thickness of the subject from a reconstructed image that is obtained by reconstructing a three-dimensional scanogram image, and estimates the X-ray dose incident on each of the detecting elements 130 and 230. More specifically, the determination function 377 acquires, as the body thickness of the subject, lengths in the vertical direction and the horizontal direction in an axial image obtained by reconstructing the three-dimensional scanogram image, and estimates the X-ray dose incident on each of the detecting elements 130 and 230 on the basis of the amount of attenuation of X-rays depending on the body thickness. Then, the determination function 377 performs a threshold determination process on the estimated X-ray dose, and determines a processing time or a driving voltage. In this case, the FPGA 14a sets, in each of the ASICs 134, the processing time that is based on the X-ray dose incident on each of the detecting elements 130, where the X-ray dose is estimated from the information on the body type of the subject. Further, the FPGA 14a sets, in the photo sensor 232 corresponding to each of the scintillators 231, the driving voltage that is based on the X-ray dose incident on each of the scintillators 231, where the X-ray dose is estimated from the information on the body type of the subject.

Furthermore, the determination function 377 may determine a processing time or a driving voltage by estimating the X-ray dose incident on each of the detecting elements 130 and 230 on the basis of information on a body type of a subject, where the information is stored as patient information. For example, the determination function 377 acquires information on the height, the weight, the chest circumference, the waist circumference, and the like that are stored as the patient information in the storage circuitry 35, and estimates the X-ray dose incident on each of the detecting elements 230 and 230. Then, the determination function 377 performs a threshold determination process on the estimated X-ray dose, and determines a processing time or a driving voltage. Alternatively, the determination function 377 may receive input of information on the height, the weight, the chest circumference, the waist circumference, and the like of the subject P from an operator via the input interface 31, estimate the X-ray dose incident on each of the detecting elements 130 and 230 from the received information, and determine a processing time or a driving voltage. In this case, the FPGA 14a sets, in each of the ASICs 134, the processing time that is based on the X-ray dose incident on each of the detecting elements 130, where the X-ray dose is estimated from the information on the body type of the subject, which is stored as the patient information. Moreover, the FPGA 14a sets, in the photo sensor 232 corresponding to each of the scintillators 231, the driving voltage that is based on the X-ray dose incident on each of the scintillators 231, where the X-ray dose is estimated from the information on the body type of the subject, which is stored as the patient information.

Furthermore, in the embodiments described above, the example has been described in which a single threshold is set so as to set two kinds of processing times or driving voltages; however, possible embodiments are not limited to this example. For example, it may be possible to set a plurality of thresholds, and determine three or more kinds of processing times or driving voltages. In this case, the FPGA 14a sets, in each of the ASICs 134, the three or more kinds of processing times determined as above. Further, the FPGA 14a sets, in each of the photo sensors 232, the three or more kinds of driving voltages determined as above.

Moreover, in the embodiments described above, the example has been described in which the processing time is determined based on the X-ray dose incident on the detecting element 130; however, possible embodiments are not limited to this example. For example, it may be possible to set different processing times for the central portion and the edge portions in the channel direction, without estimating the X-ray dose incident on each of the detecting elements 130. For example, the FPGA 14a sets a larger processing time in the ASIC 134 that is connected to the detecting element 130 disposed in a first region that is the central portion in the channel direction in the X-ray detector 13, as compared to the ASIC 134 that is connected to the detecting element 130 disposed in a second region that is the edge portion in the channel direction. In addition, the FPGA 14a may set processing times such that the processing times are gradually reduced from the central portion to the edge portions in the channel direction of the X-ray detector 13.

Furthermore, in the embodiments described above, the example has been described in which the driving voltage is determined based on the X-ray dose incident on each of the scintillators 231; however, possible embodiments are not limited to this example. For example, it may be possible to set different driving voltages for the central portion and the edge portions in the channel direction, without estimating the X-ray dose incident on in each of the scintillators 231. For example, the FPGA 14a sets a larger driving voltage in the photo sensor 232 of the detecting element 230 disposed in the first region that is the central portion in the channel direction of the X-ray detector 13a, as compared to the photo sensor 232 of the detecting element 230 disposed in the second region that is the edge portion in the channel direction. In addition, the FPGA 14a may set driving voltages such that the driving voltages are gradually reduced from the central portion to the edge portions in the channel direction of the X-ray detector 13a.

Moreover, the FPGA 14a may set a processing time corresponding to an imaging angle in each of the ASICs 134, without estimating the X-ray dose incident on each of the detecting elements. For example, the FPGA 14a may change a range of the first region and a range of the second region depending on an imaging angle, and set a larger processing time in the ASIC 134 that is connected to the detecting element 230 disposed in the changed first region, as compared to the the ASIC 134 that is connected to the detecting element 230 disposed in the changed second region.

Furthermore, the FPGA 14a may set a driving voltage corresponding to an imaging angle in each of the photo sensors 232, without estimating the X-ray dose incident on each of the scintillators 231. For example, the FPGA 14a may change a range of the first region and a range of the second region depending on an imaging angle, and set a larger driving voltage in the photo sensor 232 of the detecting element 230 that is disposed in the changed first region, as compared to the photo sensor 232 of the detecting element 230 that is disposed in the changed second region.

Moreover, in the embodiments described above, the example has been described in which the ASICs 134 and 233 are disposed on the X-ray detectors 13 and 13a, respectively; however, possible embodiments are not limited to this example. For example, the ASICs 134 and 233 may be disposed on the data acquisition circuitry 14.

Furthermore, in the embodiments described above, the example has been described in which the reconstruction processing function 373 performs material decomposition on the projection data and obtains material decomposition information; however, possible embodiments are not limited to this example. For example, the reconstruction processing function 373 may perform material decomposition on image data and acquire material decomposition information.

Moreover, in the embodiments described above, the X-ray CT apparatus 1 of a rotate-rotate type (third generation CT) has been described, in which the X-ray tube 12a and the X-ray detector 13 or 13a revolve around the subject in an integrated manner; however, possible embodiments are not limited to this example. For example, an X-ray CT apparatus of a stationary-rotate type (fourth generation CT) is known, in which X-ray detectors each including a plurality of X-ray detecting elements are distributed and fixed in a ring shape, and only the X-ray tube revolves around the subject. The embodiments described above are applicable to the fourth generation CT. In addition, the embodiments described above are also applicable to an X-ray CT apparatus of a hybrid type, in which the third generation CT and the fourth generation CT are combined.

Furthermore, the embodiments described above are also applicable to an X-ray CT apparatus of a conventional single tube type, and an X-ray CT apparatus of what is called a multi-tube type, in which a plurality of pairs of an X-ray tube and a detector are mounted on a rotating ring.

Moreover, in the embodiments described above, the example has been described in which the processing circuitry 37 implements a plurality of functions; however, possible embodiments are not limited to this example. For example, the plurality of functions may be provided as independent circuitries in the console 30, and each of the circuitries may implement the corresponding function. For example, it may be possible to provide a determination circuitry for the determination function 377 implemented by the processing circuitry 37, and cause the determination circuitry to implement the determination function. For another example, it may be possible to provide a pre-processing circuitry for the pre-processing function 372 implemented by the processing circuitry 37, and cause the pre-processing circuitry to implement the pre-processing function. For still another example, it may be possible to provide a reconstruction processing circuitry for the reconstruction processing function 373 implemented by the processing circuitry 37, and cause the reconstruction processing circuitry to implement the reconstruction function.

Moreover, various functions implemented by the processing circuitry 37 and various functions implemented by the FPGA 14a as described above may be implemented by a single processing circuitry.

Furthermore, in the embodiments described above, the example has been described in which the pre-processing function 372, the determination function 377, and the reconstruction processing function 373 are implemented in the console 30; however, possible embodiments are not limited to this example. For example, it may be possible to cause an external workstation to implement the pre-processing function 372, the determination function 377, and the reconstruction processing function 373.

Moreover, the processing time determination process and the material decomposition process explained in the embodiments described above may be implemented by software. For example, the processing time determination process may be implemented by causing a computer to execute a processing time determination program that defines the flow of the process performed by the determination function 377 described in the embodiments above. For another example, the driving voltage determination process may be implemented by causing a computer to execute a driving voltage determination program that defines the flow of the process performed by the determination function 377 described in the embodiments above. For still another example, the material decomposition process may be implemented by causing a computer to execute a material decomposition program that defines the flow of the process performed by the pre-processing function 372 and the reconstruction processing function 373 described in the embodiments above. The processing time determination program, the driving voltage determination program, and the material decomposition program as described above are stored in, for example, a hard disk, a semiconductor memory device, or the like, and are read and executed by a processor, such as a CPU or an MPU. In addition, the material decomposition program may be stored in and distributed with a computer-readable recording medium, such as a compact disc-read only memory (CD-ROM), a magnetic optical disk (MO), or a digital versatile disc (DVD).

The term "processor" used in the above explanation denotes, for example, a CPU, a graphics processing unit (GPU), or a circuitry such as an ASIC or a programmable logic device (e.g., a simple programmable logic device (SPLD), a complex programmable logic device (CPLD), or a field programmable gate array (FPGA)). The processor implements the functions by reading and executing the programs incorporated in the circuitries thereof. It may be possible to store the programs in the storage circuitry 35 included in the console 30, instead of incorporating the programs in the circuitries of the processor. In this case, the processor implements the functions by reading and executing the programs stored in the storage circuitry 35. Each of the processors in the present embodiments does not necessarily have to be configured as a single circuitry. It may be possible to configure a single processor by combining a plurality of independent circuitries to implement the functions. In addition, it may be possible to integrate a plurality of components illustrated in FIG. 1 into a single processor to implement the functions.

In the explanation of the embodiments above, the components illustrated in the drawings are functionally conceptual and do not necessarily have to be physically configured in the manner illustrated in the drawings. In other words, specific forms of distribution and integration of the apparatuses are not limited to those illustrated in the drawings, and all or part of the apparatuses may be functionally or physically distributed or integrated in arbitrary units depending on various loads or use conditions. Further, for each processing function performed by each apparatus, all or any part of the processing functions may be implemented by a CPU and a program analyzed and executed by the CPU or may be implemented as hardware by wired logic.

Furthermore, the control methods described in the embodiments above may be implemented by causing a computer, such as a personal computer or a workstation, to execute a control program that is prepared in advance. The control program may be distributed via a network, such as the Internet. Moreover, the control program may be stored in a computer-readable recording medium, such as a flexible disk (FD), a CD-ROM, an MO, or a DVD, and executed by being read from the recording medium by the computer.

According to at least one aspect of the embodiments described above, it is possible to realize a high material decomposition capability.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray CT apparatus comprising:
a photon counting detector including a plurality of detecting elements, each detecting element of the plurality of detecting elements is configured to detect X-rays; and
a processing circuitry configured to set a control parameter corresponding to a position of each detecting element of the plurality of detecting elements in the photon counting detector, wherein the processing circuitry sets a longer processing time in counting circuitry that is connected to a detecting element of the plurality of detecting elements for which an X-ray incident dose is smaller than a threshold, as compared to counting circuitry that is connected to a detecting element of the plurality of detecting elements for which an X-ray incident dose is equal to or larger than the threshold.

2. The X-ray CT apparatus according to claim 1, wherein the photon counting detector includes a plurality of detection circuitries, each detection circuitry of the plurality of detection circuitries includes:
   a detecting element of the plurality of detecting elements configured to detect X-ray photons; and
   a counting circuitry connected to the detecting element and configured to count the X-ray photons detected by the detecting element, and
the processing circuitry sets, as the control parameter, a processing time corresponding to the position of each detecting element of the plurality of detecting elements in the photon counting detector, in the counting circuitry connected to each detecting element of the plurality of detecting elements at a time of imaging.

3. The X-ray CT apparatus according to claim 2, wherein the processing circuitry sets, in each counting circuitry of a plurality of counting circuitries, a processing time that is based on an X-ray dose incident on each detecting element of the plurality of detecting elements.

4. The X-ray CT apparatus according to claim 3, wherein the processing circuitry sets, in each counting circuitry of the plurality of counting circuitries, a processing time that is based on an X-ray dose incident on each detecting element of the plurality of detecting elements, the X-ray dose being estimated from a count result obtained by each detecting element of the plurality of detecting elements.

5. An X-ray CT apparatus comprising:
   a photon counting detector including a plurality of detecting elements, each detecting element of the plurality of detecting elements is configured to detect X-rays; and
   a processing circuitry configured to set a control parameter corresponding to a position of each detecting element of the plurality of detecting elements in the photon counting detector, wherein
   the photon counting detector includes a plurality of detection circuitries, each detection circuitry of the plurality of detection circuitries includes:
      a detecting element of the plurality of detecting elements configured to detect X-ray photons; and
      a counting circuitry connected to the detecting element and configured to count the X-ray photons detected by the detecting element, and
   the processing circuitry sets, as the control parameter, a processing time corresponding to the position of each detecting element of the plurality of detecting elements in the photon counting detector, in the counting circuitry connected to each detecting element of the plurality of detecting elements at a time of imaging, wherein
   the processing circuitry sets a processing time corresponding to an imaging angle in each counting circuitry of a plurality of counting circuitries.

6. An X-ray CT apparatus comprising:
   a photon counting detector including a plurality of detecting elements, each detecting element of the plurality of detecting elements is configured to detect X-rays; and
   a processing circuitry configured to set a control parameter corresponding to a position of each detecting element of the plurality of detecting elements in the photon counting detector, wherein
   the photon counting detector includes a plurality of detection circuitries, each detection circuitry of the plurality of detection circuitries includes:
      a detecting element of the plurality of detecting elements configured to detect X-ray photons; and
      a counting circuitry connected to the detecting element and configured to count the X-ray photons detected by the detecting element, and
   the processing circuitry sets, as the control parameter, a processing time corresponding to the position of each detecting element of the plurality of detecting elements in the photon counting detector, in the counting circuitry connected to each detecting element of the plurality of detecting elements at a time of imaging, wherein
   the processing circuitry sets a longer processing time in a counting circuitry that is connected to a detecting element disposed in a first region that is a central portion in a channel direction in the photon counting detector, as compared to a counting circuitry that is connected to a detecting element disposed in a second region that is an edge portion in the channel direction.

7. The X-ray CT apparatus according to claim 6, wherein the processing circuitry changes a range of the first region and a range of the second region depending on an imaging angle, and sets a longer processing time in a counting circuitry that is connected to a detecting element disposed in the changed first region, as compared to a counting circuitry that is connected to a detecting element disposed in the changed second region.

8. An X-ray CT apparatus comprising:
   a photon counting detector including a plurality of detecting elements, each detecting element of the plurality of detecting elements is configured to detect X-rays; and
   a processing circuitry configured to set a control parameter corresponding to a position of each detecting element of the plurality of detecting elements in the photon counting detector, wherein
   the photon counting detector includes a plurality of detection circuitries, each detection circuitry of the plurality of detection circuitries includes:
      a detecting element of the plurality of detecting elements configured to detect X-ray photons; and
      a counting circuitry connected to the detecting element and configured to count the X-ray photons detected by the detecting element, and
   the processing circuitry sets, as the control parameter, a processing time corresponding to the position of each detecting element of the plurality of detecting elements in the photon counting detector, in the counting circuitry connected to each detecting element of the plurality of detecting elements at a time of imaging, wherein
   the processing circuitry sets a processing time for a current view in a counting circuitry connected to each detecting element of the plurality of detecting elements, on a basis of an X-ray dose that has been incident on each detecting element of the plurality of detecting elements for a past view preceding the current view.

9. The X-ray CT apparatus according to claim 8, wherein the processing circuitry adopts a view immediately preceding the current view as the past view, and sets a processing time for the current view in a counting circuitry connected to each detecting element of the plurality of detecting elements, on a basis of an X-ray dose that has been incident on each detecting element of the plurality of detecting elements for the past view.

10. The X-ray CT apparatus according to claim 8, wherein the processing circuitry sets a processing time for the current view in a counting circuitry connected to each detecting element of the plurality of detecting elements, on a basis of an X-ray dose that has been incident on each detecting element of the plurality of detecting elements in a predetermined period within a period of the past view.

11. The X-ray CT apparatus according to claim 10, wherein the processing circuitry sets a processing time for the current view in a counting circuitry connected to each detecting element of the plurality of detecting elements, on a basis of an X-ray dose that has been incident on each detecting element of the plurality of detecting elements in one of a first half part and a second half part of the period of the past view.

12. An X-ray CT apparatus comprising:
a photon counting detector including a plurality of detecting elements, each detecting element of the plurality of detecting elements is configured to detect X-rays;
a processing circuitry configured to set a control parameter corresponding to a position of each detecting elements of the plurality of detecting elements in the photon counting detector; and
an acquisition circuitry configured to acquire a count result of the photon counting detector, wherein
the processing circuitry corrects the count result so that an X-ray dose and the count result have a linear relationship and reconstructs an image based on the corrected count result.

13. An X-ray CT apparatus comprising:
a photon counting detector including a plurality of detecting elements, each detecting element of the plurality of detecting elements is configured to detect X-rays; and
a processing circuitry configured to set a control parameter corresponding to a position of each detecting element of the plurality of detecting elements in the photon counting detector, wherein
the photon counting detector includes a plurality of detection circuitries, each detection circuitry of the plurality of detection circuitries includes:
a detecting element of the plurality of detecting elements configured to detect X-ray photons; and
a counting circuitry connected to the detecting element and configured to count the X-ray photons detected by the detecting element, and
the processing circuitry sets, as the control parameter, a processing time corresponding to the position of each detecting element of the plurality of detecting elements in the photon counting detector, in the counting circuitry connected to each detecting element of the plurality of detecting elements at a time of imaging, wherein
the processing circuitry sets a processing time of each counting circuitry of a plurality of counting circuitries to be an integral time in each counting circuitry of the plurality of counting circuitries.

14. An X-ray CT apparatus comprising:
a photon counting detector including a plurality of detecting elements, each detecting element of the plurality of detecting elements is configured to detect X-rays; and
a processing circuitry configured to set a control parameter corresponding to a position of each detecting element of the plurality of detecting elements in the photon counting detector, wherein
the processing circuitry sets, as the control parameter, a driving voltage corresponding to the position of each detecting element of the plurality of detecting elements in the photon counting detector, in each detecting element of the plurality of detecting elements at a time of imaging, wherein
each detecting element of the plurality of detecting elements includes a scintillator and a photo sensor, and the processing circuitry sets a driving voltage corresponding to a position of each scintillator of a plurality of scintillators in the photon counting detector, in the photo sensor corresponding to each scintillator of the plurality of scintillators at a time of imaging,
wherein the processing circuitry sets, in the photo sensor corresponding to each scintillator of the plurality of scintillators, a driving voltage that is based on an X-ray dose incident on each scintillator of the plurality of scintillators.

15. The X-ray CT apparatus according to claim 14, wherein the processing circuitry estimates an X-ray dose incident on each detecting element of the plurality of detecting elements from a count result obtained by each detecting element of the plurality of detecting elements, and sets, in each photo sensor of a plurality of photo sensors, the driving voltage that is based on the X-ray dose.

16. The X-ray CT apparatus according to claim 14, wherein the processing circuitry estimates an X-ray dose incident on each detecting element of the plurality of detecting elements from information on a body type of a subject and sets, in each photo sensor of a plurality of photo sensors, the driving voltage that is based on the X-ray dose.

17. The X-ray CT apparatus according to claim 14, wherein the processing circuitry sets a larger driving voltage in a photo sensor for which an X-ray dose is smaller than a threshold, as compared to a photo sensor for which an X-ray dose is equal to or larger than the threshold.

18. The X-ray CT apparatus according to claim 14, wherein the photo sensor is one of an avalanche photodiode and a silicon photomultiplier.

19. An X-ray CT apparatus comprising:
a photon counting detector including a plurality of detecting elements, each detecting element of the plurality of detecting elements is configured to detect X-rays; and
a processing circuitry configured to set a control parameter corresponding to a position of each detecting element of the plurality of detecting elements in the photon counting detector, wherein
the processing circuitry sets, as the control parameter, a driving voltage corresponding to the position of each detecting element of the plurality of detecting elements in the photon counting detector, in each detecting element of the plurality of detecting elements at a time of imaging, wherein
each detecting element of the plurality of detecting elements includes a scintillator and a photo sensor, and
the processing circuitry sets a driving voltage corresponding to a position of each scintillator of a plurality of scintillators in the photon counting detector, in the photo sensor corresponding to each scintillator of the plurality of scintillators at a time of imaging,
wherein the processing circuitry sets a driving voltage corresponding to an imaging angle in each photo sensor of a plurality of photo sensors.

20. An X-ray CT apparatus comprising:
a photon counting detector including a plurality of detecting elements, each detecting element of the plurality of detecting elements is configured to detect X-rays; and
a processing circuitry configured to set a control parameter corresponding to a position of each detecting element of the plurality of detecting elements in the photon counting detector, wherein
the processing circuitry sets, as the control parameter, a driving voltage corresponding to the position of each detecting element of the plurality of detecting elements in the photon counting detector, in each detecting element of the plurality of detecting elements at a time of imaging, wherein each detecting element of the plurality of detecting elements includes a scintillator and a photo sensor, and the processing circuitry sets a driving voltage corresponding to a position of each scintillator of a plurality of scintillators in the photon counting detector, in the photo sensor corresponding to each scintillator of the plurality of scintillators at a time of imaging, wherein the processing circuitry sets a larger driving voltage in a photo sensor of a detecting element disposed in a first region that is a central portion in a channel direction in the photon counting detector, as compared to a photo sensor of a detecting element disposed in a second region that is an edge portion in the channel direction.

21. The X-ray CT apparatus according to claim 20, wherein the processing circuitry changes a range of the first region and a range of the second region depending on an imaging angle, and sets a larger driving voltage in a photo sensor of a detecting element that is disposed in the changed first region, as compared to a photo sensor of a detecting element that is disposed in the changed second region.

22. An X-ray CT apparatus comprising:

a photon counting detector including a plurality of detecting elements, each detecting element of the plurality of detecting elements is configured to detect X-rays; and a processing circuitry configured to set a control parameter corresponding to a position of each detecting element of the plurality of detecting elements in the photon counting detector, wherein the processing circuitry sets, as the control parameter, a driving voltage corresponding to the position of each detecting element of the plurality of detecting elements in the photon counting detector, in each detecting element of the plurality of detecting elements at a time of imaging, wherein each detecting element of the plurality of detecting elements includes a scintillator and a photo sensor, and the processing circuitry sets a driving voltage corresponding to a position of each scintillator of a plurality of scintillators in the photon counting detector, in the photo sensor corresponding to each scintillator of the plurality of scintillators at a time of imaging, wherein the processing circuitry sets a driving voltage for a current view in a photo sensor corresponding to each scintillator of the plurality of scintillators, on a basis of an X-ray dose that has been incident on each scintillator of the plurality of scintillators for a past view preceding the current view.

23. The X-ray CT apparatus according to claim 22, wherein the processing circuitry adopts a view immediately preceding the current view as the past view.

24. The X-ray CT apparatus according to claim 22, wherein the processing circuitry sets the driving voltage for the current view in the photo sensor corresponding to each scintillator of the plurality of scintillators, on a basis of an X-ray dose that has been incident on each scintillator of the plurality of scintillators in a predetermined period within a period of the past view.

25. The X-ray CT apparatus according to claim 24, wherein the processing circuitry sets the driving voltage for the current view in the photo sensor corresponding to each scintillator of the plurality of scintillators, on a basis of an X-ray dose that has been incident on each scintillator of the plurality of scintillators in one of a first half part and a second half part of the period of the past view.

26. An X-ray CT apparatus comprising:

a photon counting detector including a plurality of detecting elements, each detecting element of the plurality of detecting elements is configured to detect X-rays;

a processing circuitry configured to set a control parameter corresponding to a position of each detecting element of the plurality of detecting elements in the photon counting detector; and an acquisition circuitry configured to acquire a count result of the photon counting detector, wherein the processing circuitry sets, as the control parameter, a driving voltage corresponding to the position of each detecting element of the plurality of detecting elements in the photon counting detector, in each detecting element of the plurality of detecting elements at a time of imaging, wherein the processing circuitry corrects the count result so that an X-ray dose and the count result have a linear relationship and reconstructs an image based on the corrected count result.

27. An X-ray CT apparatus comprising:

a photon counting detector including a plurality of detecting elements, each detecting element of the plurality of detecting elements is configured to detect X-rays; and a processing circuitry configured to set a control parameter corresponding to a position of each detecting element of the plurality of detecting elements in the photon counting detector, wherein the photon counting detector includes a plurality of detection circuitries, each detection circuitry of the plurality of detection circuitries includes:

a detecting element of the plurality of detecting elements configured to detect X-ray photons; and a counting circuitry connected to the detecting element and configured to count the X-ray photons detected by the detecting element, and the processing circuitry:

sets, as the control parameter, a processing time corresponding to the position of each detecting element of the plurality of detecting elements in the photon counting detector, in a counting circuitry connected to each detecting element of the plurality of detecting elements at a time of imaging, and sets, as the control parameter, a driving voltage corresponding to the position of each detecting element of the plurality of detecting elements in the photon counting detector, in each detecting element of the plurality of detecting elements at the time of imaging.

* * * * *